US007115766B2

(12) United States Patent
Mulholland et al.

(10) Patent No.: US 7,115,766 B2
(45) Date of Patent: Oct. 3, 2006

(54) NUCLEOPHILIC APPROACH FOR PREPARING RADIOLABELED IMAGING AGENTS AND ASSOCIATED COMPOUNDS

(75) Inventors: G. Keith Mulholland, Indianapolis, IN (US); Martin J. O'Donnell, Indianapolis, IN (US); Frederick T. Chin, Walnut Creek, CA (US); Francisca Delgado, Madrid (ES)

(73) Assignee: Indiana University Research & Technology Corp., Indianapolis, IN (US)

( * ) Notice: Subject to any disclaimer, the term of this patent is extended or adjusted under 35 U.S.C. 154(b) by 132 days.

(21) Appl. No.: 10/433,053

(22) PCT Filed: Nov. 30, 2001

(86) PCT No.: PCT/US01/45685

§ 371 (c)(1),
(2), (4) Date: May 29, 2003

(87) PCT Pub. No.: WO02/44144

PCT Pub. Date: Jun. 6, 2002

(65) Prior Publication Data

US 2004/0034246 A1    Feb. 19, 2004

Related U.S. Application Data

(60) Provisional application No. 60/250,111, filed on Nov. 30, 2000.

(51) Int. Cl.
C07C 205/06 (2006.01)
C07C 205/00 (2006.01)

(52) U.S. Cl. .................. 560/21; 560/8; 560/9; 560/19; 560/433; 206/569

(58) Field of Classification Search ................ 560/433, 560/8, 9, 19, 21; 206/569
See application file for complete search history.

(56) References Cited

U.S. PATENT DOCUMENTS 4,762,881 A * 8/1988 Kauer ..................... 525/54.11

OTHER PUBLICATIONS

"No-Carrier-Added (NCA) ARYL [18F] Fluorides Via the Nucleophilic Aromatic Substitution of Electron-Rich Aromatic Rings," Ding et al. *Journal of Fluorine Chemistry* vol. 48, pp. 189-205 (1990).
"Synthesis of 18F Labelled Fluoro-m-tyrosine, Fluoro-m-tyramine and Fluoro-3-hydroxyphenylacetic Acid," Raman Chirakal, Gary J. Schrobilgen, Gunter Fimau and Stephen Garnett, Appl. Radiat. Isot. 1991 42, No. 2, 113-119.
"Synthesis of Radiofluorinated Analogs of m-Tyrosine as Potential L-Dopa Tracers via Direct Reaction with Acetylhypofluorite," OT DeJesus et al., Appl. Radiat. Isot. vol. 41, No. 5, pp. 433-437, 1990.
Enzymatic synthesis of no-carrier-added 6-[18F]fluoro-L-dopa with β-tyrosinase, SciFinder Scholar, Nov. 19, 2000, p. 3 (Abstract).
"The Synthesis of 6-[18F] Fluoro-L-Dopa by Chiral Catalytic Phase-Transfer Alkylation," C. Lemaire et al., J. Label Labelled Cpd., Radiopharm 42 (1999) S113-S115.
"Monograph series on aging-related diseases: XII," N. Kontakos and J. Stokes, Chronic Dis. Can. 1999 20, 58-76 (Abstract).
"Asymmetric Synthesis of 6-{18F} Fluoro-L-Dopa Using a Chiral Nickel Complex of the Schiff Base of (s)-O-[(N-Benzylprolyl)-Amino] Benzophenone and Glycine," r. n. Krasikova, et al., J. Label Labelled Cpd., Radiopharm. 1999, 42, 512-5104.
"Enantioselective Synthesis of 6-[Fluorine-18]-Fluoro-L-Dopa from No-Carrier-Added Fluorine-18-Fluoride," Christian Lemaire, et al., The Journal of Nuclear Medicine, 1994, 35, 1996-2002.
"No-Carrier-Added (NCA) Aryl [18F] Fluorides via the Nucleophilic Aromatic Substitution of Electron-rich Aromatic Rings,"Y.S. Ding, et al., Journal of Fluorine Chemistry, 48 (1990) 189-205.
"Dopamine visualized in the basal ganglia of living man," E.S. Garnett, et al., Nature Sep., 1983, 305, 137-138.
"Parkinson's Disease and the U.S. Health Care System," Pamela P. Fischer, RN,BSN, Journal of Community Health Nursing, 1999 16(3), 191-204.
"The Natural History of Parkinson's Disease," W.H. Poewe, MD et al., American Neurological Association, 1998, pp. S1-S9.
"PET studies of functional compensation in a primate model of Parkinson's disease," JL. Eberling, et al., Neuroreport. 8(12):2727-33, Aug. 18, 1997 (Abstract).
"Understanding Parkinson's Disease," Moussa B. H. Youdim, et al., Scientific American, Jan. 1997, pp. 52-59.
"Synthesis of 6-[18F] and 4-[18F]fluoro-L-m-tyrosines via regioselective radiofluorodestannylation," SciFinder Scholar, Jan. 29, 2000 (Abstract).
"Asymmetric synthesis of fluorinated L-tyrosine and meta-L-tyrosines," Michel Monclus, et al., Journal of Fluorine Chemistry, 70j (1995) 39-43.
"Positron emission tomography for evaluation of dopaminergic function using a neurotransmitter analog L-18F-m-tyrosine in monkey brain," SciFinder Scholar, Jan. 29, 2000 (Abstract).
"The noncatechol tracer 6-fluoro-m-tyrosine: Extrastriatal distribution of dopaminergic function," SciFinder Scholar, Jan. 29, 2000 (Abstract).
"Radioflurinated L-m-Tyrosines: New In-Vivo Probes for Central Dopamine Biochemistry," Jorge R. Barrio, et al., Journal of Cerebral Blood Flow and Metabolism, 16:667-678.
"6-[18F] Fluoro-L-m-tyrosine: metabolism, positron emission tomography kinetics, and 1-methyl-4-phenyl-1,2,3,6-tetrahydropyridine lesions in primates," Shaun Jordan, et al., Elsevier Science B.V., Brain Research 750 (1997) 264-276.
"Evaluation of Fluorinated m-Tyrosine Analogs as PET Imaging Agents of Dopamine Nerve Terminals: Comparision with 6-Fluorodopa," Onofre T. DeJesus, et al., The Journal of Nuclear Medicine, vol. 38, No. 4, Apr. 1997.

(Continued)

*Primary Examiner*—Elvis O. Price
(74) *Attorney, Agent, or Firm*—Barnes & Thornburg LLP

(57) ABSTRACT

Radiolabeled fluorinated compounds useful for imaging in the diagnosis of Parkinson's Disease are disclosed. Methods and kits for their synthesis are also disclosed.

15 Claims, 64 Drawing Sheets

OTHER PUBLICATIONS

"Affinites of Dopamine Analogs for Monoamine Granular and Plasma Membrane Transporters: Implicationos for PET Dopamine Studies," Christopher J. Endres, et al., Life Sciences, vol. 60, No. 26, pp. 2399-2406, 1997.

"A novel MPTP primate model of Parkinson's disease: neurochemical and clinical changes," Jamie L. Eberlind, et al., Elsevier Science B.V., Brain Research 805 (1998) 259-262.

"An In Vivo Microdialysis Study of Striatal 6-[18F] Flluoro-L-m-Tyrosine Metabolism," Shaun Jordan, et al. Neurochemical Research, vol. 23, No. 4, 1998, pp. 513-517.

"Evaluation of Dopaminergic Presynaptic Integrity: 6-[18F] Fluoro-L-Dopa Versus 6-{18F} Fluoro-L-m-Tyrosine, DJ Doudet, et al., Journal of Cerebral Blood Flow and Metabolism, 19:278-287.

"Localization of Trapping of 6-[18F] fluoro-L-m-tyrosine, an Aromatic L-Amino Acid Decarboxylase Tracer for PET," W. Douglas Brown, et al., SYNAPSE 34:111-123 (1999).

"Dopamine transporter loss and clinical changes in MPTP-lesioned primates," Jamie L. Eberling, Elsevier Science B.V., Brain Research 832 (1999) 184-187.

Evaluation of [F-18] Fluoro-m-tyrosine (FMT) Patient Studies; dosimetry and statistical considerations, T.E. Nordahl, et al., The Journal of Nuclear Medicine, vol. 39, No. 5, May 1998 Supplement, p. 190.

"Intracranial Hypotension with Parkinsonism, Ataxia, and Bulbar Weakness," S.I. Anthony, et al., Arch Neurol vol. 56, Jul. 1999, p. 869-872.

"The time course of metabolites in human plasma after 6-[18F] fluoro-L-m-tyrosine administration," Linda M. Wahl, European Journal of Nuclear Medicine, vol. 26, No. 11, Nov. 1999, pp. 1407-1412.

"Regions of Interest in the Venous Sinuses as Input Functions for Quantitative PET," Lindi M. Wahl, The Journal of Nuclear Medicine, vol. 40, No. 10, Oct. 1999.

"PET and Drug Research and Development," Joanna S. Fowler, et al., The Journal of Nuclear Medicine, vol. 40, No. 7, Jul. 1999, pp. 1154-1163.

"Imaging the functioning human brain," Xuchu Weng, et al., Proc. Natl. Acad. Sci. USA, vol. 96, pp. 11073-11074, Sep. 1999.

F-18 labeled biomolecules for PET studies in the neurosciences, Ding YS, Journal of Fluorine Chemistry, 101: (2) 291-295 Feb. 2000 (Abstract).

"Measurement of local cerebral glucose metabolism in man with 18F-2-fluoro-2-deoxy-D-glucose," M. Reivich, et al., Acta Neurol. Scand. 1977 56 (Suppl 64), pp. 190-191.

"Radiopharmaceuticals XXVII. 18F-Labeled 2-deoxy-2-fluoro-d-glucose as a Radiopharmaceutical for Measuring Regional Myocardinal Glucose Metabolism in vivo: Tissue Distribution and Imaging Studies in Animals.," BM Gallagher, Journal Nuclear Medicine, 1977, 18, 990-996.

"Synthesis of No-Carrier-Added Fluorine-18 2-fluoro-2-deoxy-d-glucose," Timothy J. Tewson, Journal Nucl Med. 24: 718-721, 1983.

"Efficient Stereospecific Synthesis of No-Carrier-Added 2-[18F]-Fluoro-2-Deoxy-D-Glucose Using Aminopolyether Supported Nucleophilic Substitution," K. Hamacher, et al., J Nucl Med 27:235-238, 1986.

"Neurochemical Imaging of Alzheimer's Disease and Other Degenerative Dementias," KA Frey, et al., J. Nuclear Med. 1998, 42, 166-178 (Abstract).

"Positron emission tomography with 18-F-fluorodeoxyglucose in the staging and follow-up of lymphoma: status quo and quo vadis," M. Bangerter, Onkologie Oct. 1999, 22, 382-386 (Abstract).

Metals Suitable for Fluorine Gas Target Bodies: First Use of Al;uminum for the Production of [18F]F2, Allyson Bishop, et al., Nuclear Med. Biol. 1996, 23, 181-188.

Proton Irradiation of [18O]02: Production of [18F]F2 and [18F]F2+[18F]OF2, Allyson Bishop et al., Nuclear Med. Biol. 1996, 23, 189-199.

"The Stereoselective Synthesis of Alpha-Amino-Acids by Phase-Transfer Catalysis," Martin J. O'Donnell, J. Am. Chem. Soc. 1989, 111, 2353-2355.

"A New Active Catalyst Species for Enantioselective Aklylation by Phase-Transfer Catalysis," Martin J. O'Donnell, et al., Tetrahedron 1994, 50,4507-4518.

"Amino Acid and Peptide Synthesis Using Phase-Transfer Catalysis," Martin J. O'Donnell, et al., ACS Symposium Series 659, American Chemical Society: Washington DC 1997, Chapter 10, pp. 124-135.

"A New Class of Asymmetric Phase-Transfer Catalysts Derived from Cinchona Alkaloids-Application in the Enantioselective Synthesis of alpha-Amino Acids," Barry Lygo, et al., Tetrahedron Lett. 1997, 38, 8595-8598.

"A Rational Approach to Catalytic Enantioselective Enolate Alkylation Using a Structurally Rigidified and Defined Chiral Quatemary Ammonium Salt Under Phase Transfer Conditions," EJ Corey, J. Am. Chemical Society 1997, 119, 12414-13415.

"Enantioselective Solid-Phase Synthesis of alpha-Amino Acid Derivatives," Martin J. O'Donnell, Tetrahedron 1999, 55, 6347-6362.

"2,2-Bis-trifluormethyl-oxazolidone-(5)," Friedrich Weygand, et al., Chem. Ber. 1966, 99, 1461-1469.

"Stereoconservative and Stereoselective Synthesis of Rare and Non-natural alpha-Amino Acidas from (S)-Aspartic Acid and (S)-Malic Acid," R. Pires, et al., Amino Acids 1996, 11, 301-312.

"Dopamine release from nigral transplants visualized in vivo and in a Parkinson's patient," Paola Piccini, et al., Nature Neuroscience, vol. 2 No. 12, Dec. 1999, pp. 1137-1140.

"Recent Developments in the Stereoselective Synthesis of a-Aminoacids," Rudolf O. Duthater, Tetrahedron 1994; 50(6): 1539-1650.

(4R,5S)-1,5-Dimethyl-4-phenylimidazolidin-2-one as a Chiral Auxiliary for the Diastereoselective Alkylation of a New Iminic Glycine Derivative: Practical Asymmetric Synthesis of alpha-Amino Acids, Gabriela Guillena, Tetrahedron: Asymm. 1998, 9, 1125-1129.

"Greatly Simplified Procedures for the Synthesis of alpha-Amino Acids by the Direct Alkylation of Pseudoephedrine Glycinamide Hydrate," Andrew G. Myers, et al., J. Org. Chem. 1999, 64,3322-3327.

"New Methodology for the Synthesis of a, a-Dialkylamino Acids using the "Self-Regeneration of Stereocenters" Method: a-Ethyl-a-phenylglycine," Martin J. O'Donnell, et al., Heterocycles 1997, 46, 617-630.

"Self-Regeration of Stereocenters (SRS)-Applications, Limitations, and Abandonment of a Synthetic Principle," Dieter Seebach, et al., Angew. Chem. Int. Ed. 1997, 35, 2708-2748.

"New chiral alanine template with a 1,2,3,6-tetrahydro-2-pyrazinone structure for the asymmetric synthesis of a-methyl a-amino acids," Tomas Abellan, et al., Tetrahedron: Asymm. 1998, 9,2211-2214.

"New PET Tracers for Cerebral Dopamine: Should 6-[18F]Fluoro-L-DOPA be Replaced? in Chemists' View of Imaging Centers," Gunter Firnau, et al., Emran, AM Ed., Plenum Press: New York, 1995, 237-382.

"A Molecular Map for Neurodegeneration," Kenneth Marek, et al., Science 2000, 289, 409-411.

"Initial Clinical Experience with 18F-Fluoro-M-tyrosine Positron Emission Tomography for the Investigation of Movement Disorders," SJ Skehan, Radiology 1999, 213P, 1569.

"A Probe for Intracerebral Aromatic Amino-Acid Decarboxylase Activity—Distribution and Kinetics of [F-18] 6-Fluoro-L-M—Tyrosine in the Human Brain," Nahmias, C. et al., Movement Disorders, 10: (3) 298-304 May 1995 (Abstract).

"An Efficient Homogeneous Catalytic Enantioselective Synthesis of α-Amino Acid Derivatives," M.J. O'Donnell et al., Tetrahedron Letters 39 (1998) 8775-8778.

"α-Amino Acid Synthesis," O'Donnell, M.J., Tetrahedron Symposia In Print No. 33, 1988, 44: 5253-5614.

"Synthesis of Optically Active α-Amino Acids," Williams, R.M., SciFinder Scholar (Abstract), Sep. 3, 2003 (Pergamon Press, Oxford, UK CAN 11:7917).

"How to build optically active -amino acids," M. Calmes et al., Amino Acids (1999) 16:215-250.

"Some of the amino acid chemistry going on in the Laboratory of Amino Acids, Peptides and Proteins," S. Bouifraden et al., Amino Acids (1999) 16:345-379.

"Glycine and Alanine Imine as Templates for Asymmetric Synthesis of α-Amino Acids," T. Abellan et al., Eur. J. Org. Chem., 2000, 2689-2697.

"Applications of aliphatic unsaturated non-proteinogenic α-H-α-amino acids," F. Rutjes et al., J. Chem. Soc., Perkin Trans. 1 2000, 4197-4212.

"The Preparation of Optically Active α-Amino Acids from the Benzophenone Iminies of Glycine Derivatives," M. O'Donnell, Aldrichimica Acta 2001, 34, 3-15.

"Asymmetric Synthesis of Novel Sterically Constrained Amino Acids—Symposium in Print," Hruby, Tetrahedron, 2001, 57, 6329-6650.

"The Synthesis of Amino Acid Derivatives by Catalytic Phase-Transfer Alkylations," M. O'Donnell, Tetrahedron Letters No. 47 (1978), pp. 4625-4628.

"A Mild and Efficient Route to Schiff Base Derivatives of Amino Acids," M. O'Donnell et al., J. Org. Chem., 1982, 47, 2663-2666.

"Enantiomeric enrichment of α-amino acid derivatives: recrystallization of N-Fmoc α-amino acid tert-butyl esters," M. O'Donnell et al., Tetrahedron 57 (2001( 6641-6650.

"Unnatural Amino Acid and Peptide Synthesis (UPS)," M. O'Donnell, Peptides 2000 (closing lecture at 26$^{th}$ European Peptide Symposium, Montpellier, France, Sep. 10-15, 2000).

"Asymmetric Synthesis of α-Amino-acid Derivatives by Alkylation of a Chiral Schiff Base," Shun-Ichi Yamada, J.C.S. Chem. Comm. 1976, pp. 136-137.

"Enantioselective Synthesis of (R)-Amino Acids Using L-Valine as Chiral Agent," U. Schollkopf et al., Verlag Chemie GmbH, Angew. Chem., Int. Ed. Engl., 1981, 20, pp.: 798-799.

"Asymmetric Synthesis Via Heterocyclic Intermediates-XXXIX. Asymmetric Synthesis of (Enantiomerically and Diasteriomerically Virtually Pure) Methyl-2-Amino-4,5-epoxy-3-hydroxy-alkanoates and Methyl 2-Amino-3-hydroxy-4,5-methylene-alkanoates by the Bislactimether Method," Tetrahedron 1988, 44, 5293-5305.

"The Chiral Glycine Enolate Derivative from 1-Benzoyl-2-(tert-butyl)-3-methyl-1,3-imidazolidin-4-one is Alkylated in the 5-Position with Relative Topicity lk," Hlv. Chim. Acta 1985, 68, 949-952.

"General Method of Diastereo- and Enantioselective Synthesis of β-Hydroxy-α-Amino Acids by Condensation of Aldehydes and Ketones with Glycine," Y. Belokon et al., J. Am. Chem. Soc. 1985, 107, 4252-4259.

"Large-scale asymmetric synthesis of novel sterically constrained 2',6'-dimetnyl- and α,2',6'-trimethyltyrosine and—phenylalanine derivatives via alkylatin of chiral equivalents of nucleophilic glycine and alanine," V. Soloshonok et al., Tetrahedron 57 (2001) 6375-6382.

"Electrophilic Glycinates: New and Versatile Templates for Asymmetric Amino Acid Synthesis," P. Sinclair, J. Am. Chem. Soc., 1986, 108, 1103-1104.

"Asymmetric Synthesis of Monosubstituted and α,α-Distributed α-Amino Acids via Diastereoselective Glycine Enolate Alkylations," R. Williams et al., J. Am. Chem. Soc., 1991, 113, 9276-9286.

"Asymmetric Synthesis of L-Diphenylalanine and L-9-Fluorenylglycine via Room Temperature Alkylations of a Sultam-Derived Glycine Imine," H. Josien et al., Tetrahedron Letters, vol. 32, No. 45, (1990) pp. 6547-6550.

"A Practical Method for the Synthesis of n- or L-α-Amino Acids by the Alkylation of (+)- or (−) Pseudoephedrine Glycinamide," A. Myers et al., J. Am. Chem. Soc., 1995, 117, 8488-8489.

"PTC and organic bases-LiCl assisted alkylation of imidzolidinone-glycine iminic derivatives for the asymmetric synthesis of α-amino acids," G. Guillena et al., Tetrahedron: Assymetri 9 (1998), 3935-3938.

"4-[$^{18}$F]Fluoroarylalkylethers via an improved synthesis of n.c.a. 4-[$^{18}$F]fluorophenol," T. Ludwig et al., Nuclear Medicine and Biology 29 (2002) 255-262.

"Convenient syntheses of 2-, 5- and 6-fluoro- and 2,6-difluoror-L-DOPA," W. Deng et al., Tetrahedron: Assymetry 13 (2002) 1135-1140.

"Enantioselective Amino Acid Synthesis by Chiral Phase-Transfer Catalysis," K. Maruoka et al., Chem. Rev. 2003, 103, 3013-3028.

* cited by examiner

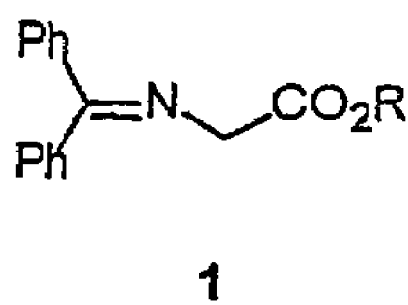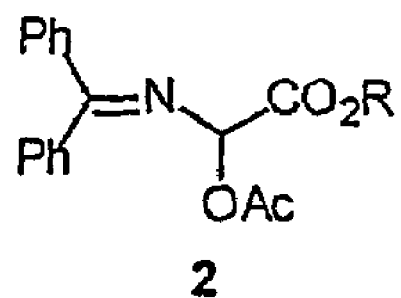
FIG. 4

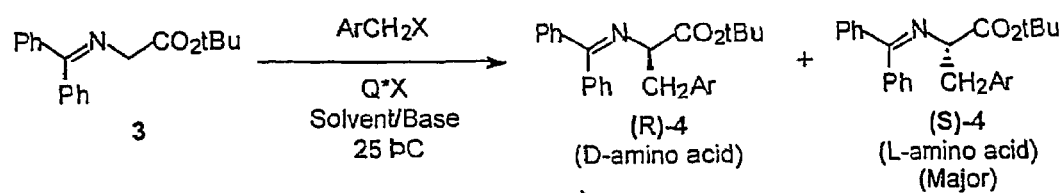
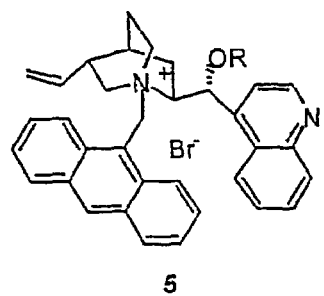
Cinchonidine-based PTC Catalyst
Solvent/Base = CH$_2$Cl$_2$/50% aq. NaOH
FIG. 5

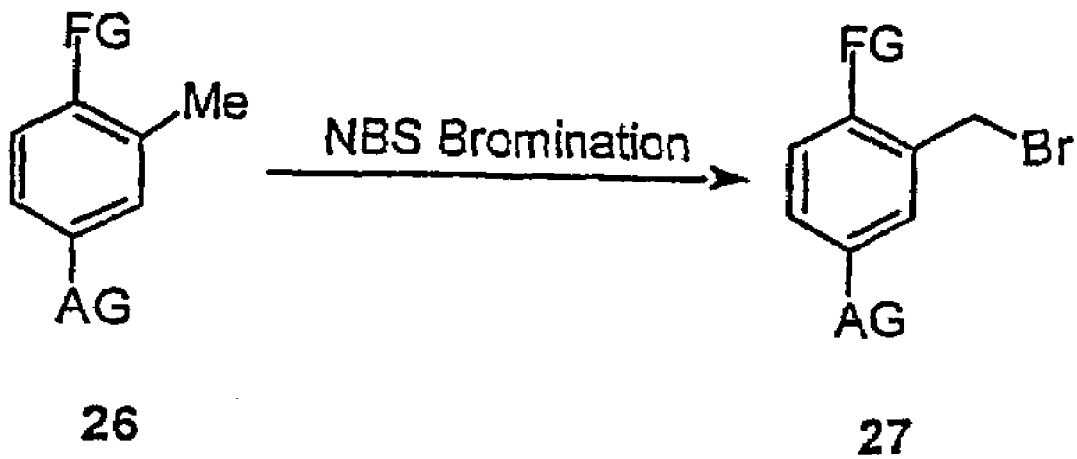
FG = NO₂, F, or NMe₂
AG = OMe, OAc,
or BTFMB =
FIG. 11

| Starting Material | Product | % Yield (Runs)[a] | Physical | mp(°C) |
|---|---|---|---|---|
| 28 | 29 | 47 (5) | yellow crystal | 64-65 |
| 30 | 31 | 36 (2) | yellow crystal | 56-57 |
| 17 | 32 | 41 (50) | yellow crystal | 78-79 |
| 10 | 33 | 0 (2) | | | a = 1.0 eq SM, 1.2 eq NBS

| Starting Material[a] | Product | NBS(eq) | Dibromohydantoin(eq) | % Yield (Runs) | mp(°C) |
|---|---|---|---|---|---|
| 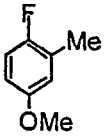 34 | 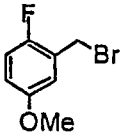 35 | 1.2-1.5 | – | 54 (7) | – |
|  |  | – | 0.55 | 90 (2) | – |
| 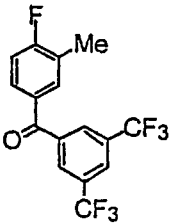 22 |  36 | 1.2 | – | 68 (8) | 90-92 |
| 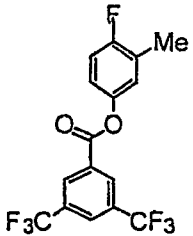 37 | 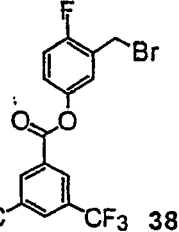 38 | 1.2 | – | 58 (12) | 66-68 |
a) 1.0 eq of starting material was used
FIG. 13

| Expt. | SM(eq) | NBS(eq) | %SM | %Product (Runs) | %Byproduct | Time(h) |
|---|---|---|---|---|---|---|
| 1 | 1.0 | 1.0 | 51 | 42 (2) | 7 | 5 |
| 2 | 1.0 | 1.2 | 57 | 41 (50) | 2 | 5 |
| 3[a] | 1.0 | 1.2 | 58 | 39 (2) | 3 | 5 |
| 4 | 1.0 | 2.0 | 45 | 49 (2) | 5 | 5 |
| 5 | 1.0 | 2.5 | 41 | 53 (2) | 7 | 5 |
| 6 | 1.0 | 3.0 | 8 | 66 (2) | 26 | 5 |
| 7 | 1.0 | 5.0 | 22 | 63 (2) | 15 | 5 |
| 8 | 1.0 | 1.2 | 41 | 46 (2) | 13 | 8 |
| 9 | 1.0 | 1.2 | 30 | 50 (2) | 20 | 10 | a) a second aliquot of benzoyl peroxide was added half-way through reaction

| Expt | SM(eq) | NBS(eq) | CCl₄(mL) | %SM | %Product (Runs) | %Byproduct | % Crude Yield |
|---|---|---|---|---|---|---|---|
| 1 | 1.0 | 1.2 | 0.5 | 57 | 41 (50) | 2 | 90 |
| 2 | 1.0 | 1.2 | 1.0 | 77 | 23 (2) | 0 | 96 |
| 3 | 1.0 | 1.2 | 2.0 | 95 | 5 (2) | 0 | 87 |
| 4 | 1.0 | 1.2 | 4.0 | 97 | 3 (2) | 0 | 88 |

| Procedure | Schiff Base(eq) | RX(eq) | % Product[a] | % RH | % Benzophenone | % Crude Yield |
|---|---|---|---|---|---|---|
| 1 | 1.05 | 1.0 | 83 | 6 | 11 | 90 |
| 2 | 1.0 | 1.0 | 97 | 3 | 0 | 108 |
| 3 | 1.0 | 1.0 | 80 | 7 | 13 | 110 | a) All procedures were ran at least twice.

| Procedure | Schiff Base(eq) | RX(eq) | Base/eq | Catalyst(eq) | CH$_2$Cl$_2$(mL) | Time(h) | %yield (runs) | %ee |
|---|---|---|---|---|---|---|---|---|
| 1 | 1.0 | 1.1 | BEMP/1.1 | 0.0 | 2.0 | 14 | 18 (4) | 0 |
| 2 | 1.0 | 1.1 | BEMP/1.1 | 0.1 | 2.0 | 14 | 11 (2) | 0.4 |
| 3 | 1.0 | 1.1 | BTPP/1.1 | 0.0 | 2.0 | 14 | 33 (2) | 0 |
| 4 | 1.0 | 1.1 | BTPP/1.1 | 0.1 | 2.0 | 18 | 49 (2) | 56 |
| 5 | 1.0 | 1.1 | BTPP/1.1 | 0.1 | 1.0 | 18 | 57 (12) | 80 |
| 6 | 1.0 | 1.1 | BEMP/1.1 | 0.0 | 2.0 | 24 | 25 (2) | 0 |
| 7 | 1.0 | 1.1 | BEMP/1.1 | 0.1 | 2.0 | 24 | 21 (2) | 2 |

| Product | Base(eq) | Schiff Base(eq) | Catalyst(eq) | Time(h) | Temp(ºC) | % Yield (Runs) |
|---|---|---|---|---|---|---|
| 50 | LiHMDS(1.2) | 1.0 | 0.0 | 12 | -78-RT | 49 (2) |
|  | BTPP(1.1) | 1.0 | 0.1 | 12 | -78 | 91 (5) |
| 51 | BTPP(1.0) | 1.0 | 0.1 | 12 | -78 | 42% (7) |

FIG. 21

| Starting Material | R | G | SM(eq) | CH$_2$O(eq) | Pd/C(eq) | H$_2$ (p.s.i.) | % Yield (Runs) | Product |
|---|---|---|---|---|---|---|---|---|
| 28 | Me | OMe | 1.0 | 6.25 | 0.01 | 55 | 59 (4) | 53 |
| 30 | Me | OAc | 1.0 | 4.17 | 0.01 | 55 | 84 (7) | 54 |
| 52 | CO$_2$tBu / NHBoc | BTFMB[a] | 1.0<br>1.0 | 7.52<br>3.00 | 0.06<br>0.10 | 55<br>55 | 0 (2)<br>12 (2) | 55 |

| Compound | R | EWG | SM(eq) | Pd/C(%/eq) | H₂ (atm) | % Crude Yield (Runs) | Product |
|---|---|---|---|---|---|---|---|
| 17 | Me | BTFMB | 1.0 | 5% / 0.05 | 1.0 | 101 (2) | 56 |
|   |   |   |   | 10% / 0.10 | 1.0 | 101 (8) | 56 |
| 52 | ⤳CO₂tBu / NHBoc | BTFMB | 1.0 | 10% / 0.10 | 1.0 | 102 (15) | 58 |

A) 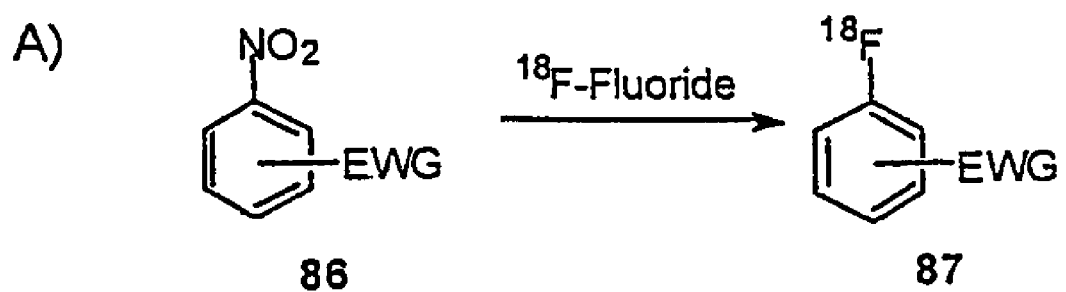
B) 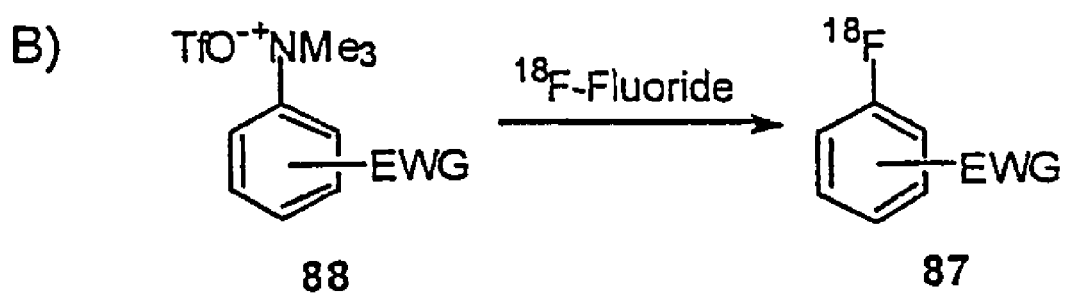
EWG (ortho or para) = 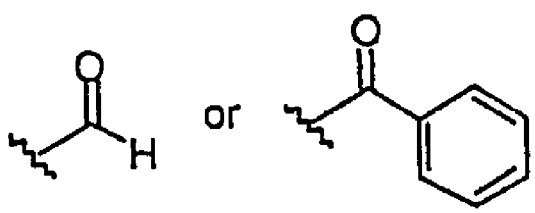
FIG. 33

| Trial | SM(eq) | MeOTf(eq) | Base(eq) | Solvent(mL) | Result[a] |
|---|---|---|---|---|---|
| 1 | 1.0 | 1.5 | – | CDCl$_3$(0.75) | no reaction |
| 2 | 1.0 | 277.0 | – | MeOTf(1.0) | decomposition |
| 3 | 1.0 | 1.5 | – | CD$_3$CN(0.75) | partial decomposition |
| 4 | 1.0 | 1.5 | DtBuMP(2.0) | CD$_3$CN(0.75) | partial decomposition |
| 5 | 1.0 | 1.5 | – | CH$_3$NO$_2$(0.75) | decomposition |
| 6 | 1.0 | 1.2 | DIEA(1.2) | CH$_2$Cl$_2$(2) | no reaction |
| 7 | 1.0 | 1.0 | DtBuMP(2.0) | CD$_3$NO$_2$(0.75) | decomposition |
| 8 | 1.0 | 1.0 | – | sulfolane(0.5) | decomposition |
| 9 | 1.0 | – | – | MeI(2.0) | no reaction | a) All trials were run twice.

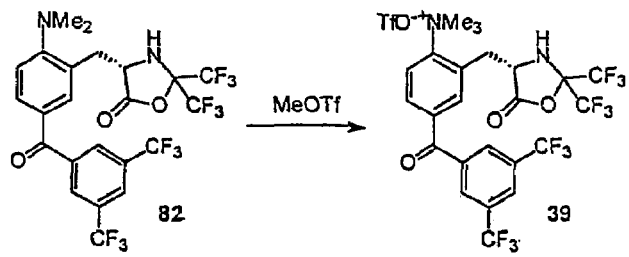

| Trial | MeOTf(eq) | Base | Solvent(mL) | Time(h) | Temp(ºC) | Result | % Yield (Runs) |
|---|---|---|---|---|---|---|---|
| 1 | 1.0 | – | CDCl₃(0.75) | 40 | RT | no reaction | 0 (1) |
| 2 | 1.0 | – | CD₃NO₂(0.75) | 12 | RT | decomposition | 0 (1) |
| 3 | 1.0 | DtBuMP(3.0) | CD₃NO₂(0.75) | 0.3 | RT | some product isolation difficulty | – (1)[a] |
| 4 | 1.0 | DtBuMP(3.0) | CD₃NO₂(0.75) | 13 | RT | decomposition | 0 (1) |
| 5 | 28.5 | DtBuMP(2.9) | – | 0.5 | RT | minor product | – (1)[b] |
| 6 | 28.5 | DtBuMP(2.9) | – | 1.0 | 70 | major product with H⁺-base; isolated white crystals | 80 (2) |
| 7 | 16.0 | DtBuMP(0.6) | – | 1.5 | 65 | major product with H⁺-base; isolated white crystals | 80 (6) | a) Unable to isolate product from mixture.
b) Analyzed crude mixture by ¹H-NMR and product was beginning to form.

FIG. 42A

| Starting Material | PG₁ | R | PG₂ | PG₃ | SM | MeOTf | Product | %Yield (Runs) |
|---|---|---|---|---|---|---|---|---|
| 53 | OMe | Me | – | – | 1.0 | 1.5 | 62 | 85 (2) |
| 54 | OAc | Me | – | – | 1.0 | 1.2 | 64 | 73 (6) |
| 9 | BTFMB | H | – | – | 1.0 | 2.0 | 66 | 78 (3) |
| 10 | BTFMB | Me | – | – | 1.0 | 2.0 | 89 | 96 (2) |
| 55 | BTFMB | AA | NHBoc | CO₂tBu | 1.0 | 1.0-1.5 | 80 | NR (9) |
| 82 | BTFMB | HFA | – | – | 1.0 | 16 | 39 | 80 (8) | a) decay-corrected radiochemical yield from end of bombardment a) decay-corrected radiochemical yield for reaction step

| Solvent System | Ketone ($R_f$) | Ester ($R_f$) | Δ ($R_f$) |
|---|---|---|---|
| 100% Hexane | 0.05 | 0.12 | 0.07 |
| 10:1 Hexane/EtOAc | 0.61 | 0.68 | 0.07 |
| 4:1 Hexane/EtOAc | 0.74 | 0.78 | 0.04 |
| 10:1 Hexane/$CH_2Cl_2$ | 0.26 | 0.36 | 0.10 |
| 5:1 Hexane/$CH_2Cl_2$ | 0.25 | 0.33 | 0.08 |
| 10:3 Hexane/$CH_2Cl_2$ | 0.31 | 0.41 | 0.10 |
| 1:1 Hexane/$CH_2Cl_2$ | 0.63 | 0.72 | 0.09 |
| 10:1:0.2 Hexane/$CH_2Cl_2$/IprOH | 0.56 | 0.65 | 0.06 |

FIG. 46

| Expt[a,b] | Temp (°C) | 15 min | 30 min | 40 min | 1.0 h | 1.2 h | 2.0 h | 2.5 h | 3.0 h |
|---|---|---|---|---|---|---|---|---|---|
| 1 | RT | 25% | 40% | – | 55% | | 66 % | >95% | ~100% |
| 2 | 50 | 33% | 70% | – | >95% | ~100% | – | – | – |
| 3 | 80 | 60% | >95% | ~100% | – | – | – | – | – | a) Estimated yields obtained by TLC analysis. b) All experiments were run twice.

a) decay-corrected radiochemical yield for reaction step

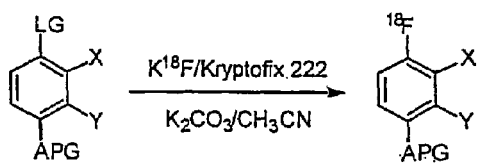

| Compound | LG | X | Y | APG | Radiochemical Yield (%)[c, d] |
|---|---|---|---|---|---|
| 110 | TfO⁻⁺NMe₃ | H | H | CO₂Et | 90[e, f] |
| 62 | TfO⁻⁺NMe₃ | Me | H | OMe | 0.3[f] |
| 64 | TfO⁻⁺NMe₃ | Me | H | OAc | 3.5[e] |
| 66 | TfO⁻⁺NMe₃ | H | H | ⟅C(O)-3,5-(CF₃)₂C₆H₃⟆ | 81[f] |
| 89 | TfO⁻⁺NMe₃ | Me | H | ⟅C(O)-3,5-(CF₃)₂C₆H₃⟆ | 65[f] |
| 111 | TfO⁻⁺NMe₃ | H | Me | -N=N-Ph | 0.6[f] |
| 17 | NO₂ | Me | H | ⟅C(O)-3,5-(CF₃)₂C₆H₃⟆ | 11[f] |
| 112 | NO₂ | Me | H | OTs | 0[g] |
| 113 | TfO⁻⁺N₂ | OMe | H | Cl | 4[e] |
| 114[h] | TfO | H | H | NO₂ | 3.6[f] |
| 115[h] | TfO | H | H | Ac | 3.6[f] | a) LG = leaving group b) APG = activated protecting group c) decay-corrected values d) All experiments were run at least twice. e) solid-phase synthesis f) solution-phase synthesis g) Ts–¹⁸F was made h) commercially available compound.

FIG. 52

| Compound | Starting Activity (mCi) | Inorganic Fluoride (mCi) | Radiolabeled Product (mCi) | % Corrected Yield (eob)[a] |
|---|---|---|---|---|
| 49 | 9.76 | 7.22 | 0.2 | 2 |
| 52 | 10.10 | 4.74 | 2.55 | 25 |
| 69 | 9.61 | 5.68 | 1.74 | 18 |
| 17 | 15.03 | 10.69 | 1.64 | 11 |
| 77 | 12.76 | 7.54 | 0.4 | 3 |
| 116 | 9.42 | 7.13 | 0 | 0 | a) All experiments were run twice.

| Compound | HPLC System 1 | HPLC System 2 | HPLC System 3 |
|---|---|---|---|
| Tyr | – | – | 4.89 |
| m-Tyr | – | – | 5.72 |
| 85 | 3.18 | – | 6.25 |
| Phe | – | – | 8.34 |
| 103 | – | 11.84 | – |
| 79 | 4.34 | 18.34 | – |
| 95 | 19.30 | – | – |
| 108 | – | 25.93 | – |

HPLC System 1 = 2:2:1 $CH_3CN$/MeOH/20 mM $NaH_2PO_4$, 1.0 ml/min, 220 nm
HPLC System 2 = 1:1:2 $CH_3CN$/MeOH/20 mM $NaH_2PO_4$, 1.0 ml/min, 220 nm
HPLC System 3 = 83.5% 20 mM $NaH_2PO_4$/16.5% MeOH, 1.0 ml/min, 272 nm

FIG. 57

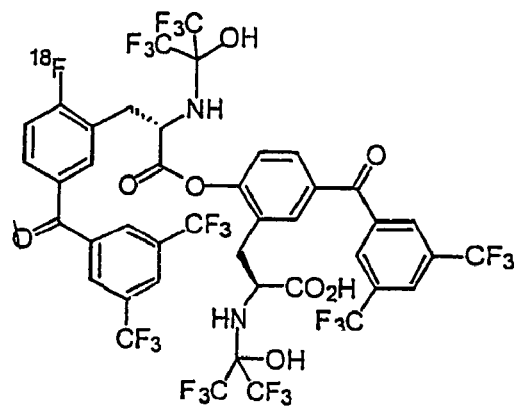
124
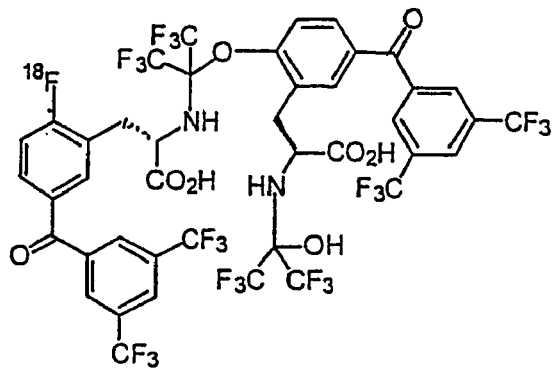
125
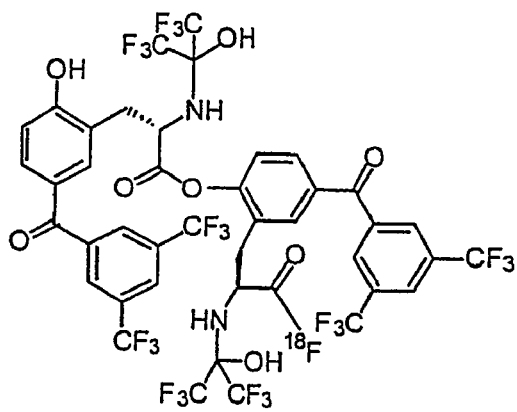
126
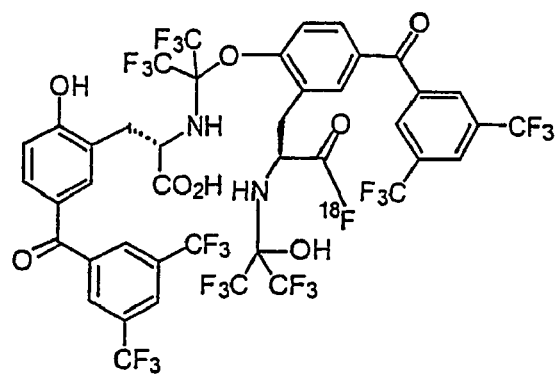
127
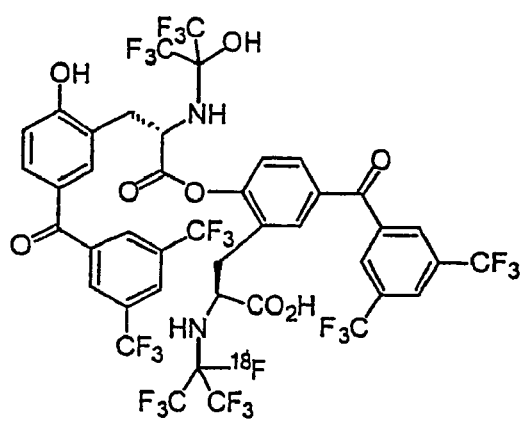
128
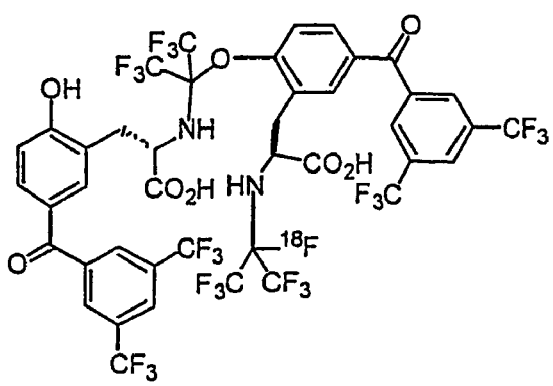
129
FIG. 59

Scheme 3.2

NUCLEOPHILIC APPROACH FOR PREPARING RADIOLABELED IMAGING AGENTS AND ASSOCIATED COMPOUNDS

CROSS-REFERENCE TO RELATED APPLICATIONS

This application is a U.S. national counterpart application of international application serial no. PCT/US01/45685 filed Nov. 30, 2001, which claims the benefit of United States provisional application Ser. No. 60/250,111 filed Nov. 30, 2000.

GOVERNMENT RIGHTS

This invention was made with support of funds provided under Grants Nos. RO1 GM28193 and P50 HL52323 awarded by the National Institutes of Health. The United States Government has certain rights in the invention.

BACKGROUND OF THE INVENTION

The present invention generally relates to a nucleophilic approach for preparing radiolabeled imaging agents. The present invention particularly relates to a nucleophilic approach for preparing radiofluorinated imaging agents which are utilzed in Positron Emission Tomography.

It is estimated there are currently 2–4 million victims of Parkinson's disease (PD) in the United States today. Parkinson's is a progressive irreversible neurodegenerative disease characterized by a loss of the pigmented, dopaminergic neurons of the substantia nigra pars compacta, with the appearance of intracellular inclusions known as Lewy bodies. The disease usually strikes during the later years of life, but a significant portion of PD victims develop debilitating symptoms in their highly productive forties or even thirties.

Victims of Parkinson's can present with bradykinesia (slowness and poverty of movement), muscular rigidity, resting tremor (which usually abates during voluntary movement), and an impairment of postural balance leading to disturbances of gait and falling. Without treatment, PD progresses over 5 to 10 years to a rigid, akinetic state in which patients are incapable of caring for themselves. Death frequently results from complications of immobility, including aspiration pneumonia or pulmonary embolism.

Because of its long duration of morbidity (patients usually live 20 years or more under care following onset of symptoms) PD is a disease with major economic and public health impacts in the developed world. The seriousness of this problem is projected to grow over the next 30 years with the approaching demographic bulge of elderly baby-boomers and increase in average age in the populations of North America, Western Europe, and Japan. However, the availability of effective pharmacological treatment has altered radically the prognosis of PD; and in most cases, good functional mobility can be maintained for many years, and the life expectancy of adequately treated patients is substantially increased.

However, in order to optimize the aforementioned pharmacological treatment an early detection and diagnosis of PD must be made. This is particularly evident in light of the fact that current clinical diagnosis, based on PD symptomatology, can only be made after approximately 90% of neurological function in the brain's nigrostriatal dopamine pathway has been lost.

With respect to the early detection and diagnosis of PD, two fluorine-18 labeled tyrosine derivatives, 6-fluoro-dopa (FDOPA) and 6-fluoro-meta-tyrosine (6-FMT), have been demonstrated to be useful PET (positron emission tomography) radiopharmaceuticals for the early diagnosis and study Of PD and related movement disorders in humans. However, there are drawbacks to utilizing the aforementioned fluorine-18 tracers. For example, the fluorine-18 radioisotope only has a two hour halflife and therefore these tracers are typically produced in special cyclotron-PET facilities, and used on-site or within a fairly local distribution radius. In addition, the existing synthetic methods for producing these fluorine-18 tracers are non-routine and commercially unfeasible. As a result of these drawbacks, only a handful of research facilities in the world possess the special equipment or expertise that is currently required to manufacture FDOPA and 6-FMT. Therefore, the clinical use of FDOPA and/or 6-FMT has been limited to perhaps only seven sites in the world at present, i.e. University of Wisconsin, University of California at Berkeley, University of California at Los Angeles, University of British Columbia (Canada), McMaster University (Canada), Universite Libre de Bruxelles (Belgium), and Gunma University (Japan). The limited number of facilities which can clinically utilize FDOPA and/or 6-FMT tracers severely constrains the access PD victims have to these diagnostic tools.

Therefore, in light of the above discussion, it is apparent that what is needed is an approach for preparing radiolabeled imaging agents and associated compounds that addresses one or more of the above discussed drawbacks.

SUMMARY OF THE INVENTION

In accordance with one embodiment of the present invention, there is provided a compound having the formula:

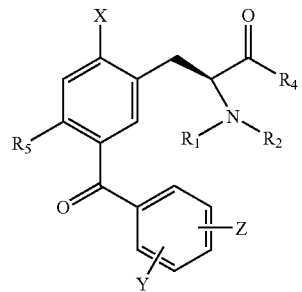

wherein $R_1$ is hydrogen, halomethyl, acyloxymethyl of 1–4 carbons, formyl, acyl, polyfluoroacyl of 2–3 carbons, sulfonyl or phosphoryl, such that $R_1$ is readily converted to hydrogen upon treatment with acid or aqueous base, or $R_1$ together with $R_4$ and —N—$C_\alpha$—C(O)— forms a 4–7 membered ring, with bridging atoms being C, O, N, P, or S, or combinations thereof, such that $R_4$ is readily converted to OH upon treatment with acid, aqueous base or oxidizing conditions; $R_2$ is hydrogen, $C_2$–$C_7$ normal, branched, cyclic saturated, cyclic unsaturated alkyl and alkoxyalkyl, optionally substituted tert-butyloxycarbonyl, optionally substituted benzyloxycarbonyl, formyl, acyl, polyfluoroacyl of 2–3 carbons, sulfonyl or phosphoryl, such that $R_2$ is readily converted to hydrogen upon treatment with acid or aqueous base; $R_4$ is OtBu, OCH$_3$, $C_2$–$C_7$ normal, branched, cyclic saturated, or cyclic unsaturated alkoxy, or $R_4$ together with $R_1$ and —N—$C_\alpha$—C(O)— forms a 4–7 membered ring, with bridging atoms being C, O, N, P, or S, or combinations thereof, such that $R_4$ is readily converted to OH upon treatment with acid, aqueous base or oxidizing conditions; X is halogen, $NO_2$, $N_2^+$, $N^+(CH_3)_3$, $S^+(CH_3)_2$, or aryl iodonium; Y is hydrogen, fluorinated alkyl, or $NO_2$; Z is fluorinated alkyl or $NO_2$; and $R_5$ is hydrogen, OtBu, $OCH_3$, $C_2$–$C_7$ normal, branched, cyclic saturated, or cyclic unsaturated alkoxy, acyl, halogen, azide or acylamide.

In accordance with another embodiment of the present invention there is provided a compound having the formula:

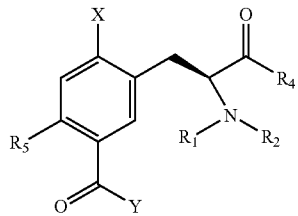

wherein X is a leaving group which allows nucleophilic radiofluorination at the position of X in the presence of soluble reactive [$^{18}$F]fluoride ion; Y is a radical which contains one or more electron-withdrawing groups that result in an oxygen directly attached to the aromatic ring para to leaving group X when the compound is subjected to a Baeyer-Villiger Reaction; $R_1$ is hydrogen, halomethyl, acyloxymethyl of 1–4 carbons, formyl, acyl, polyfluoroacyl of 2–3 carbons, sulfonyl or phosphoryl, such that $R_1$ is readily converted to hydrogen upon treatment with acid or aqueous base, or $R_1$ together with $R_4$ and —N—$C_\alpha$—C(O)— forms a 4–7 membered ring, with bridging atoms being C, O, N, P, or S, or combinations thereof, such that $R_4$ is readily converted to OH upon treatment with acid, aqueous base or oxidizing conditions; $R_2$ is hydrogen, $C_2$–$C_7$ normal, branched, cyclic saturated, cyclic unsaturated alkyl and alkoxyalkyl, optionally substituted tert-butyloxycarbonyl, optionally substituted benzyloxycarbonyl, formyl, acyl, polyfluoroacyl of 2–3 carbons, sulfonyl or phosphoryl, such that $R_2$ is readily converted to hydrogen upon treatment with acid or aqueous base; $R_4$ is OtBu, $OCH_3$, $C_2$–$C_7$ normal, branched, cyclic saturated or cyclic unsaturated alkoxy, or $R_4$ together with $R_1$ and —N—$C_\alpha$—C(O)— forms a 4–7 membered ring, with bridging atoms being C, O, N, P, or S, or combinations thereof, such that $R_4$ is readily converted to OH upon treatment with acid, aqueous base or oxidizing conditions; and $R_5$ is hydrogen or a radical that can be converted to a phenolic OH group during or after the Baeyer-Villiger Reaction.

In accordance with yet another embodiment of the present invention there is provided a kit for providing a radiolabeled Positron Emission Tomography imaging agent. The kit includes a first container which contains a compound having the formula;

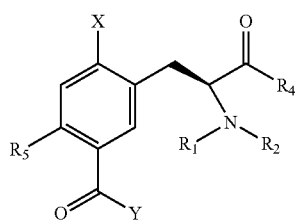

wherein X is a leaving group which allows nucleophilic radiofluorination at the position of X in the presence of soluble reactive [$^{18}$F]fluoride ion; Y is a radical which contains one or more electron-withdrawing groups that result in an oxygen directly attached to the aromatic ring para to leaving group X when the compound is subjected to a Baeyer-Villiger Reaction; $R_1$ is hydrogen, halomethyl, acyloxymethyl of 1–4 carbons, formyl, acyl, polyfluoroacyl of 2–3 carbons, sulfonyl or phosphoryl, such that $R_1$ is readily converted to hydrogen upon treatment with acid or aqueous base, or $R_1$ together with $R_4$ and —N—$C_\alpha$—C(O)— forms a 4–7 membered ring, with bridging atoms being C, O, N, P, or S, or combinations thereof, such that $R_4$ is readily converted to OH upon treatment with acid, aqueous base or oxidizing conditions; $R_2$ is hydrogen, $C_2$–$C_7$ normal, branched, cyclic saturated, cyclic unsaturated alkyl and alkoxyalkyl, optionally substituted tert-butyloxycarbonyl, optionally substituted benzyloxycarbonyl, formyl, acyl, polyfluoroacyl of 2–3 carbons, sulfonyl or phosphoryl, such that $R_2$ is readily converted to hydrogen upon treatment with acid or aqueous base; $R_4$ is OtBu, $OCH_3$, $C_2$–$C_7$ normal, branched, cyclic saturated, or cyclic unsaturated atkoxy, or $R_4$ together with $R_1$ and —N—$C_\alpha$—C(O)— forms a 4–7 membered ring, with bridging atoms being C, O, N, P, or S, or combinations thereof, such that $R_4$ is readily converted to OH upon treatment with acid, aqueous base or oxidizing conditions; $R_5$ is hydrogen or a radical that can be converted to a phenolic OH group during or after the Baeyer-Villiger Reaction; and a second container which contains a polar aprotic solvent for dissolving said compound.

It is therefore an object of the present invention to provide a new and useful approach for preparing radiolabeled imaging agents and associated compounds.

It is another object of the present invention to provide an improved approach for preparing radiolabeled imaging agents and associated compounds.

It is still another object of the present invention to provide a new and useful kit for providing a radiolabeled Positron Emission Tomography imaging agent.

It is another object of the present invention to provide an improved kit for providing a radiolabeled Positron Emission Tomography imaging agent.

The above and other objects, features, and advantages of the present invention will become apparent from the following description and attached drawings.

BRIEF DESCRIPTION OF THE DRAWINGS

FIG. 4 depicts anionic 1 and cationic 2 glycine equivalents;

FIG. 5 illustrates stereoselective synthesis of α-amino acids via PTC;

FIG. 11 illustrates NBS Bromination of toluene derivatives;

FIG. 13 illustrates NBS Bromination of fluorine derivatives;

FIG. 21 illustrates products 50 and 51 prepared by alkylation of 3;

FIG. 33 depicts $^{18}$F-Fluorodenitration (A) and radiofluorination method (B);

FIG. 42A depicts the the methylation of Hexafluoroacetone-Protected compound 82;

FIG. 46 illustrates optimization of TLC systems for the separation of starting material ketone 25 and product ester 104;

FIG. 52 illustrates nucleophilic radioflurination of various substrates;

FIG. 57 shows HPLC data for the reference compounds of FIG. 56;

FIG. 59 illustrates possible radiofluorinated dimers derived from 39;

DETAILED DESCRIPTION OF THE PREFERRED EMBODIMENT

Figure 1:
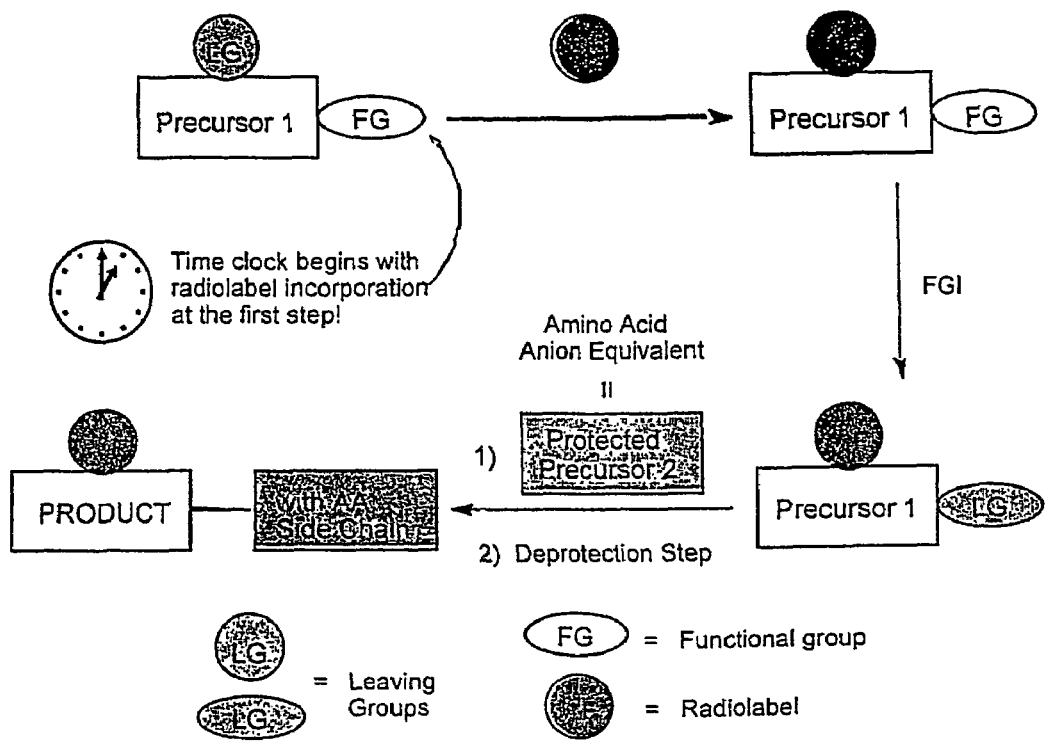
FIG. 1. is a schematic representation of a radiosynthetic pathway which introduces a label at an early stage in the chemical synthesis.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Radiotracer Design Process

Three steps were followed for choosing a compound that can be used to study a biological process. First, the biological or medical problem needs to be identified. Second, an appropriate tracer candidate is selected after its interaction in vivo has been elucidated and the target site, where the radiotracer is localized and detected by PET, is known. Also, the biodistribution of the tracer to the target site needs to be significantly higher than to the rest of the body to provide a contrast for imaging. Lastly, a radiolabel is selected from four commonly-used positron emitters (carbon-11, fluorine-18, nitrogen-13, oxygen-15) and this isotope is incorporated into the desired tracer candidate (see Table 1 below). The position of the radiolabel incorporation must not alter the biological behavior of the radiotracer, which must retain the desired characteristics of the parent molecule. These isotopes are ideally suited for exploring many aspects of human physiology and biochemistry because they have short half-lives, body penetrating. (gamma, γ-) radiation resulting from positron decay, and they allow for high specific activity.

TABLE 1

Common Positron-emitting PET Isotopes.

| Radioisotope | $t_{1/2}$ | Nuclear reaction |
| --- | --- | --- |
| $^{15}$O | 2.05 min | $^{15}$N(p, n)$^{15}$O |
| $^{13}$N | 10.0 min | $^{16}$O(p, α)$^{13}$N |
| $^{11}$C | 20.4 min | $^{14}$N(p, α)$^{11}$C |
| $^{18}$F | 109.6 min | $^{18}$O(p, n)$^{18}$F |

Once the radioisotope is produced for radiochemistry purposes, the time clock starts and the radiochemist/radiopharmacist team has roughly 2 hours, if using [$^{18}$F]fluoride, to work with the activity before half of it decays away. The radiolabel is incorporated into the molecule and the quality of the radiotracer is certified "safe for human consumption" according to FDA standards. After these tasks are completed, the dose is given to a patient and a PET scanner subsequently generates a computed three-dimensional image from the detected positron annihilations. The image produced can ultimately give a physician useful information to plan any necessary treatments for the patient.

Synthetic Strategy

Radiosynthetic strategies were designed according to the isotope choice and with the idea that introduction of the radiolabel should occur in the ultimate or pentultimate step of the synthesis. There are several reasons for using [$^{18}$F]fluoride in the reactions of the present invention over the conventional cyclotron-produced radioisotopes. These include (i) [$^{18}$F]Fluoride, due to its compact size, is an excellent bioisostere for hydrogen and is metabolically stable once it has been incoporated into a molecule and (ii) [$^{18}$F]fluoride also has the longest half-life among the common positron-emitting labels and will be the most appropriate to use in a clinical PET setting. However, it should be understood that the 110 min half-life is hardly enough time to incorporate the fluorine into a structurally simple molecule and then build the rest of the molecule around the decaying fluorinated product which is a problem addressed by the present invention. In particular, a precursor of the present invention is stable at room temperature and can be stored for a significant period of time until its use for making the desired radiopharmaceutical.

Furthermore, the precursor has a good leaving group, such as aryl azide, $N_2^+$ triazene, nitro, or trimethylammonium trifluoromethanesulfonate, dimethyl sulfanylonium trifluororaryliodonium for displacement by the incoming [$^{18}$F] fluoride. Moreover, reaction steps of the present invention, including and after radiolabel incorporation, are fast and compatible with the short half-life of the radionuclide. In addition, the final route of the present invention is designed with radiotracer fate and required specific activity (i.e. carrier-free, no-carrier added, carrier-added) considerations in mind.

Current Electrophilic Versus Desired Nucleophilc Radiofluorination Routes

Earlier approaches to make [$^{18}$F]-labeled radiopharmaceuticals have employed one of two different radiosynthetic methods, electrophilic or nucleophilc fluorination. Electrophilic fluorination, the more popular method for making aromatic C-F bonds, typically uses an electrophilic reagent such as [$^{18}$F]-acetyl hypofluorite or [$^{18}$F]F$_2$ fluorine gas to either directly label a precursor or fluorodemetallate an organometallic precursor, which involves metals such as mercury and tin. Although fluorodemetallation is the more commonly used technique due to its regiospecific nature and ability to provide higher yields, this technique requires additional steps of precaution and quality assurance that complicate the overall manufacturing process when these toxic metals are used.

In general, the electrophilic methods have other limitations and disadvantages that make them less attractive. Since electrophilic fluorine is extremely reactive, radiochemical yields are usually quite low due to radiofluorine decomposition or side reactions with the surface of the reaction apparatus, transfer tubing, and other components than the precursor. Another disadvantage is that electrophilic methods require the addition of non-radioisotopic carrier fluorine in the labeling process to reduce the specific activity of the final radiotracer. The dilution of the desired radiotracer with the non-radioisotopic form effectively increases the drug quantity in the tracer dose but cuts the radiolabeling efficiency by 50% and increases the potential for an undesired pharmacological effect during an imaging study.

Constrained to the limitations of a newer and less expensive "proton only" medical cyclotron, many facilities cannot carry out the nuclear reaction most widely used for making electrophilic [$^{18}$F]-F$_2$ gas. The Ne-20(d, alpha)F-18 reaction has a low cross section (yield) and requires a cyclotron that accelerates deuterons and not protons. Recent efforts to apply the more efficient O-18(p, n)F-18 nuclear reaction to refined gas targets have been successful in providing electrophilic F-18. However, these unfamiliar and relatively few targets in the field are still not likely to attract the broader PET community due to the difficult electrophilic chemistries mentioned above compared to the more conventional nucleophilic route used to make present routine tracers such as 2-[$^{18}$F]fluorodeoxyglucose (FDG).

Figure 2:
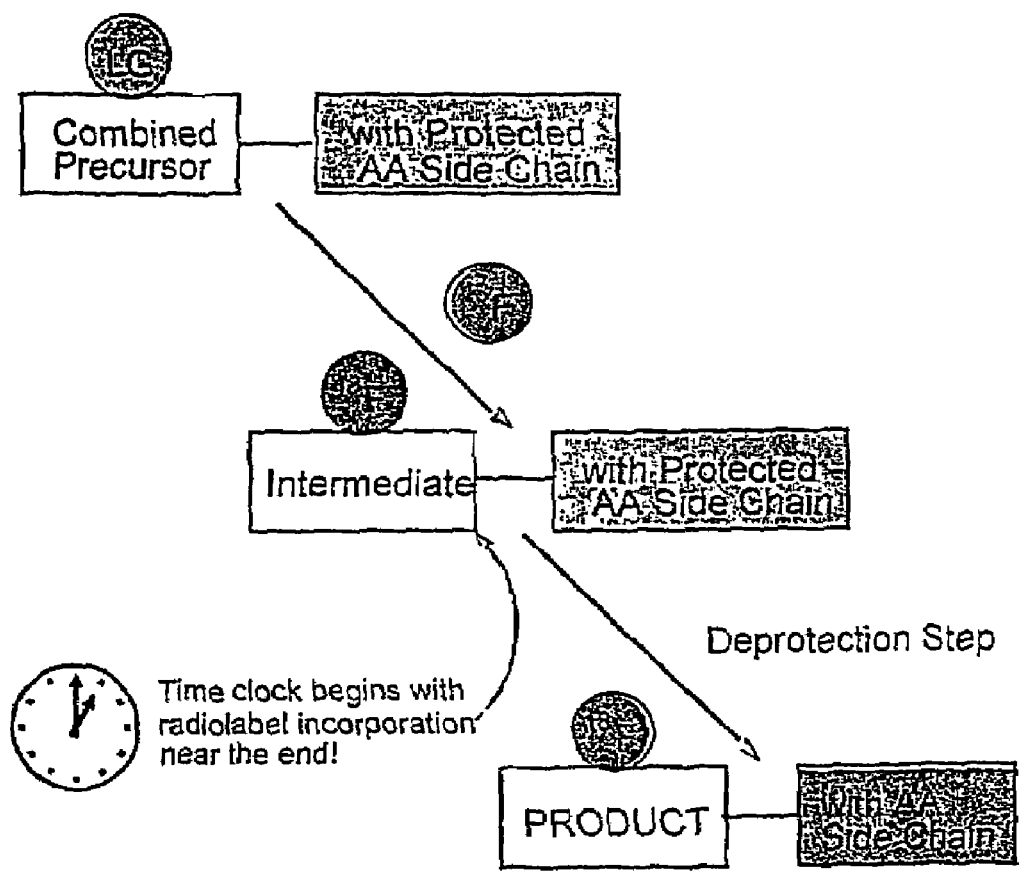
FIG. 2 is a schematic representation of a radiosynthetic pathway which introduces a label at a penultimate step in the chemical synthesis.

Nucleophilic radiofluorination has been successfully used for making fluorophenylalanine derivatives. Unfortunately, these radiosynthetic pathways introduce the label at a very early stage in the chemical synthesis and then manipulate the radiolabeled precursor through several steps before isolating the final product in rather low yield (see FIG. 1). This method requires several highly skilled individuals working in coordination and is impractical for automation and widespread use. The radiosynthetic strategy of the present invention has the nucleophilic radiofluorination occurring at the ultimate or penultimate step followed by one or two rapid steps to give the final radiotracer (see FIG. 2).

Amino Acid Side Chain Synthesis Using Schiff Base Synthons

α-Amino acids play an integral role in many biological systems. Proteins are built from a combination of twenty amino acids. The structural arrangement of four different groups about the α-carbon confers optical activity on amino acids; thus, most amino acids can have two enantiomeric forms. In many cases, the two enantiomers will elicit different biological responses. One enantiomer may prove to be a useful therapeutic pharmaceutical while the other may not. Hence, an efficient and reliable technique is required to synthesize and isolate the desired optically pure amino acid. One method of obtaining enantiomerically pure materials is by asymmetric synthesis, more specifically, asymmetric phase-transfer reactions (see M. J. O'Donnell in Catalytic Asymmetric Synthesis, I. Ojima, Ed., Wiley: New York, 2000, Chapter 10, 727, incorporated herein by reference).

Figure 3:
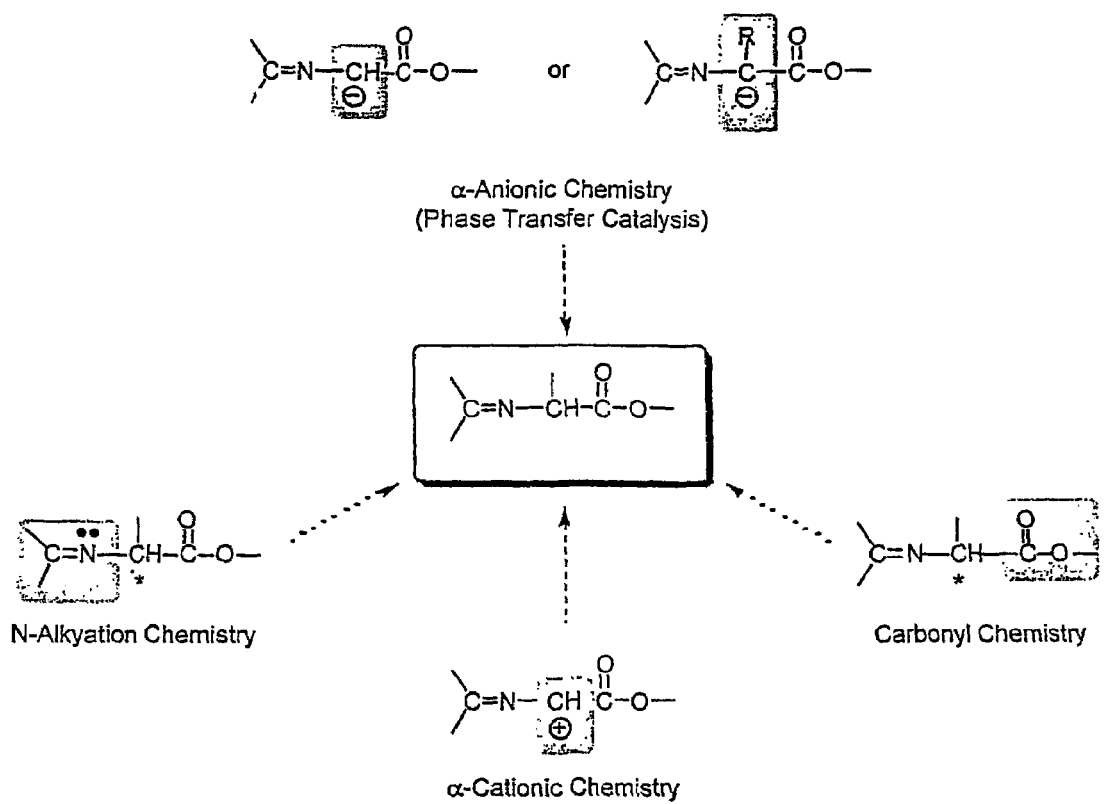
FIG. 3 depicts four ways of modifying the structural subunit (1) for the Synthesis of α-Amino Acid Derivatives: 1) α-Anionic, 2) α-Cationic, 3) Carbonyl, and 4) N-Alkylation Chemistry.

The acyclic structural subunit shown in FIG. 3 can be used for the synthesis of α-amino acid derivatives (see M. J. O'Donnell; S. Wu; J. C. Huffman, Tetrahedron, 1994, 50, 4507, incorporated herein by reference). The generation of carbon-carbon, carbon-nitrogen, and carbon-oxygen bonds can be accomplished via different methodologies. Carbon-carbon bond construction involves either anionic (1) or cationic (2) amino acid equivalents. For example, Schiff-base protected glycine derivatives (see FIG. 4), are frequently used to synthesize a variety of useful amino acid derivatives and many synthetic pathways have evolved from both α-ionic glycine derivatives (see M. J. O'Donnell; R. L. Polt, J. Org. Chem. 1982, 47, 2663, incorporated herein by reference).

Cationic Amino Acid Equivalents

The α-cationic synthon is an excellent electrophile that can react with many nucleophiles to give a diverse array of amino acid compounds. The neutral acetate derivative, for instance, was made by subjecting the benzophenone imine of glycine ethyl ester to bromination in the presence of acetate. The electrophilic acetate has diverse functionalities which provides various reactivity and selectivity patterns (see M. J. O'Donnell; W. D. Bennett; R. L. Polt, Tetrahedron Lett. 1985, 26, 695 and R. M. Williams; W. Zhai, Tetrahedron 1988, 44, 5425 both of which are incorporated herein by reference). A promising new synthetic route based on palladium-catalyzed coupling of the acetate to various nucleophiles has been reported (see M. J. O'Donnell; N. Chen; C. Zhou; A. Murray; C. P. Kubiak; F. Yang; G. G. Stanley, J. Org. Chem., 1997, 62, 3962, incorporated herein by reference) Palladium is useful because it provides the ability to control the stereoselectivity of the reaction. With this control of stereoselectivity, the reaction between the nucleophile and the electrophilic acetate can yield optically active α-amino acids in high enantiomeric excess (see G. Consiglio; R. M. Waymouth, Chem. Rev., 1989, 89, 257, incorporated herein by reference).

Anionic Amino Acid Equivalents

The α-anionic synthon can serve as a nucleophilic substrate in a phase-transfer catalyzed reaction (see G. Consiglio; R. M. Waymouth, Chem. Rev., 1989, 89, 257, incorporated herein by reference). A useful synthetic methodology has been developed for making α-monoalkylated products. This method employs catalytic phase transfer alkylations of the benzophenone imine of glycine alkyl esters and other glycine derivatives. Aldimine derivatives serve as simple precursors to α-dialkylated amino acids from the protected monoalkyl derivative. Complementarity of these two types of substrates is attributed to the different α-proton acidities (see M. J. O'Donnell; W. D. Bennett; W. N. Bruder; K. K. Jacobsen; B. LeClef; R. L. Polt; F. G. Bordwell.; S. R. Mrozack; T. A. Cripe, J. Am. Chem. Soc., 1988, 110, 8520, incorporated herein by reference).

Asymmetric Amino Acid Synthesis with a Chiral, Non-Racemic Catalyst

A practical asymmetric synthesis of α-amino acids using PTC is described in M. J. O'Donnell; W. D. Bennett; S. Wu, J. Am. Chem. Soc., 1989, 111, 2353, which is incorporated herein by reference. With a chiral catalyst and a prochiral Schiff-base protected glycine equivalent, PTC alkylation provides a means of preparing optically active α-amino acids as shown in FIG. 5 (see U.S. Pat. No. 5,554,753 which is incorporated herein by reference).

Once the desired optically enriched product is generated (normally at levels of ≧80% ee), it is necessary to isolate the enantiomerically pure product. Several methods can be utilized: (i) Crystallization of the racemate often provides optically enriched filtrates from which the pure enantiomer can be obtained; (ii) resolution of diastereomeric salts, or (iii) enzymatic resolution of derivatives.

In addition, catalysts derived from the cinchona alkaloids can be utilized (see E. J. Corey; F. Xu; M. C. Noe, J. Am. Chem. Soc., 1997, 119, 12414 and B. Lygo; P. G. Wainwright, Tetrahedron Lett., 1997, 38, 8595, both of which are incorporated herein by reference). Introduction of the 9-anthracenylmethyl group in 5 in place of the original benzyl group can increase enantioselectivity.

UPS Chemistry

Solid-phase methodologies utilizing the Schiff base imines of amino acids, termed unnatural amino acid and peptide synthesis (UPS) allows for the introduction of the amino acid side chain during a normal solid-phase peptide synthesis (SPPS) (see M. J. O'Donnell; C. Zhou; W. L. Scott, J. Am. Chem. Soc., 1996, 118, 6070; W. L. Scott; C. Zhou; Z. Fang; M. J. O'Donnell, Tetrahedron Left., 1997, 38, 3695; E. Dominguez; M. J. O'Donnell; W. L. Scott, Tetrahedron Left., 1998 39, 2167; M. J. O'Donnell; F. Delgado; R. S. Pottorf, Tetrahedron, 1999, 55, 6347; and M. J. O'Donnell; M. D. Drew; R. S. Poftorf; W. L. Scott, J. Comb. Chem., 2000, 2, 172, all of which are incorporated herein by reference). A number of chemical varients have been reported and enantioselective PTC-type alkylations on solid-phase have also been realized.

Proposed Synthesis of 6-[$^{18}$F]Fluoro-meta-Tyrosine

Figure 6:
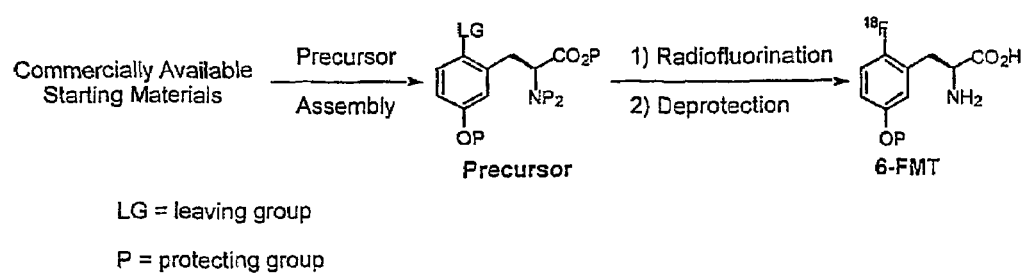
FIG. 6 depicts a strategy for Preparation of 6-FMT.

The strategy for synthesizing 6-[$^{18}$F]Fluoro-meta-Tyrosine (6-FMT), as illustrated in FIG. 6, involves the preparation of a precursor containing the protected or latent phenolic and amino acid functionalities, the required S-absolute configuration at the α-carbon, and a suitable leaving group. Radiofluorination displaces the leaving group and then 6-FMT is prepared by subsequent deprotection and/or functional group interconversion. Various model compounds were investigated in this research. Catechol derivatives having various leaving groups (LG) were examined as possible model precursors to a target product. It should be pointed out that all synthetic methodology discussed below was developed using regular "cold" [$^{19}$F]fluoride. However, once the system was established, fluorination was accomplished with "hot" [$^{18}$F]fluoride.

Preparation of Benzophenone Derivatives

A number of benzophenone derivatives were studied to develop the best route to the target compound. This structural unit was key to carrying out a successful radiofluorination. Earlier models contained a hydrogen or methyl group in place of amino acid group pendant from one of the aromatic rings. These models, which also varied in one of the aryl functionalities ($NO_2$, $NH_2$, $NMe_2$, $^+NMe_3^-OTf$, F) served as the leaving group or its precursor for the radiofluorination. These compounds are discussed below.

Figure 7:
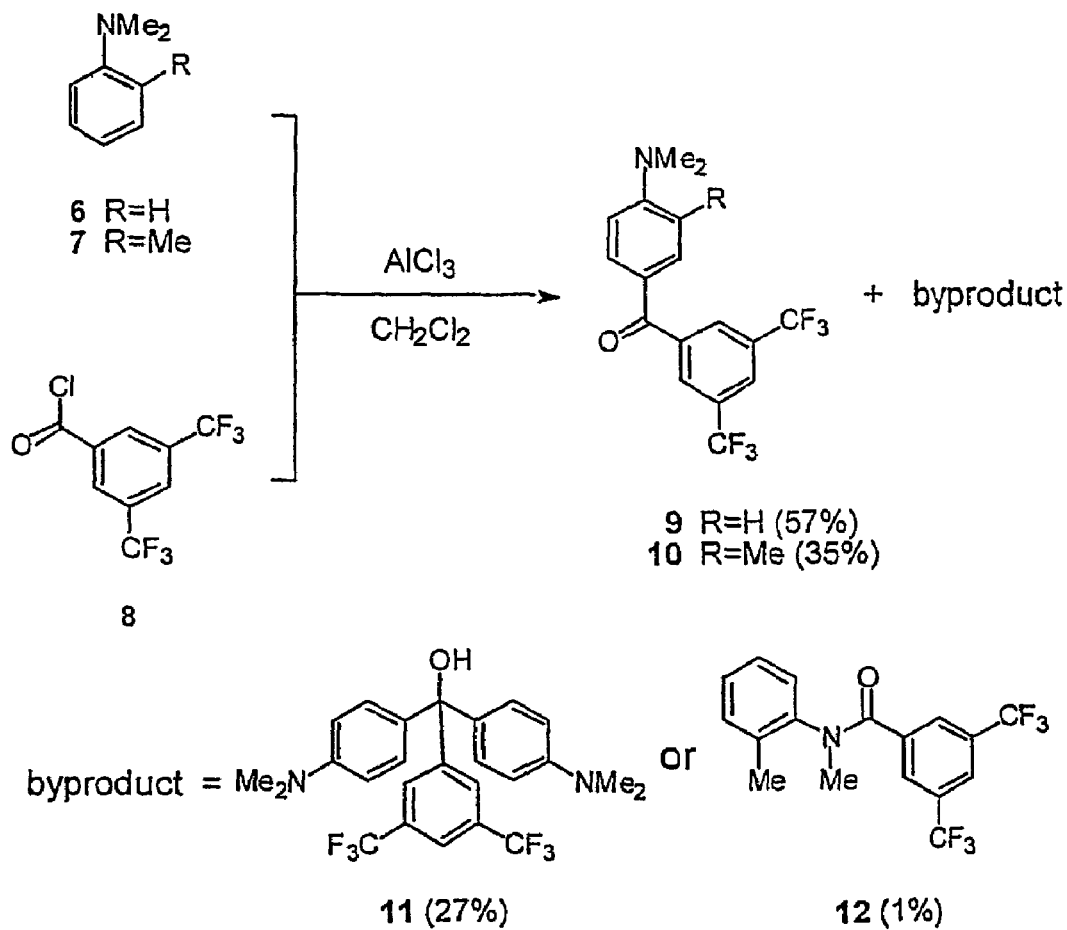
FIG. 7 illustrates Friedel-Crafts Acylation to generate N,N-Dimethylaminobenzophenone Derivatives.

Two methods were employed to generate the benzophenone backbone: 1) Friedel-Crafts Acylation (see N. E. Deuo; C. U. Pittman Jr.; M. J. Witotsky, J. Am. Chem. Soc., 1964, 86, 4370; G. Olah; M. B. Comisarow, J. Am. Chem. Soc., 1966, 88, 4442; and G. Olah; S. Kobayashi, J. Am. Chem. Soc., 1971, 93, 6964, all of which are incorporated herein by reference) and 2) Grignard Reaction (see F. Sato; M. Inoue; K. Oguro; M. Sato, Tetrahedron Lett., 1979, 44, 4303, incorporated herein by reference). Since an ammonium triflate and an activating group are needed for optimal radiofluorination results, compound 9 (see FIG. 7), a precursor for one of the model compounds, was prepared. As shown in FIG. 7, Friedel-Crafts acylation of commercially available 6 and 8 gave product 9. Two equivalents of the Lewis acid were used to form the aryl ketone at 0° C. The reaction gave the desired para-substituted product 9 as the major product and the triphenylmethanol 11 in minor amounts. However, the corresponding reaction with toluidine 7 also gave the desired para-substituted product 10 but not the triphenylmethanol as the byproduct. Interestingly, a quaternary salt was made from toluidine 7 and acid chloride 8 during the reaction and amide 12 was formed from this salt after base workup. Flash chromatography was used to isolate 9 and 10 as a yellow solid and yellow oil, respectively, for the subsequent quaternization reaction.

Figure 8:
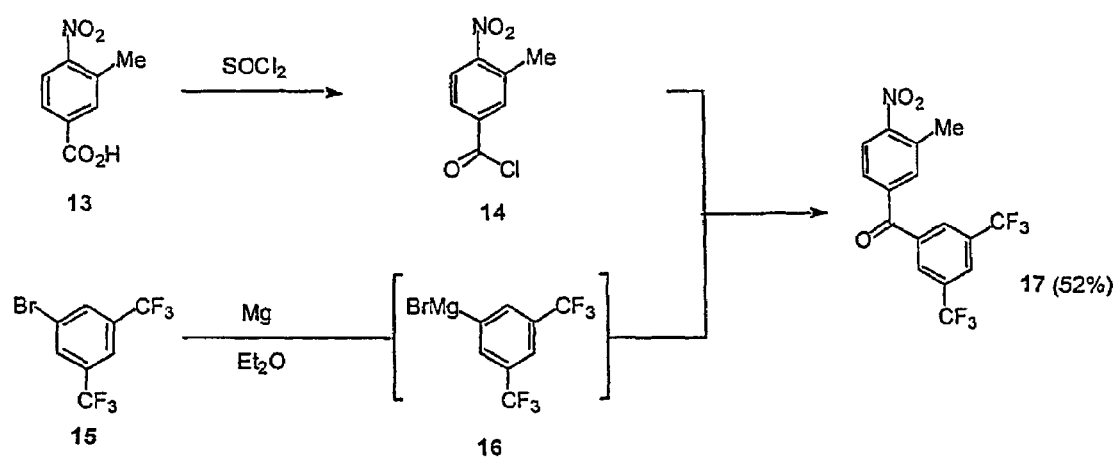
FIG. 8 illustrates Grignard Reaction to generate 3-Methyl-4-Nitrobenzophenone derivative 17.

Although 100% [$^{18}$F]-fluoride incorporation was achieved from the quaternized ammonium triflate of 9 (prepared by treatment of 9 with MeOTf), our studies eventually revealed that this route did not allow for ready introduction of the amino acid side chain. Thus, the search for another candidate yielded 17, which was prepared by direct reaction of Grignard reagent 16 with the acid chloride 14 as shown in FIG. 8.

Acid chloride 14 was easily prepared by treating the commerically available carboxylic acid 13 with thionyl chloride to yield a low-melting yellow solid (see D. W. Robertson; J. D. Leander; R. Lawson; E. E. Beedle; C. R. Clark, J. Med. Chem., 1987, 30, 1742, incorporated herein by reference). The Grignard reagent in THF was added dropwise to a THF solution of excess acid chloride 14 at −78° C. Once quenched, the dark blue reaction mixture afforded a yellow crystalline product 17, which was used for further transformations.

Figure 9:
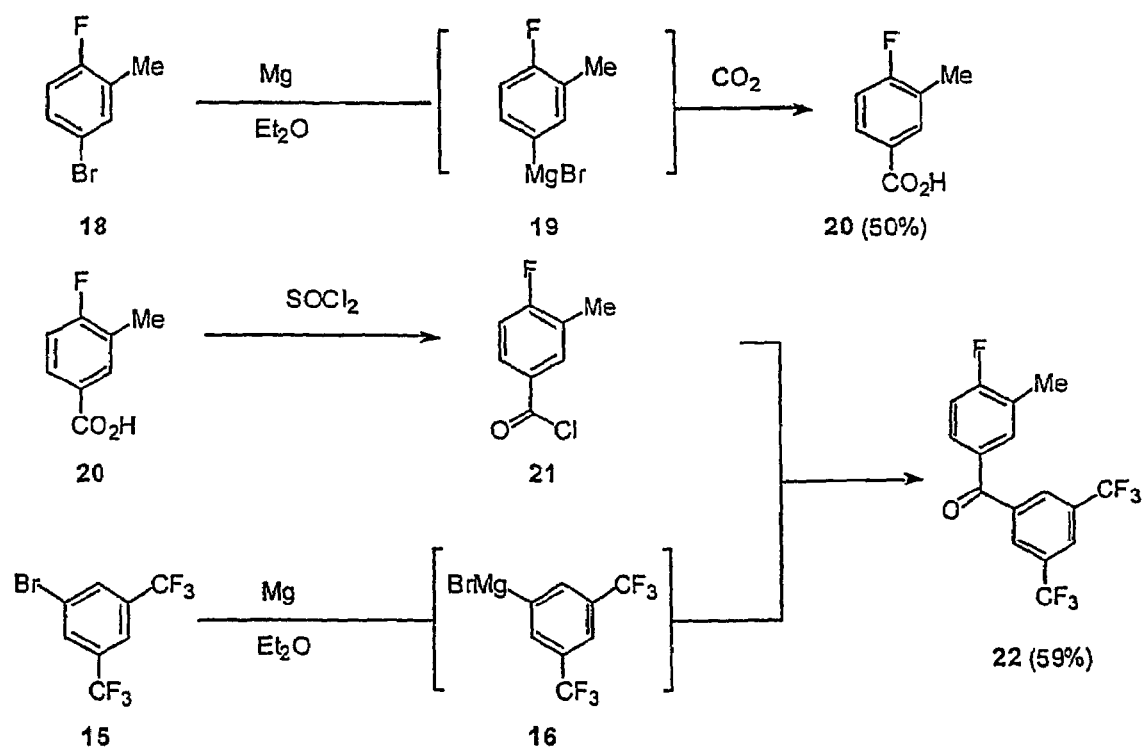
FIG. 9 depicts a synthetic route to prepare reference compound 22.
Figure 10:
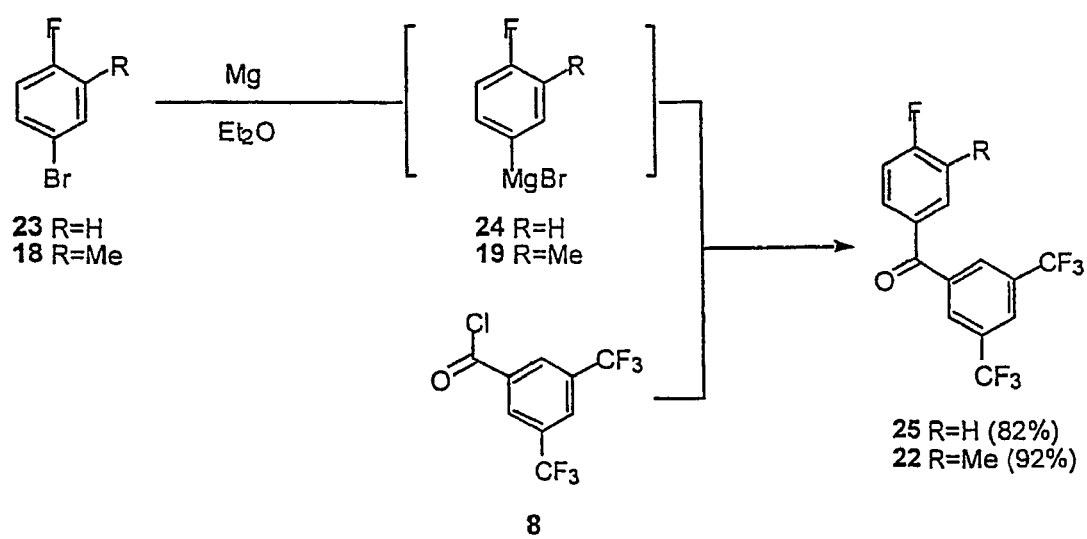
FIG. 10 depicts a synthetic route to prepare reference compounds 25 and 22.

As shown in FIGS. 9 and 10, reference compounds 22 and 25 were prepared in a similar manner to that for compound 17 from the respective acid chlorides and Grignard reagents. Compound 22 was first made by Route 1 and later by the simpler Route 2. In Route 1, Grignard reagent 19 was carboxylated to give carboxylic acid 20 (see W. H. Miller; T. W. Ku; F. E. Ali; W. E. Bondinell; R. R. Calvo; L. D. Davis; K. F. Erhard; L. B. Hall; W. F. Huffman; R. M. Keenan; C. Kwon; K. A. Newinader; S. T. Ross; J. M. Samanen; D. T. Takata; C.-K. Yuan, Tetrahedron Lett., 1995, 36, 9433, incorporated herein by reference). Transformation of 20 to the benzoyl chloride 21 was carried out in the same manner as indicated for compound 13 to 14. From commercially available 18, another Grignard reagent 19 was prepared and reacted with 21 to give 22. The synthesis of 22 was later accomplished by Route 2 since it contained one less Grignard reaction and no carboxylation step.

Figure 12:
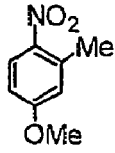
FIG. 12 shows Benzylic Halides prepared for precursor development.

Now referring to FIGS. 11 and 12, N-bromosuccinimide (NBS) is a common and highly regioselective brominating agent for allylic and benzylic brominations. A nonpolar solvent, such as carbon tetrachloride and the free-radical initiator benzoyl peroxide or AIBN are commonly used in the NBS reaction.

The free radical benzylic-type bromination reaction was examined for various di-substituted aromatic compounds. Compounds were selected to provide an array of candidates to serve as model or reference compounds for the target molecule. The keys for successful bromination are the use of a compound with a reasonable solubility in $CCl_4$ and careful monitoring of the reaction to avoid overreaction to form the dibromide or to lead to decomposition products.

Bromination attempts were first attempted on compounds 28 and 30 since they were precursors for radiofluorination. Both reactions proceeded smoothly. There is literature precedent for brominating 30 (see G. Ghirlanda; P. Scrimin; P. Tecilla; U. Tonellato, J. Org. Chem., 1993, 58, 3025, incorporated herein by reference) and the regioisomer of 28 (see P. K. Chakraborty; M. R. Kilbourn, Appl. Radiat. Isot., 1991, 42, 673, incorporated herein by reference). Benzoyl peroxide served as the initiator. It was added last to a mixture of substrate, NBS, and carbon tetrachloride. Heat and light were both used to initiate the reaction, which was completed in 3–5 hours. The solution typically changed to an orange color, signifying that active bromine was present. Another method to test for oxidizing activity was the use of Kl/starch paper; a positive test was indicated by a dark bluish-purple color change.

The completion of the reaction was indicated by the formation of succinimide, a white precipitate, along the solvent line in the reaction flask. A more exact determination was carried out by TLC analysis to follow the disappearance of the starting material. Aqueous sodium metabisulfite and then deionized water were used to wash the organic solution. The cloudy carbon tetrachloride layer was dried with either sodium sulfate or magnesium sulfate. The mixture was filtered and then the solvent was removed by vacuum to give an oil. Addition of a small amount of hexane to the oil and refrigeration produced crystalline product. However, since radiofluorination was not successful with the derived ammonium triflates the benzyl bromides 29 and 31 were not used further.

Compounds 35, 36, 38 (see FIG. 13), and 32 (see FIG. 12) were prepared in a similar manner to yield the alkylating agents for making respectively, cold 6-[$^{19}$F]-FMT, [$^{19}$F]-benzophenone amino acid, [$^{19}$F]-phenylbenzoate amino acid, and the eventual alkylated Schiff base of the final route. Note that compound 33 could not be prepared because NBS bromination led to undesired side-products and not to the benzyl halide.

Figure 14:
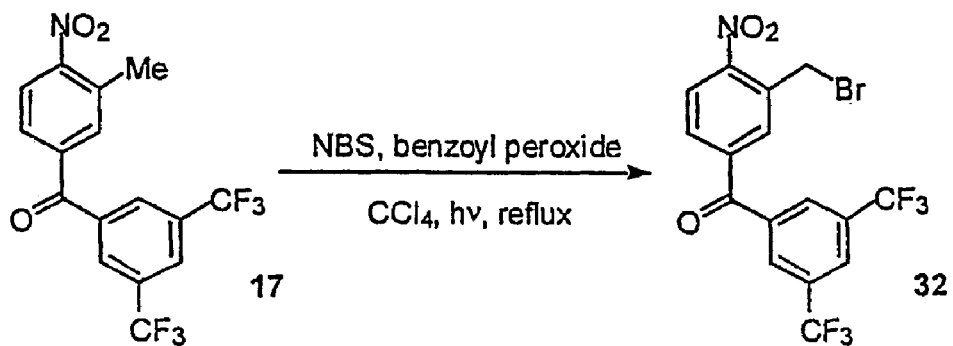
FIG. 14 illustrates a study of the NBS Bromination of Benzophenone substrate 17.

Since compound 33 could not be prepared an alternate route was explored. Variables in the bromination of an aromatic methyl included use of initiators (benzoyl peroxide, AIBN), reflux time (2 h-overnight), and irradiation (0–200 W lamp). The amount of NBS used for monobromination fell into the narrow range of 1.0–1.5 equivalents to prepare the target 32 (see FIG. 12). This bromination was carried out under conditions used for earlier brominations (1.2 eq NBS, benzoyl peroxide, $CCl_4$, irradiation, and heating). Since 32 was obtained in only modest yields, optimization experiments were undertaken by varying the amounts of NBS (see FIG. 14), benzoyl peroxide, and solvent used.

The initial reaction conditions (see, Expt 1 of FIG. 14) gave compound 32 in less than 50% yield with more than 50% of recovered starting material. By increasing either the amount of NBS used or the reaction time, the yield of product was increased (see FIG. 14, Expt 4–9). However, in both cases, the amount of dibrominated byproduct also increased. In addition, use of multiple additions of benzoyl chloride during the course of the reaction to maintain a constant level of initiator had virtually no effect on the product yield (see FIG. 14, Expt 3). Since the starting material could be readily recovered, the final conditions chosen (see FIG. 14, Expt. 2) involved stopping the reaction prior to dibromination and recovering the starting material for future use. No aromatic bromination was observed throughout this study.

Figure 15:
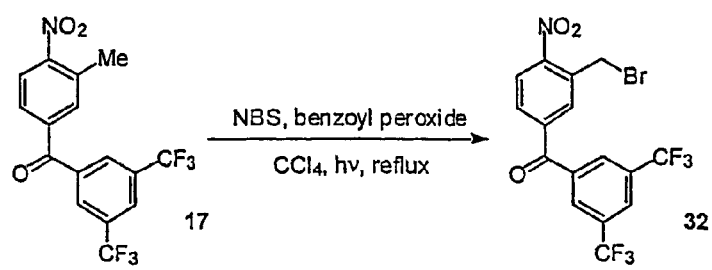
FIG. 15 depicts a concentration study of the NBS Bromination of Benzophenone substrate 17.

As shown in FIG. 15, attempts to change the concentration of various reagents to increase the yield of benzylic bromide 32 were also not successful. A solvent volume of 0.5–1.0 mL gave the highest product and lowest byproduct yields for the 100 mg reaction. NBS reactivity was suspected and determined to be inversely proportional to the solvent volume. The increase in reaction time at lower concentrations confirmed that the reaction does not go to completion without the formation of the dibrominated byproduct.

Figure 16:
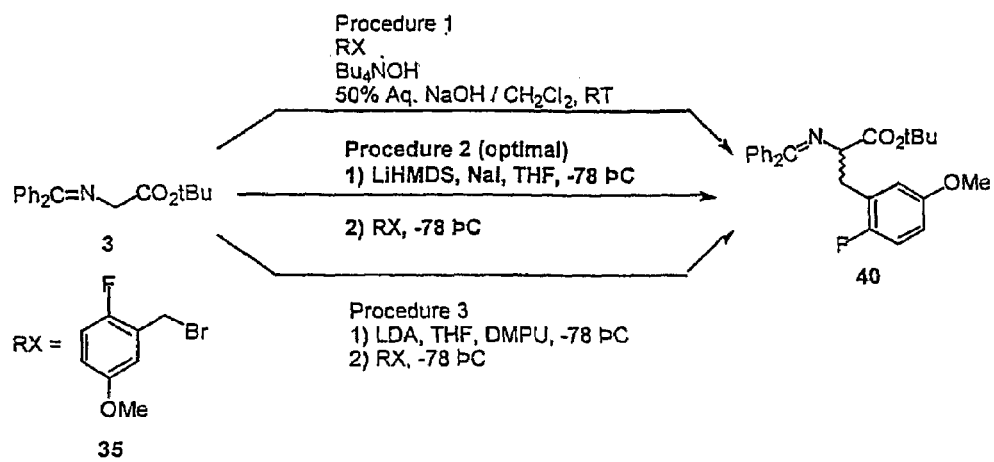
FIG. 16 illustrates racemic alkylation studies of Schiff Base Ester 3 with Benzylic Halide 35.

As shown in FIG. 16, several alkylation procedures were attempted during the development of the final route. Initial studies included both phase-transfer catalysis (PTC) (see J. J. Knittel; X. He, Peptide Research, 1990, 3, 176, S. R. Wilson; A. Yasmin; Y. Wu, J. Org. Chem., 1992, 57, 6941, A. V. Rama Rao; K. Laxma Reddy; A. Srinivasa Rao; T. V. S. K. Vittal; M. M. Reddy; P. L. Pathi, Tetrahedron Lett., 1996, 37, 3023, and L. Ridvan; N. Abdallah; R. Holakovsky; M. Tichy; J. Zavada, Tetrahedron: Asymmetry, 1996, 7, 231, all of which are incorporated herein by reference) and non-PTC methods, using anhydrous conditions with either LiHMDS (see R. Chinchilla; N. Galindo; C. Nájera, Tetrahedron, 1996, 52, 1035, incorporated herein by reference) or LDA (see J. R. Grierson; M. J. Adam, J. Lab Compd Radiopharm, 1986, 23, 1019, J. Dubois; C. Fourès; S. Bory; S. Falcou; M. Gaudry; A. Marquet, Tetrahedron, 1991, 47, 1001, J. W. Tilley; W. Danho; K. Lovey; R. Wagner; J. Swistok; R. Makofske; J. Michalewsky; J. Triscari; D. Nelson; S. Weatherford, J. Med. Chem., 1991, 34, 1125, J. M. Receveur; M. L. Roumestant; Ph. Viallefont, Amino Acids, 1995, 9, 391, C. Dugave; A. Menez, J. Org. Chem., 1996, 61, 6067, K. Tanaka; M. Ahn; Y. Watanabe; K. Fuji, Tetrahedron: Asymmetry, 1996, 7, 1771, and Y. Yost; T. Conway, Nucl Med Biol, 1996, 23, 857, all of which are incorporated herein by reference) as the base, for preparing the Schiff base-protected glycine derivative 40. All three procedures gave clean product in good yields. However, the LiHMDS protocol gave the best yield, which unlike the other two methods was also free of benzophenone. Analysis by proton NMR showed that the crude yields for methods 2 and 3 were slightly higher than theoretical due to residual toluene derivative from the previous NBS reaction and pentane from the alkylation workup.

Figure 17:
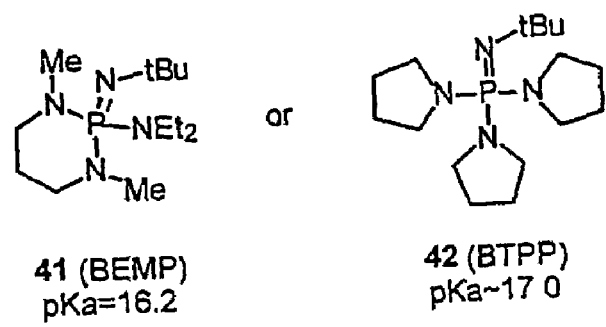
FIG. 17 depicts Schwesinger bases BEMP 41 and BTPP 42.

The complementary use of organic soluble, non-ionic phosphazene (Schwesinger) bases with chiral PTC catalysts has given impressive enantioselectivities as well as several advantages for the preparation of amino acid derivatives (see M. J. O'Donnell; F. Delgado; C. Hostettler; R. Schwesinger, Tetrahedron Lett., 1998, 39, 8775, incorporated herein by reference). This combination provides the advantage of a "one-time addition" reaction, since it is possible to have both the base and electrophile present throughout the alkylation, because the base is not readily alkylated. A second advantage of using the Schwesinger bases is that, since the reaction medium is homogenous, vigorous and effective stirring, typically needed to increase the interaction of the two phases in PTC chemistry, is not necessary for a successful reaction. In addition, base strength can be adjusted dependent on the reactivity of the alkylating agent to use either the weaker BEMP or the stronger Schwesinger base, BTPP (see FIG. 17).

Figure 18:
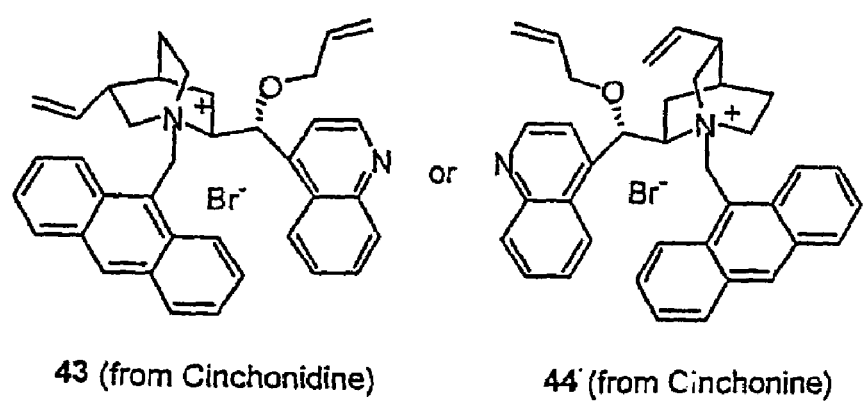
FIG. 18 illustrates pseudoenantiomeric catalysts derived from the Cinchona Alkaloids.

Finally, there seems to be a dual role for the chiral catalyst. The primary purpose for using the catalyst is to provide a chiral environment for the asymmetric synthesis. Refering to FIG. 18, catalyst 43 yields the natural S-form of the amino acid while catalyst 44 yields the enantiomeric R-form (see M. J. O'Donnell; I. A. Esikova; A. Mi; D. F. Shullenberger; S. Wu, Phase-Transfer Catalysis: Mechanisms and Syntheses, M. E. Halpern, Ed., American Chemical Society, Washington D.C., 1997, 124, incorporated herein by reference). Interestingly, it was observed that use of the quaternary ammonium salt also increases the product yield when compared with the similar reaction conducted in the absence of catalyst. Hence, all the alkylation reactions were run in the presence of 0.1 eq catalyst 43 except when racemic mixture was needed for preliminary chiral HPLC analyses.

Figure 19:
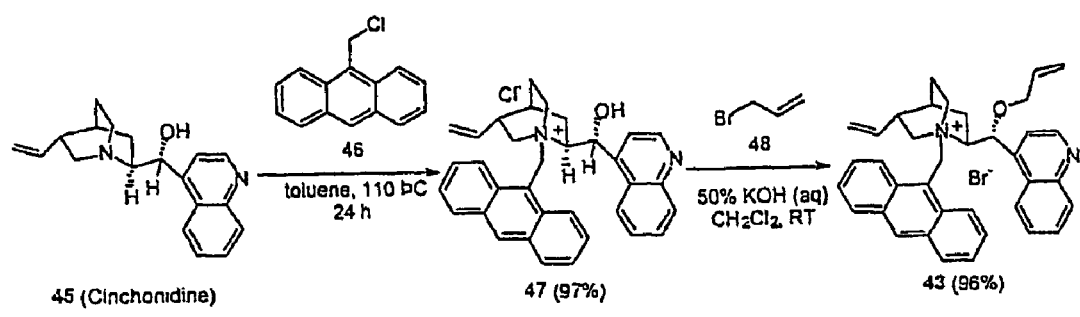
FIG. 19 illustrates the preparation of PCT catalyst 43.

The present invention is primarily directed to the generation of the biologically active S-form of the amino acid, accordingly only catalyst 43 was necessary. As shown in FIG. 19, catalyst 43 was made using a two-step procedure. In particular, a mixture of 9-(chloromethyl)anthracene and cinchonidine were refluxed in toluene, which eventually gave a clean product, N-(9-anthracenylmethyl)cinchonidinum chloride, as a yellow solid in nearly quantitative yield. This product was then reacted with allyl bromide in the presence of 50% aqueous KOH in dichloromethane to afford the crude yellow product 43. Recrystallization gave pure catalyst 43 in good yield (see E. J. Corey; F. Xu; M. C. Noe, J. Am. Chem. Soc., 1997, 119, 12414, incorporated herein by reference).

Figure 20:
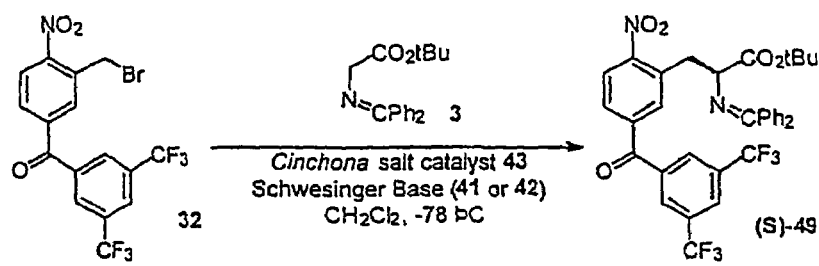
FIG. 20 depicts asymmetric alkylation studies of Schiff Base Ester 3 with Benzylic Halide 32.

As shown in FIG. 20, once catalyst 43 was prepared, several reactions were attempted to find the optimal alkylation conditions using the Schwesinger bases. The more reactive base, BTPP, gave better yields in the alkylation with a non-active benzyl bromide than BEMP. Interestingly, the presence of catalyst did improve the yields for the BTPP series but not for the BEMP series, where decreased yields were observed. Solvent concentration also affected the reaction yield, which yield improved from 49% to 57% by increasing the Schiff base concentration from 0.17 M to 0.34 M. Thereafter, alkylation reactions with compound 32 followed procedure 5 of FIG. 20.

Compounds 50 and 51 (see FIG. 21) were synthesized for reference purposes for HPLC analysis. Both the LiHMDS and BTPP procedures were used to prepare 50 while only the BTPP method was used to make 51. Although flash chromatography was used for compounds 50, 40, and 49, compound 51 could not be isolated in this way. A deactivated column prepared with 1% TEA in 99% 9:1 hexane/EtOAc was the only way compound 51 could be isolated without significant loss (see E. J. Corey; M. C. Noe; F. Xu, Tetrahedron Lett., 1998, 39, 5347, incorporated herein by reference). Crude alkylation products 50, 51, 40 and 49 were subjected to rapid flash chromatography to remove the BTPP and polar impurities. The resultant semi-pure reaction product, containing a minor amount of Schiff base starting material 3 (see FIG. 5), was treated with 0.2 N HCl/THF to give the corresponding hydrochloride salt, which was then used directly in the Boc-derivatization step.

Nitro Group Reduction and Reductive Methylation

N-methylation of a primary amine to give a tertiary amine is an important but sometimes problematic reaction. Shortcomings of established methylation procedures include the formation of complex mixtures of unalkylated, partially methylated, and quaternary ammonium products, or C-sulfonation when aromatic amines are methylated with dimethyl sulfate. Aromatic amines containing ortho or para-nitro groups are more difficult to alkylate to the tertiary amines than their aliphatic counterparts. Forcing conditions and longer reaction times were necessary to overcome this difficulty. The product tertiary amines were eventually converted to quaternary ammonium triflates, as discussed below.

Figure 22:
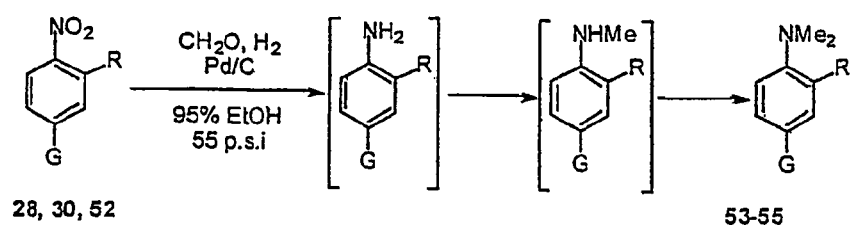
FIG. 22 illustrates reductive methylations to prepare products 53, 54, and 55.

As shown in FIG. 22, reductive methylation of compounds 28 and 30 with formaldehyde in a Parr hydrogenation apparatus was used to transform nitrophenyl compounds into the corresponding tertiary amines. The reaction was run overnight with six and four equivalents of formaldehyde, respectively, for compounds 28 and 30. Although this procedure did give the desired compounds as the major product, the reaction mixture still contained the primary amine by TLC. It might be possible to increase the yield further by using 10 eq. However, since radiofluorination of the respective ammonium triflates and benzylic bromination of the dimethyl toluidines derived from 28 and 30 were not successful, efforts to optimize these reactions were discontinued.

Still referring to FIG. 22, compound 52 was subjected to reductive methylation. This nitrobenzophenone derivative was subjected to reductive methylation conditions similar to those used for compounds 28 and 30. The initial attempt gave a complex mixture of mono-methylated products and none of the desired tertiary amine. The next attempt resulted in a 12% yield of the dimethyl amine, 29% of the monomethyl amine, with the major products being a complex polar mixture. Since several steps are involved in the preparation of compound 52, additional efforts to optimize the reductive methylation step were directed to the simpler and more readily prepared model compound 17 (see FIG. 15).

The reductive methylation accomplishes three steps in a single reaction. First, the nitro group is reduced to the corresponding primary amine followed by conversion to the mono- and then dimethylamine. Two separate reactions were utilized to prepare compound 55. In particular, first the nitro group was reduced in the first reaction to the primary amine, which was then isolated (see L. Wessjohann; G. McGaffin; A. De Meijere, *Synthesis*, 1989, 5, 359, incorporated herein by reference). In the second reaction, the primary amine was subjected to the methylation conditions to lead to the dimethyl amine (see Herre, *Chem. Ber.*, 1895, 28, 597, L. Chardonnens; W. Schlapbach, *Helv. Chim. Acta*, 1946, 29, 1413, M. Rieger; F. H. Westheimer, *J. Am. Chem. Soc.*, 1950, 72, 28, M. Zrihen; R. Labia; M. Wakselman, *Eur. J. Med. Chem. Chim. Ther.*, 1983, 18, 307, D. W. Robertson; J. D. Leander; R. Lawson; E. E. Beedle; C. R. Clark; B. D. Pofts; C. J. Parli, *J. Med. Chem.*, 1987, 30, 1742, K.-I. Kataoka; T. Shiota; T. Takeyasu; T. Mochizuki; K. Taneda; M. Ota; H. Tanabe; H. Yamaguchi, *J. Med. Chem.*, 1995, 38, 3174, all of which are incorporated herein by reference). Model compound 17 was used to develop these two reactions.

Figure 23:
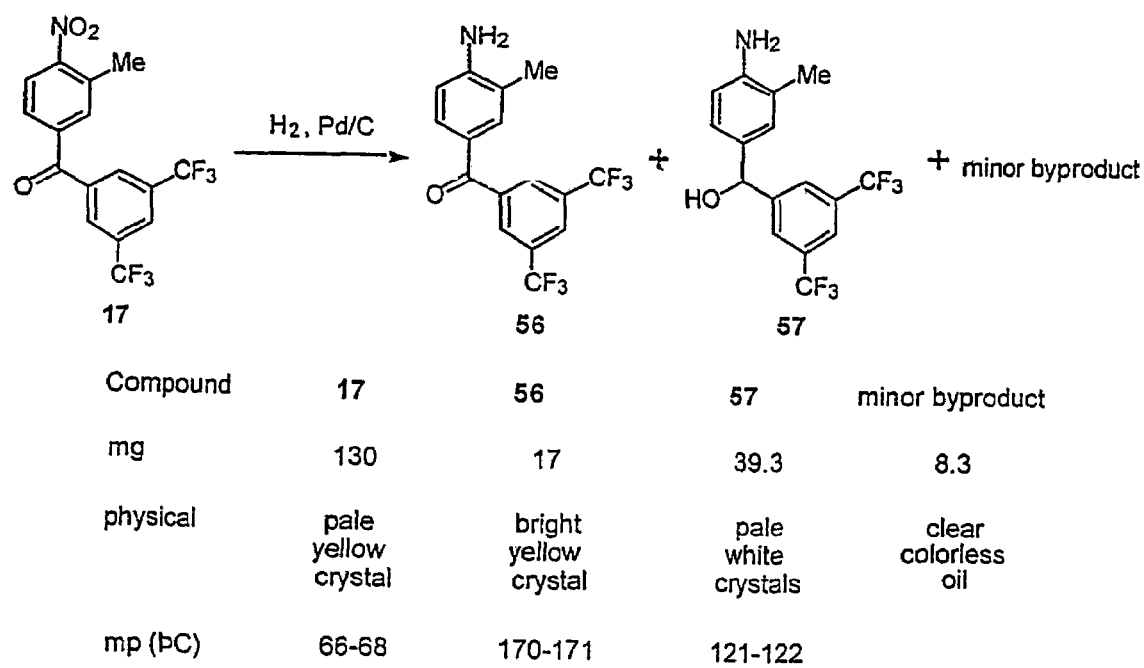
FIG. 23 depicts Nitro group reduction of substrate 17.

As shown in FIG. 23, following a procedure similar to that reported by Kataoka et al, (see K.-I. Kataoka; T. Shiota; T. Takeyasu; T. Mochizuki; K. Taneda; M. Ota; H. Tanabe; H. Yamaguchi, *J. Med. Chem.*, 1995, 38, 3174 previously incorporated herein bny reference) compound 17 was reacted under the same conditions as above except that formaldehyde was excluded. Within 15 minutes at 0.1 M concentration, the reaction was complete and the undesired reduction of the benzophenone carbonyl was starting to be observed.

Figure 24:
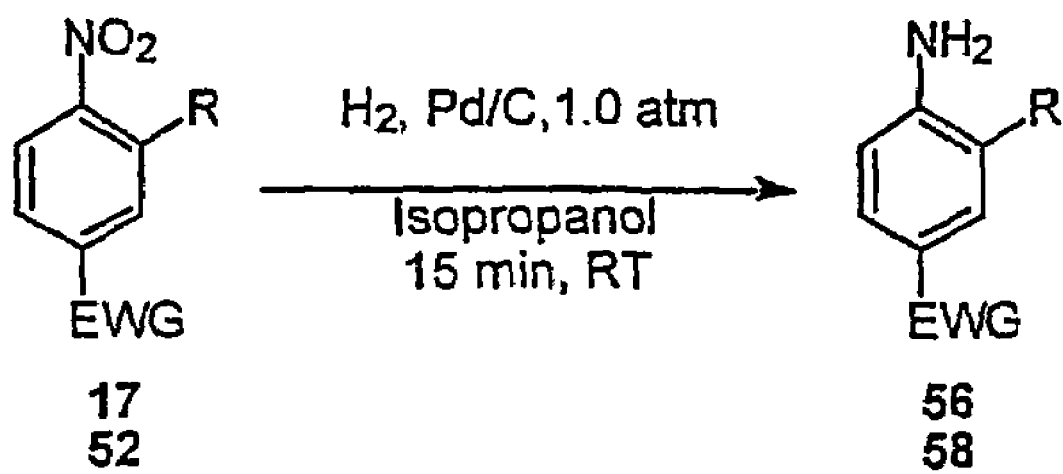
FIG. 24 illustrates Nitro group reduction in isopropanol.
Figure 25:
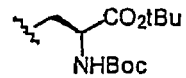
FIG. 25 illustrates results from optimized Nitro group reduction conditions for compounds 17 and 52.
Figure 26:
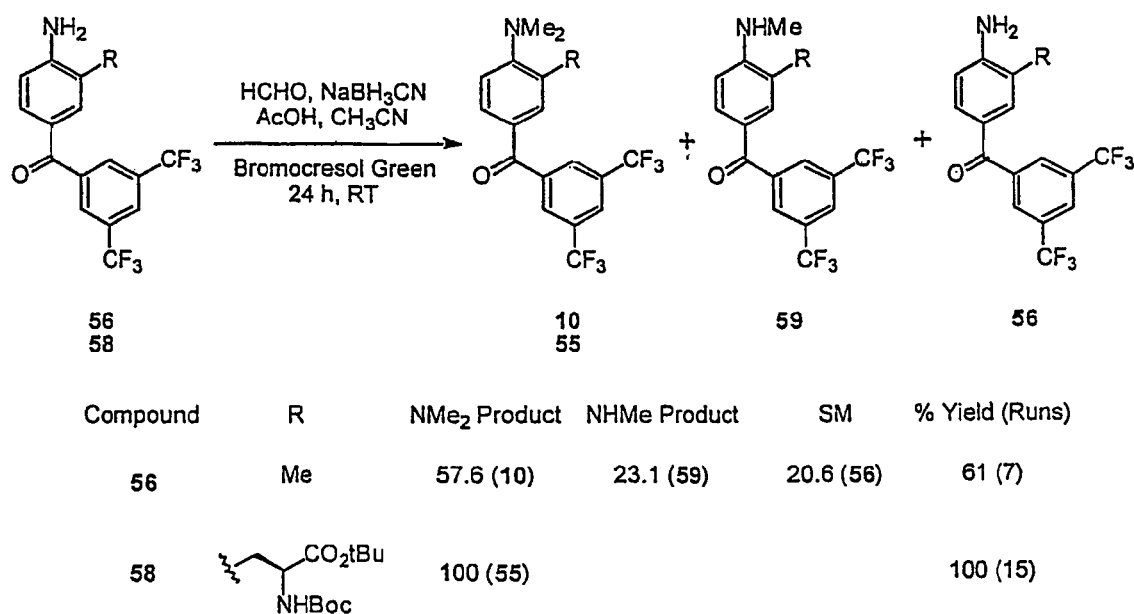
FIG. 26 illustrates reductive alkylation of Aniline derivatives 56 and 58.

In order to reduce the rate and increase the selectivity of the reduction, other solvents such as isopropanol and ethyl acetate were tried. Both reactions, especially the latter, were also quite rapid. With isopropanol, however, after 15 minutes the nitro to amine reduction was completed with no concomitant carbonyl reduction. The reaction was quenched after 15 minutes by filtration through celite. In this way, as shown in FIGS. 24 and 25, products 56 and 58 were isolated in nearly quantitative yield and then subjected to the second reaction, a formaldehyde-cyanoborohydride reductive methylation (see R. F. Borch; H. D. Durst, J. Am. Chem. Soc., 1969, 91, 3996, R. F. Borch; M. D. Bernstein; H. D. Durst, J. Am. Chem. Soc., 1971, 93, 2897, and R. F. Borch; A. I. Hassid, J. Org. Chem., 1972, 37, 1673, all of which are incorporated herein by reference).

Utilizing the formaldehyde-cyanoborohydride system compound 56 would be classified as an "unreactive" amine. The difference in conditions was a higher concentration of formaldehyde, cyanoborohydride, and acetic acid for such "unreactive" amines. When the pH for the reductive methylation was kept at ≧7, only compound 56 was recovered. More acidic conditions (pH~4–6) gave the monomethyl and/or desired dimethyl aryl amine. Since the reaction consumes acid, additional aliquots of acid were necessary to maintain the acidic conditions. Bromocresol green was used to monitor the amount of acid present in the mixture. As the indicator in the mixture turned green, when acid was consumed, more acid was added until the mixture became yellow, indicating an acidic solution. The reaction was allowed to continue until formation of the dimethyl amine ceased by TLC observation. Proton NMR analysis showed that the major product from the reductive methylation of compound 56 was the dimethylated product 10 (see FIG. 25). Monomethylated product and unreacted starting material were also present in the mixture in minor amounts. Subsequently, this procedure was applied to compound 58 and product 55 was prepared in nearly quantitative yield. Compound 55 was used for later modification in a final route.

Protection/Deprotection Studies

Figure 27:
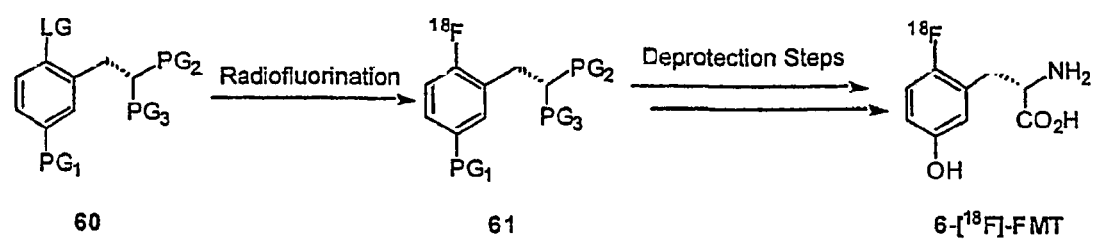
FIG. 27 depicts radiofluorination and deprotection of [$^{18}$F]-Fluorine-Containing substrates.

As a chemical reaction is occurring at one reactive site, the temporary protection of other reactive sites in the same compound often becomes necessary. The precursor for radiofluorination 60 (see FIG. 27) was designed to have three protecting groups (PG) that could be cleaved in one or two quick steps following the labeling reaction. The first protecting group masks the phenolic group and activates the ring for nucleophilic aromatic substitution. The second and third groups protect the amine and carboxylic acid of the amino acid, respectively. These groups were modified, when necessary, to withstand the different reaction conditions to which they were exposed.

Two reaction steps influenced protection group selection for a final route: 1) quaternization to the ammonium triflate and 2) radiofluorination. The radiofluorination step employs anionic fluoride-18 as a nucleophile for nucleophilic aromatic substitution. Hence, there cannot be any competing electrophilic functionalities (i.e. acetoxy group on the aromatic ring) present on the compound in addition to the reactive site. Although the primary role of fluoride is as a nucleophile, it can also act as a weak base. Thus, the phenol functionality must be masked with a protecting group.

Figure 28:
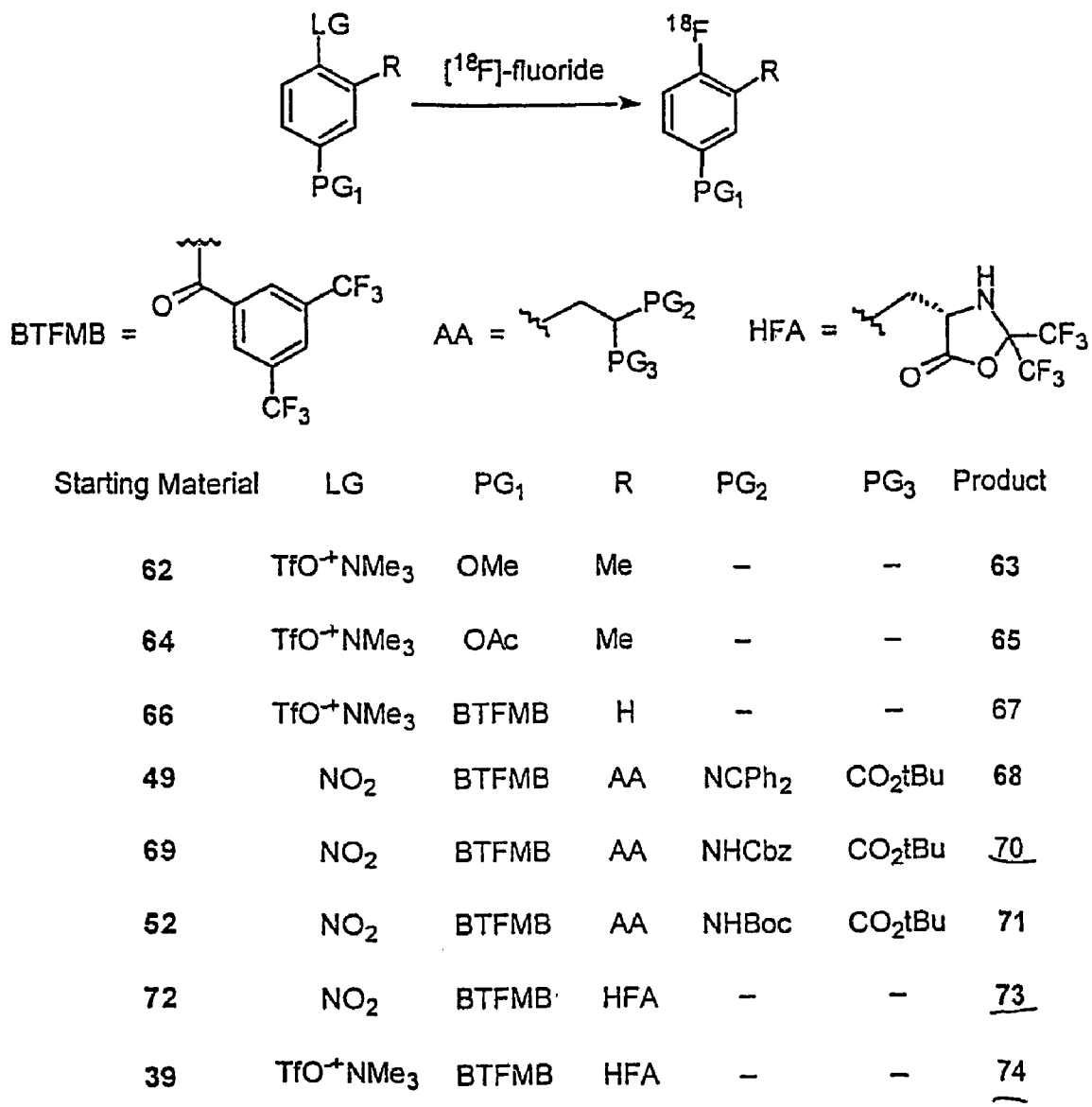
FIG. 28 illustrates introduction of $^{18}$F by nucleophilic aromatic substitution to potential precursors.

The hydroxyl group was masked as an ether, an ester, or a ketone (see "Protective Groups in Organic Synthesis," T. W. Greene; P.G.M. Nuts, John Wiley & Sons, Inc., New York, 1991, incorporated herein by reference). Initially, without the amino acid side chain, the ketone gave the best radiofluorination results in combination with the ammonium triflate as the leaving group on the benzophenone moiety. These radiofluorination findings are discussed below. Once the fluorination conditions were defined, the protected amino acid functionality was built onto the benzophenone skeleton, which complicated matters. As shown in FIG. 28, in this case, two further protecting groups were needed to mask the amine and carboxylic acid.

A diprotected amino acid fragment can be introduced using Schiff base chemistry developed in our laboratory (see R. E. Marker; E. Rohrmann; H. M. Crooks; E. L. Wittle; E.

M. Jones; D. L. Turner, *J. Am. Chem. Soc.,* 1940, 62, 525 and J. Quick; J. K. Crelling, *J. Org. Chem.,* 1978, 43, 155, both of which are incorporated herein by reference). The classical O'Donnell Schiff base incorporates a diphenylketimine and a t-butyl ester, as the two protecting groups, onto a glycine scaffold. Alkylation of the Schiff base conveniently provides the completely masked higher amino acid. Unfortunately, the bromination of the 3-methyl-4-N,N-dimethylamino substrate 10 and radiofluorination of 49 were both unsuccessful, thus other routes were devised to obtain new candidates for radiofluorination.

Figure 29:
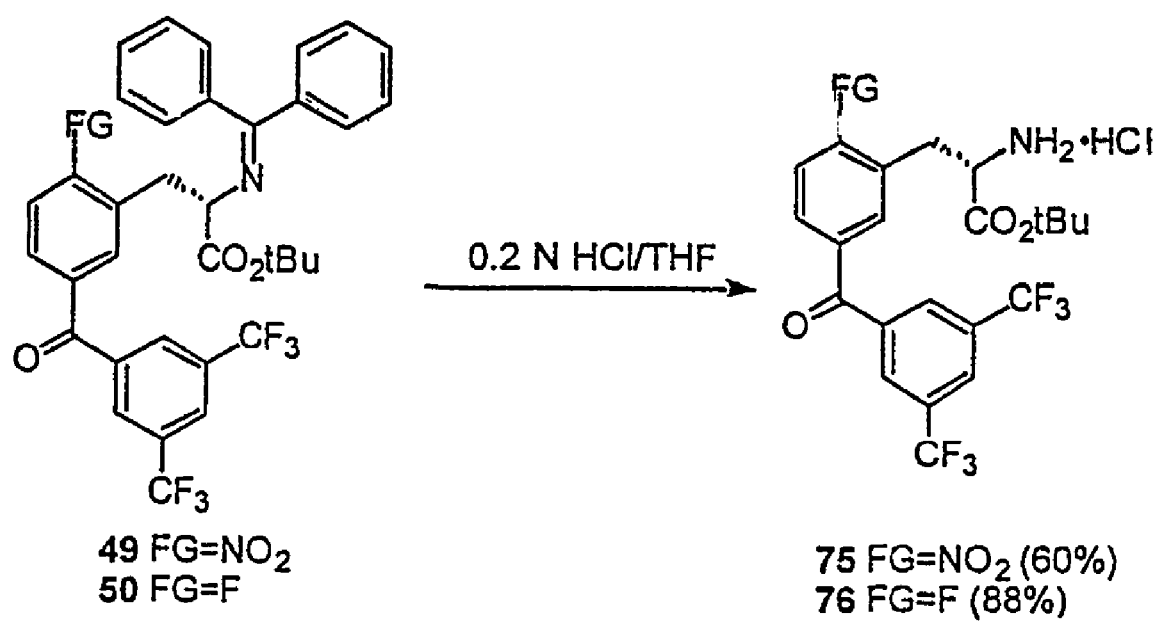
FIG. 29 depicts deprotection of a benzophenone imine protecting group.

Compound 49 transformed to compounds 52 and 69 for attempted radiofluorination. As shown in FIG. 29, compound 49 was treated with 0.2 N HCl in THF to give the corresponding HCl salt 75. When reacted with either CbzCl or Boc$_2$O in the presence of DIEA, (see Y. S. Ding; C. Y. Shiue; J. S. Fowler; A. P. Wolf; A. Plenevaux, J. Fluorine Chem., 1990, 48, 189, Y. S. Ding; J. S. Fowler; S. J. Gatley; S. L. Dewey; A. P. Wolf, J. Med. Chem., 1991, 34, 767, P. K. Chakraborty; M. R. Kilbourn, Appl. Radiate. Isot., 1991, 42, 673, P. K. Chakraborty; M. R. Kilbourn, Appl. Radiat. Isot., 1991, 42, 1209, K. Hashizume; H. Tamakawa; N. Hashimoto; Y. Miyake, Appl. Radiat. Isot., 1991, 42, 1209, Y. S. Ding; J. S. Fowler; S. J. Gatley; S. L. Dewey; A. P. Wolf; D. J. Schlyer, J. Med. Chem., 1991, 34, 861, Y. S. Ding; J. S. Fowler; A. P. Wolf, J. Label. Cmpds. Radiopharm., 1993, 33, 645, and H. Clark; D. Wails, J. Fluorine Chem., 1995, 70, 201, all of which are incorporated herein by reference). 75 afforded compounds 52 and 69, respectively, in nearly quantitative yield. 78 was used in a later study. Fluorination of either 52 or 69 showed evidence of fluoride incorporation, but it was inferior to the nearly quantitative incorporation demonstrated with the ammonium triflate leaving group. Thus, efforts were directed to transform the nitro group of 52 to an ammonium triflate.

Figure 30:
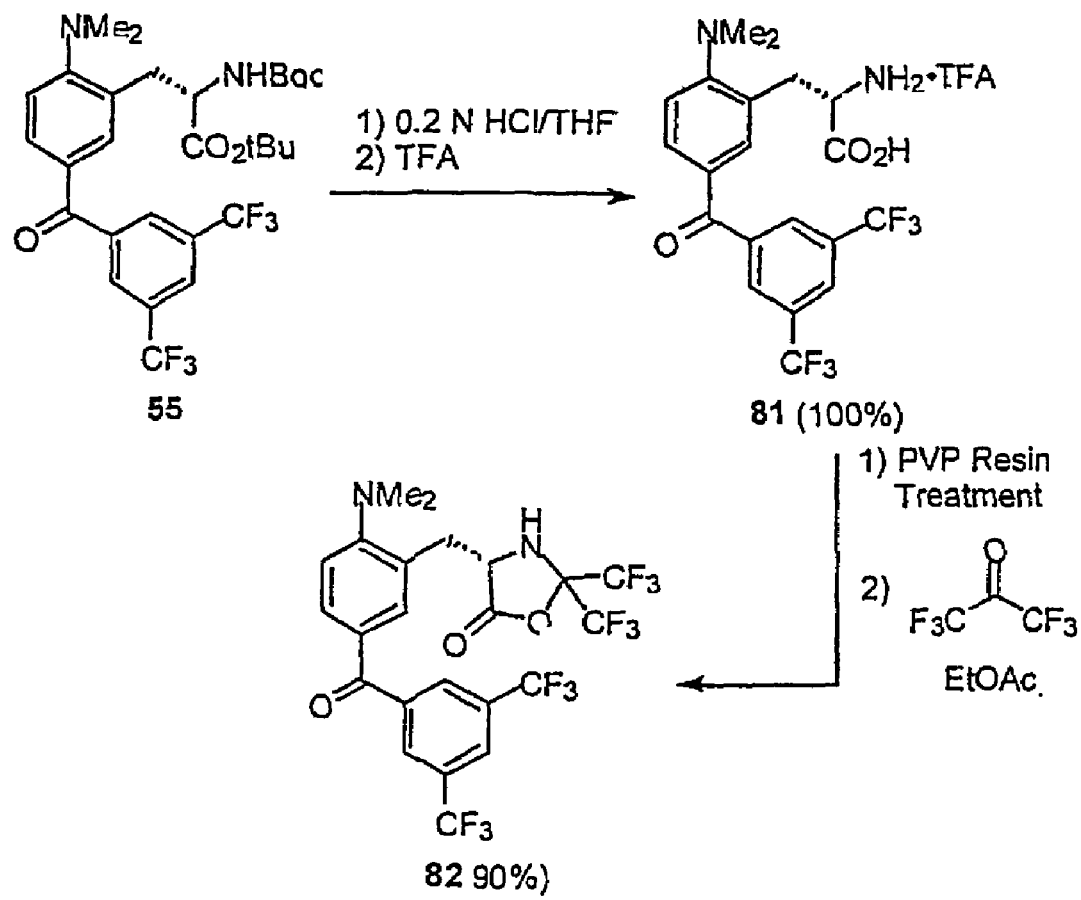
FIG. 30 illustrates the transformation of Boc and t-butyl ester groups into a HFA-Acetonide protecting group.
Figure 31:
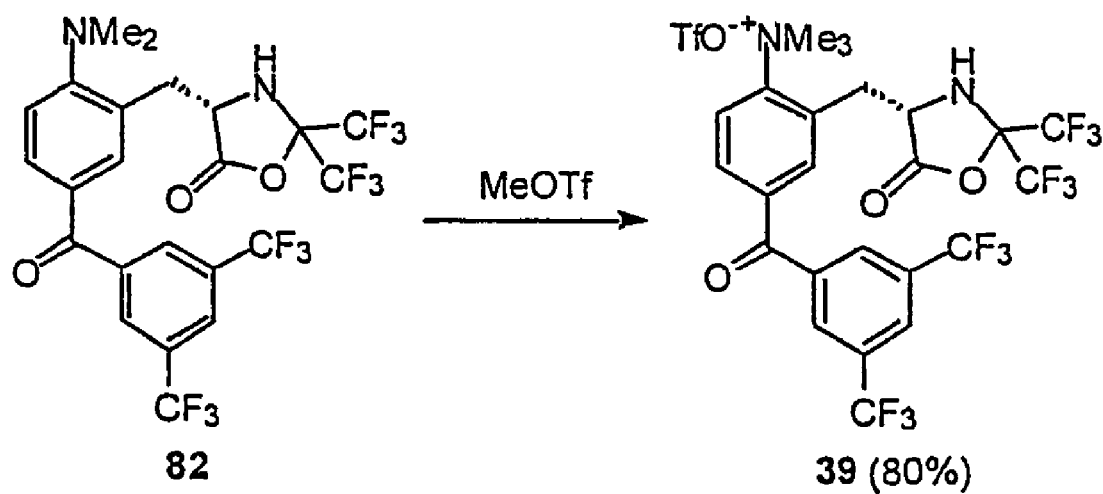
FIG. 31 depicts tertiary amine quaternization with methyl triflate.

The product of a free amino acid and hexafluoroacetone simultaneously protects the amine and carboxylic acid group. Burger et al were the first to use the 2,2-bis(trifluoromethyl)-1,3-oxazolidin-5-one group (HFA acetonide) in amino acid chemistry (see F. Weygand; K. Burger; K. Engelhardt, Chem. Ber., 1966, 99, 1461, C. G. Krespan; W. J. Middleton, Fluorine Chemistry Reviews, 1967, 1, 145, G. R. Leader, Analytical Chemistry, 1970, 42(1), 16, C. Joy; W. Fraser; D. W. A. Sharp; G. Webb; J. M. Winfield, J. C. S. Dalton, 1972, 2226, F.-L. Ho, Anal. Chem., 1973, 45, 603, F.-L. Ho, Anal. Chem., 1974, 46, 496, K. Burger; M. Rudolph; E. Windeisen; A. Worku; S. Fehn, Monatshefte fur Chemie, 1993, 124, 453, K. Burger; H. Neuhauser; A. Worku, Z. Naturforsch, B: Chem. Sci. 1993, 48b, 107, K. Burger; E. Windeisen; R. Pires, J. Org. Chem., 1995, 60, 7641, R. Pires; S. Fehn; A. Golubev; D. Winkler; K. Burger, Amino Acids, 1996, 11, 301, and M. W. Walter; R. M. Adlington; J. E. Baldwin; C. J. Schofield, J. Org. Chem., 1998, 63, 5179, all of which are incorporated herein by reference). This protecting group is useful for masking the amino acid functions during the methyl triflate reaction. As shown in FIGS. 30 and 31, the quaternization reaction of 82 was successful using the hexafluoroacetone protecting group to give compound 39. Radiofluorinations were carried out for both compounds 72 and 39 for comparison. Further discussion about the HFA, quaternization, and radiofluorination reactions are provided later.

Figure 32:
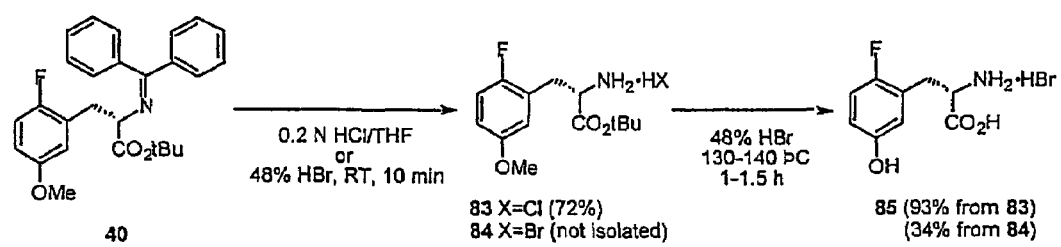
FIG. 32 illustrates deprotection of compound 40 to give compound 85.

The final deprotection procedure discussed herein involves the synthesis of 6-[$^{19}$F]fluoro-m-tyrosine. As previously discussed, compound 40 was made from the corresponding benzyl bromide 35 and the Schiff base 3. The first protecting group to cleave was the imine to afford either a white solid 83 (see FIG. 32) with HCl or an aqueous HBr mixture of 84 (see FIG. 32) with HBr. 83 and 84 were both heated at 130–140° C. with 48% HBr in a sealed glass tube for 1.0–1.5 h to cleave the methyl ether (see F. M. F. Chen; N. L. Benoiton, Can. J. Chem., 1987, 65, 1224, C. Dugave, J. Org. Chem., 1995, 60, 601, P. Chen; P. T. W. Cheng; M. Alam; B. D. Beyer; S. Bisacchi; T. Dejneka; A. J. Evans; J. A. Greytok; M. A. Hermsmeier; W. G. Humphreys; G. A. Jacobs; O. Kocy; P-F. Lin; K. A. Lis; M. A. Marella; D. E. Ryono; A. K. Sheaffer; S. H. Spergel; C-Q. Sun; J. A. Tino; G. Vite; R. J. Colonno; R. Zahler; J. C. Barrish, J. Med. Chem., 1996, 39, 1991, G. Sun; M. Slavica; N. J. Uretsky; L. J. Wallace; G. Shams; D. M. Weinstein; J. C. Miller; D. D. Miller, J. Med. Chem., 1998, 41, 1034, K. G. Dendrinos; A. G. Kalivretenos, J. Chem. Soc., Perkin Trans. 1, 1998, 9, 1463, L. J. S. Knutsen; J. Lau; H. Petersen; C. Thomsen; J. U. Weis; M. Shalmi; M. E. Judge; A. J. Hansen; M. J. Sheardown, J. Med. Chem., 1999, 42, 343, D. Enders; E. Diez, R. Fernández, E. Martin-Zamora, J. Muñoz; R. R. Pappalardo; J. M. Lassaletta, J. Org. Chem., 1999, 64, 6329, and D. J. Hallett; U. Gerhard; S. C. Goodacre; L. Hitzel; T. J. Sparey; S. Thomas; M. Rowley, J. Org. Chem., 2000, 65, 4984, all of which are incorporated herein by reference). Subsequent evaporation of the aqueous HBr solution yielded 85 (see FIG. 32) as a residue for reference analysis purposes.

Quaternization/HFA Reactions

As shown in FIG. 33, methods for preparing no-carrier-added (NCA) radiopharmaceuticals include nucleophilic aromatic displacement of a nitro or trimethylammonium group with $^{18}$F-fluoride (see Y. S. Ding; C. Y. Shiue; J. S. Fowler; A. P. Wolf; A. Plenevaux, J. Fluorine Chem., 1990, 48, 189, Y. S. Ding; J. S. Fowler; S. J. Gatley; S. L. Dewey; A. P. Wolf, J. Med. Chem., 1991, 34, 767, P. K. Chakraborty; M. R. Kilbourn, Appl. Radiat. Isot., 1991, 42, 673, P. K. Chakraborty; M. R. Kilbourn, Appl. Radiat. Isot., 1991, 42, 1209, K. Hashizume; H. Tamakawa; N. Hashimoto; Y. Miyake, Appl. Radiat. Isot., 1991, 42, 1209, Y. S. Ding; J. S. Fowler; S. J. Gatley; S. L. Dewey; A. P. Wolf; D. J. Schlyer, J. Med. Chem., 1991, 34, 861, Y. S. Ding; J. S. Fowler; A. P. Wolf, J. Label. Cmpds. Radiopharm., 1993, 33, 645, H. Clark; D. Wails, J. Fluorine Chem., 1995, 70, 201, M. S. Haka; M. R. Kilbourn; G. L. Watkins; S. A. Toorongian, J. Labeled Compds. Radiopharm., 1989, 27, 823, G. K. Mulholland, Appl. Radiat. Isot., 1991, 42, 1003, and P. Damahut; C. Lemaire; A. Plenevaux; L. Christiaens; D. Comar, Tetrahedron, 1997, 53, 5785, all of which are incorporated herein by reference). The fluorodenitration reaction usually requires a formaldehyde (ortho- or para-positioned) or benzoyl (para-positioned) group to facilitate the nucleophilic substitution. However, fluoride incorporation tends to be more facile when trimethylammonium triflate salts are used as leaving groups for the nucleophilic reactions with anionic fluoride (see F. Weygand; K. Burger; K. Engelhardt, Chem. Ber., 1966, 99, 1461, C. G. Krespan; W. J. Middleton, Fluorine Chemistry Reviews, 1967, 1, 145, G. R. Leader, Analytical Chemistry, 1970, 42(1), 16, C. Joy; W. Fraser; D. W. A. Sharp; G. Webb; J. M. Winfield, J. C. S. Dalton, 1972, 2226, F.-L. Ho, Anal. Chem., 1973, 45, 603, F.-L. Ho, Anal. Chem., 1974, 46, 496, K. Burger; M. Rudolph; E. Windeisen; A. Worku; S. Fehn, Monatshefte fur Chemie, 1993, 124, 453, K. Burger; H. Neuhauser; A. Worku, Z. Naturforsch, B: Chem. Sci. 1993, 48b, 107, K. Burger; E. Windeisen; R. Pires, J. Org. Chem., 1995, 60, 7641, R. Pires; S. Fehn; A. Golubev; D. Winkler; K. Burger, Amino Acids, 1996, 11, 301, and M. W. Walter; R. M. Adlington; J. E. Baldwin; C. J. Schofield, J. Org. Chem., 1998, 63, 5179, all of which are incorporated herein by reference). Hence, efforts were directed to preparing different ammonium triflate salts for radiofluorination attempts.

Figure 34:
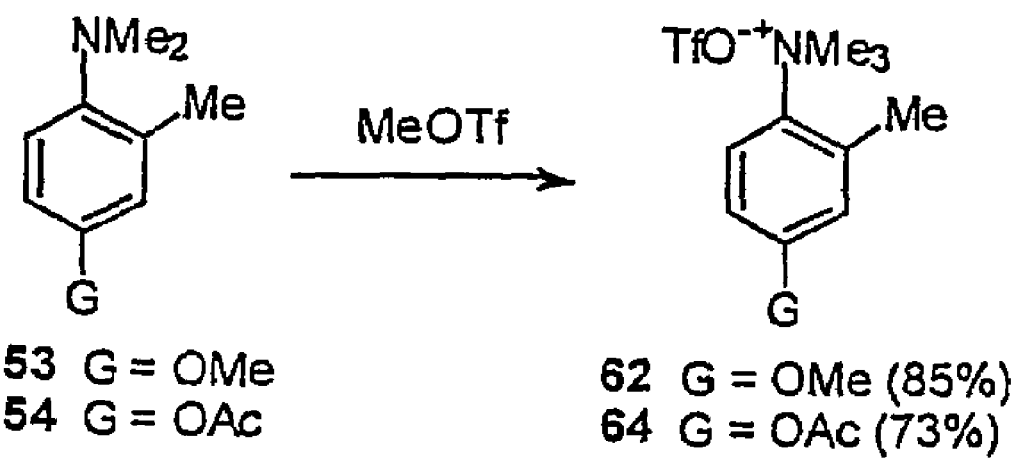
FIG. 34 illustrates preparation of Trimethylammonium Triflates 62 and 64.

As shown in FIG. 34, the synthesis of model compound 62 was quite facile and went to completion within fifteen minutes. Since compound 62 contained only a single site that could react with methyl triflate (MeOTf), the reaction was run overnight without the potential for adverse side reactions. However, this was not the case in the preparation of model compound 64. Proton NMR studies show that an undesired side product began to be formed after twenty minutes. Thus, if this reaction was allowed to proceed longer than 20 minutes, isolation of the trimethylammonium salt was very difficult. Thus, this reaction was promptly stopped after 20 minutes, quenched, and the product was recrystallized to generate crystalline product 64.

Figure 35:
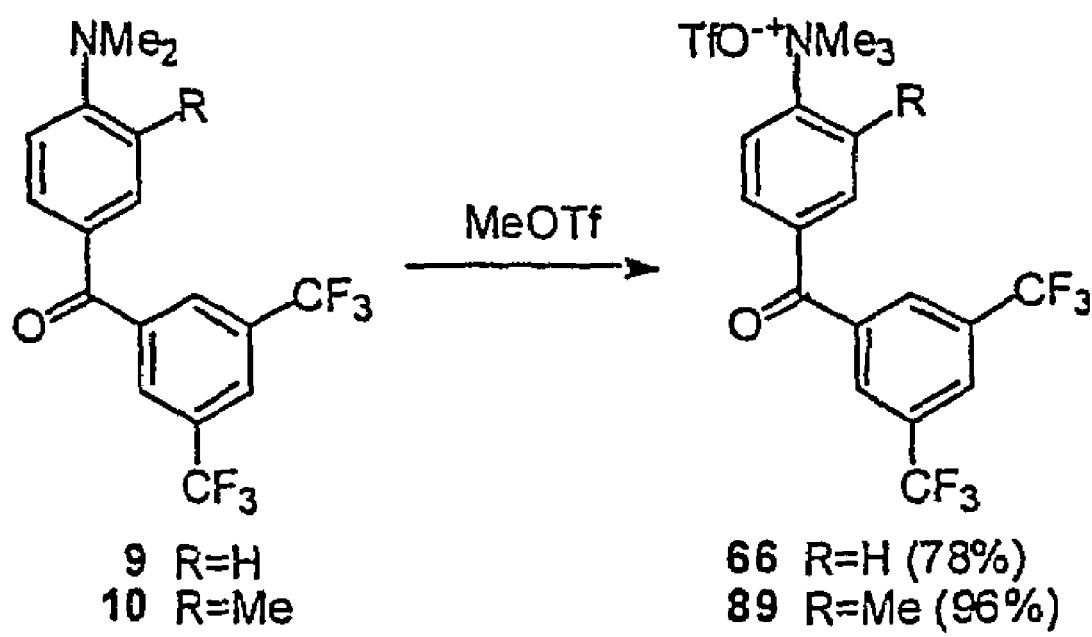
FIG. 35 illustrates preparation of Trimethylammonium Triflates 66 and 89.

Although there was some concern about potential O-alkylation on the non-enolizable carbonyl of compound (see FIG. 35), no side reactions were apparent by proton NMR studies. However, it was evident that a longer reaction time, nearly 36 hours at ambient temperature, was necessary for the reaction to reach completion and yield yellow crystals. The longer reaction was needed due to the decreased nucleophilicity of the amine caused by the para-positioned electron withdrawing group on the same aromatic ring. Since trimethylammonium triflates are thermally labile, attempts to use heat to increase the reaction rate were not pursued.

Figure 36:
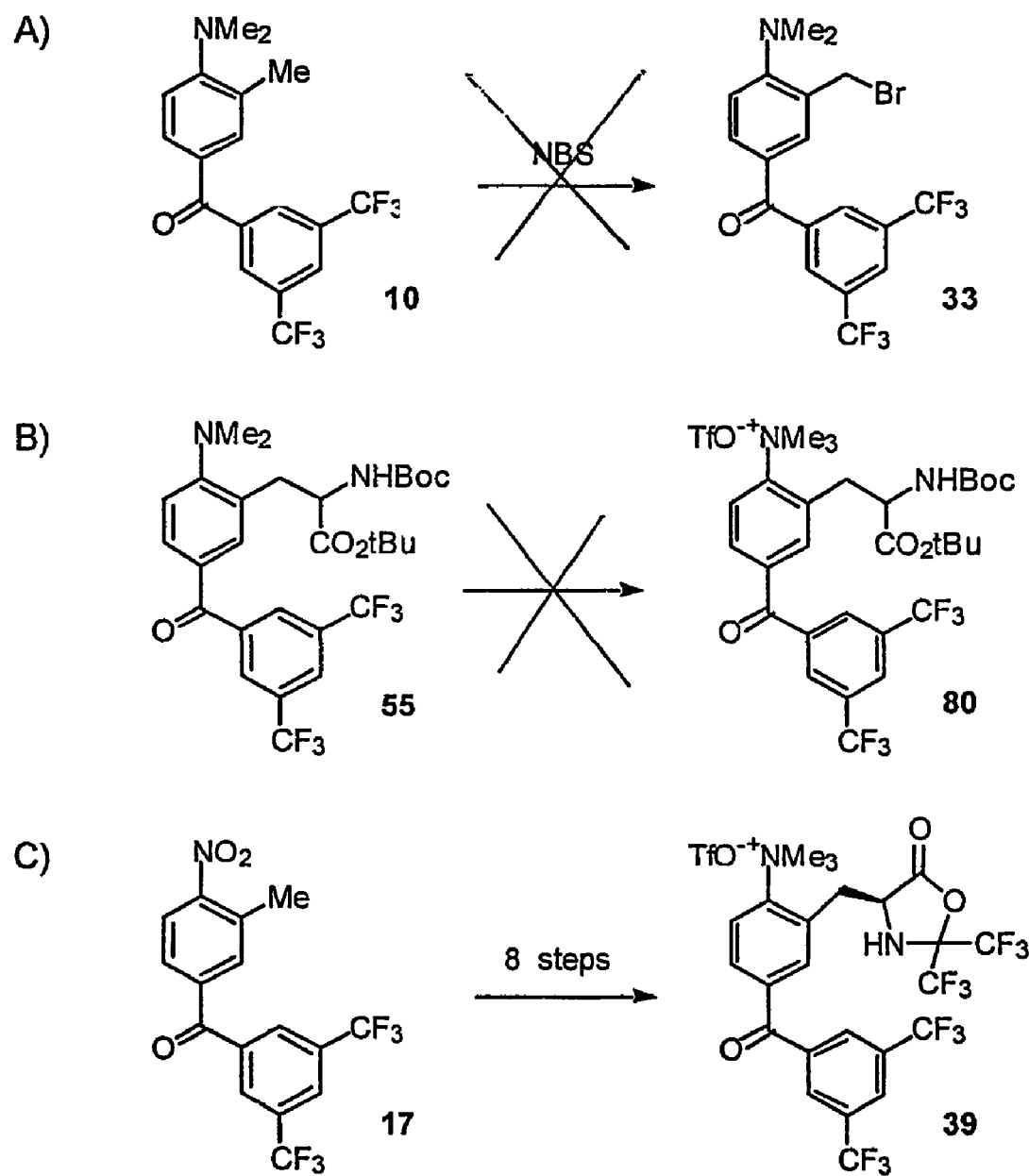
FIG. 36 depicts reactions A, B, and C.

As shown in FIG. 36, the next reaction was the synthesis of a trimethylammonium triflate salt with a diprotected amino acid scaffold. An indirect route to the target quaternary salt was pursued with compound 17 because in the original route the bromination step of compound 10 was problematic. Several transformations of compound 17 eventually gave compound 55 for quaternization. Unfortunately, compound 55 could not be quaternized, even after varying the MeOTf amounts, choice of solvents, and bases.

Figure 37:
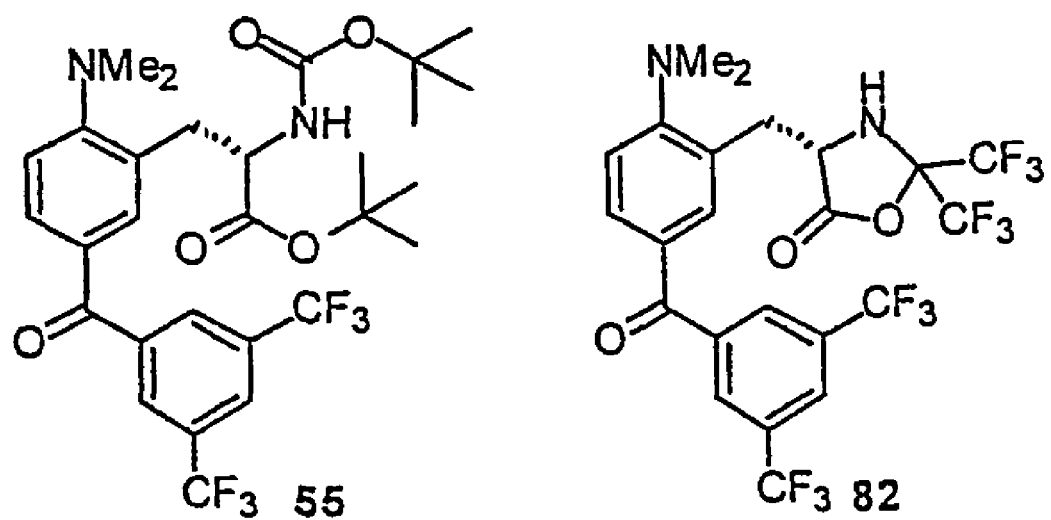
FIG. 37 illustrates the structures of compounds 55 and 82.

After proton NMR analysis, it was discovered that the Boc-protecting group of the amine was labile under the quaternization reaction with MeOTf and polar solvents. The starting material also decomposed when the MeOTf reaction was run neat. No reaction was observed with MeOTf or MeI in the presence of nonpolar solvents ($CH_2Cl_2$ or $CDCl_3$). There are several possible explanations for the unsuccessful quaternization. First, residual triflic acid, either present in the commercial grade methyl triflate or formed from methyl triflate and residual moisture in the solvent, might cleave the Boc-group and result in an unsuccessful quaternization in polar solvents. Secondly, amides, carbamates, and ureas can be O-alkylated, usually on the carbonyl oxygen. Polar solvents may amplify this undesired reaction. Thirdly, further examination of compound 55 (see FIG. 37) with Spartan® and Quanta®, two molecular modeling programs, (Spartan® Software, Version 1.0 from Wavefunction, Inc., 18401 Von Karmn, Suite 370, Irvine, Calif., 92715, and Quanta® Software, Version 4.0 from Molecular Simulations, Inc., 16 New England Executive Park, Burlington, Mass., 01803) demonstrated that in the lowest energy conformer the Boc-group crowds the area around the dimethylamino group. Both the AM1 and 321-G calculations were tried and carried out under vacuum conditions. 82 (see FIG. 37) clearly showed a more available $NMe_2$ group for nucleophilic attack of MeOTf when compared to 55. Thus, sterics may play a role in decreasing the reactivity of the center to be quaternized, especially in non-polar solvents.

Figure 38:
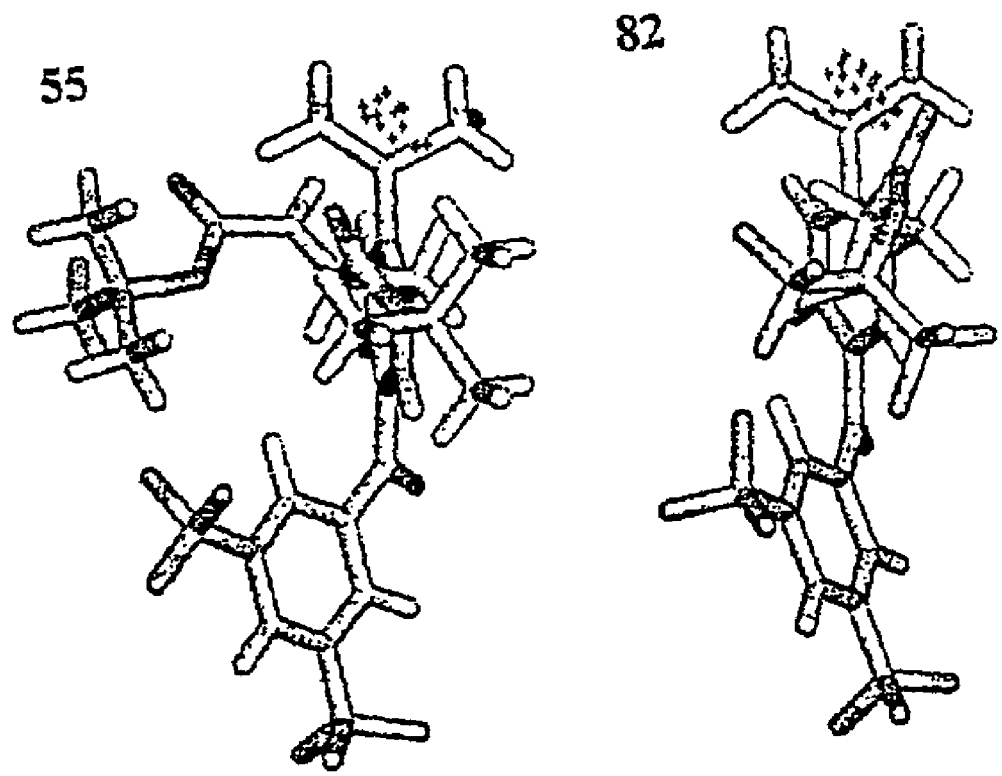
FIG. 38 is a schematic representation of a calculation of solvent-nitrogen atom interaction to predict nitrogen availability in compounds 55 and 82.

After 3-21G optimization was applied to compounds 55 and 82, the minimized conformers were exported into Quanta® software to obtain computed molecular properties, specifically the surface area for the solvent-atom interaction. Three radii (0.5, 1.0, and 1.5 Å from atom surface) were tried with 1.0 Å giving the best results. The respective computed outputs are illustrated in FIG. 38. Each displayed "+" around the dimethylamino-nitrogen atom in FIG. 38 represents a surface area of 0.1 $Å^2$ which the atom can interact with the solvent. Since compound 82 displayed 19 "+" symbols around the atom while 55 only showed 13, this indicates that more atom surface is exposed for 82 to participate in the quaternization reaction. Although the calculation is a rough estimation of the atom's nucleophilic availability to react with the electrophile, this may be a method to predict atom nucleophilicity in the future.

Figure 39:
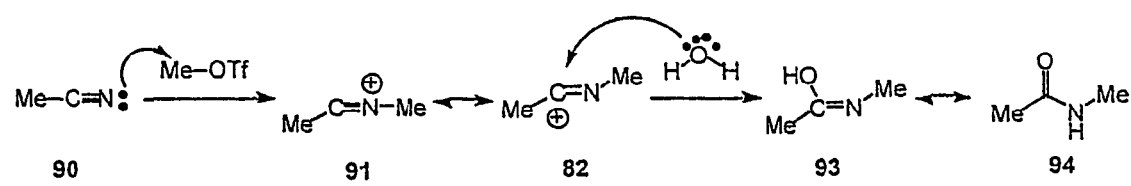
FIG. 39 is a representation of the undesired methylation of acetonitrile.

As shown in FIG. 39, another explanation for the unsuccessful quaternization reaction may be attributed to using an inappropriate solvent. Proton NMR analysis showed that MeOTf reacted with a solvent that was tried with this reaction, specifically acetonitrile. N-metyl-acetamide 94 was isolated and clearly made during the MeOTf reaction with acetonitrile. Such a side reaction with the solvent would use up MeOTf and prevent the quaternization reaction.

Figure 40:
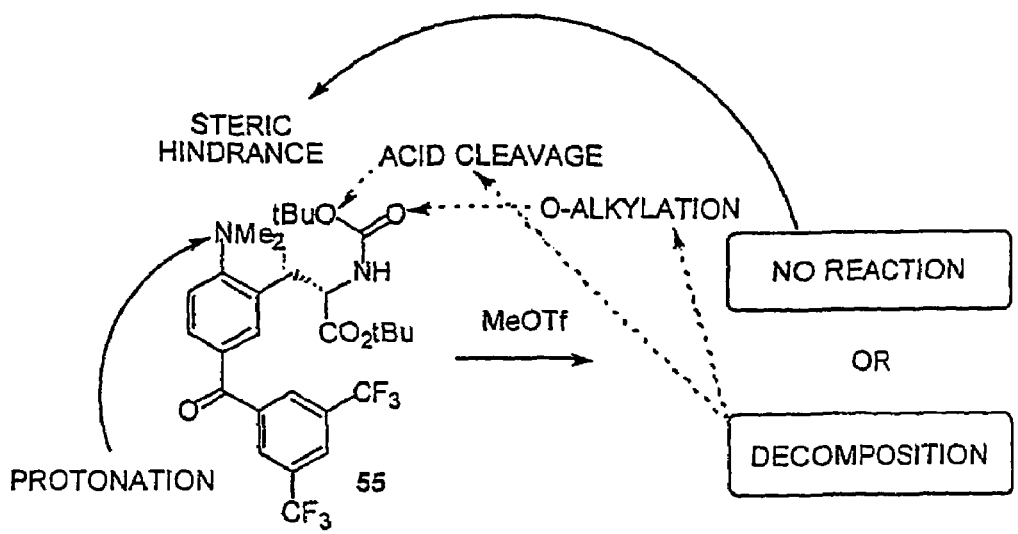
FIG. 40 depicts the attempted methylation of compound 55.

Since 2,6-di-tert-butyl-4-methyl-pyridine (DtBuMP) or diisopropylethylamine (DIEA) was added for trials 3, 5, and 6 and decomposition still occurred for 6 (see FIG. 40), it is possible that the problem was more a steric and O-alkylation one rather than one of acid lability. A solution to this problem included finding a diprotected amino acid scaffold that could tie back the amino and carboxylic acid groups away from the reactive center, survive mild acidic conditions, and eliminate the possibility for O-alkylation. In addition, the solvent problem could be avoided by running the reaction neat.

Figure 41:
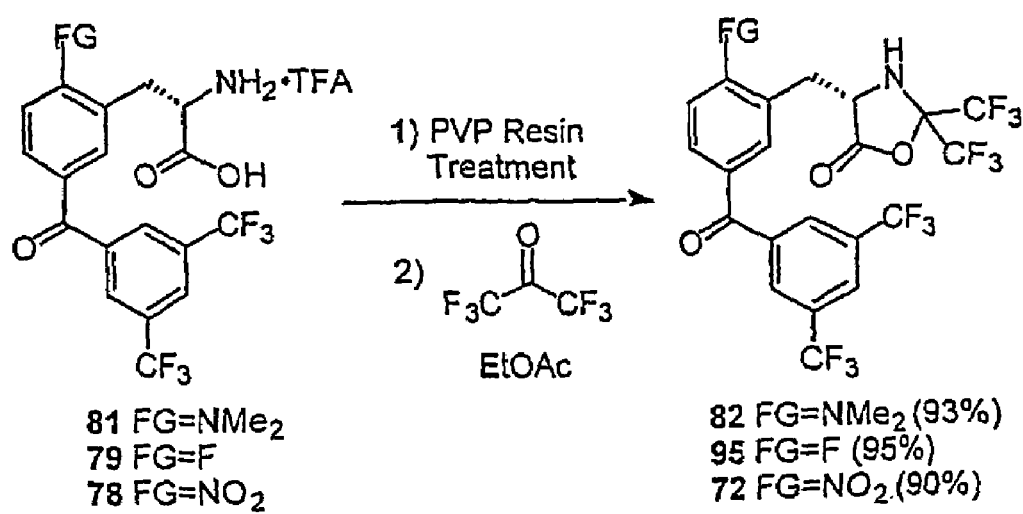
FIG. 41 is a representation of the preparation of HFA derivatives 82, 95, and 72.

One possible protecting group was hexafluoroacetone (HFA) protecting group (see F. Weygand; K. Burger; K. Engelhardt, Chem. Ber., 1966, 99, 1461, C. G. Krespan; W. J. Middleton, Fluorine Chemistry Reviews, 1967, 1, 145, G. R. Leader, Analytical Chemistry, 1970, 42(1), 16, C. Joy; W. Fraser; D. W. A. Sharp; G. Webb; J. M. Winfield, J. C. S. Dalton, 1972, 2226, F.-L. Ho, Anal. Chem., 1973, 45, 603, F.-L. Ho, Anal. Chem., 1974, 46, 496, K. Burger; M. Rudolph; E. Windeisen; A. Worku; S. Fehn, Monatshefte fur Chemie, 1993, 124, 453, K. Burger; H. Neuhauser; A. Worku, Z. Naturforsch, B: Chem. Sci. 1993, 48b, 107, K. Burger; E. Windeisen; R. Pires, J. Org. Chem., 1995, 60, 7641, R. Pires; S. Fehn; A. Golubev; D. Winkler; K. Burger, Amino Acids, 1996, 11, 301, M. W. Walter; R. M. Adlington; J. E. Baldwin; C. J. Schofield, J. Org. Chem., 1998, 63, 5179, all of which are incorporated herein by reference). The Boc- and t-butyl ester groups on 55 were easily removed with a sequential acid treatment of first 0.2 N HCl and then TFA to give compound 81 (see FIG. 41) as the protonated salt. An aqueous solution of the acid salt was passed repeatedly (10×) through a Reillex 425 polymer (poly-4-vinylpyridine cross-linked) column to trap the acid and give the free amino acid of compound 81. The free amino acid was treated with an excess of HFA (6.0 eq) in ethyl acetate and the reaction mixture was allowed to stir overnight in a sealed reaction vessel at 0° C. Compound 82 (see FIG. 41) was isolated as a yellow oil and used directly for the quaternization reaction. In addition, compounds 95 and 72 were synthesized for reference analysis and possible radiofluorination.

Once compound 82 had been prepared, quaternization reactions using $CDCl_3$ and $CD_3NO_2$ were attempted to see if the results would be different than those with compound 55. Again, no reaction was observed for the $CDCl_3$ procedure. However, if the MeOTf/CD$_3$NO$_2$/DtBuMP (2,6-di-tert-butyl-2-methyl pyridine) reaction was run for no more than 0.5 h, product formation was indicated by proton NMR. Unfortunately, product isolation could not be achieved due to the solvent CD$_3$NO$_2$. If allowed to react longer than 0.5 h, other side products that complicated the proton NMR spectrum began to form.

Since the diprotected amino acid scaffold effectively ties the two functionalities back from the reactive center and DtBuMP would neutralize any existing acid, the only issues to address were the resistance to O-alkylation and which solvent to use. The 2,2-bis(trifluoromethyl)-1,3-oxazolidin-5-one resembles a deactivated ester, which makes it a poor candidate for O-alkylation. The next step was to eliminate solvent use and run the reaction neat. Thus, trial 5 (see FIG. 42A) was conducted and some product formation was observed within 0.5 h at RT. Although trimethylammonium triflates are thermally unstable, trial 6 (see FIG. 42A) was attempted with heating to 70° C. to see if the reaction would be faster and better yields could be obtained. Trial 6 resulted in the formation of compound 39 as white crystals in 80% yield. Modifications to trial 6 led to trial 7, which used less MeOTf and base but gave comparable yields. Compound 39 was found to be stable at RT and have a long shelf life.

Figure 42B:
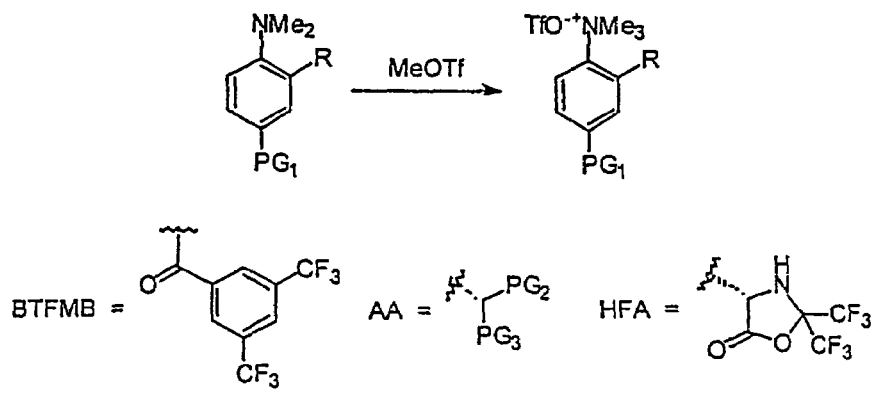
FIG. 42B depicts further methylation studies.

The quaternization studies indicate that both sterics and reactivity of the dimethyl amine play important roles in the success of the reaction. As shown in FIG. 42B, the highest yield was achieved for compound 53 when a methoxy group helped activate the ring unlike the other functionalities (i.e. —OAc, -BTFMB) that seem to lower the yield of each respective reaction. Large substituents that are positioned ortho to the amine also hinder the quaternization thus, these bulky protecting groups must either be changed or corraled away from the reactive center to allow this reaction to occur.

Baeyer-Villiger Oxidation

Figure 43:
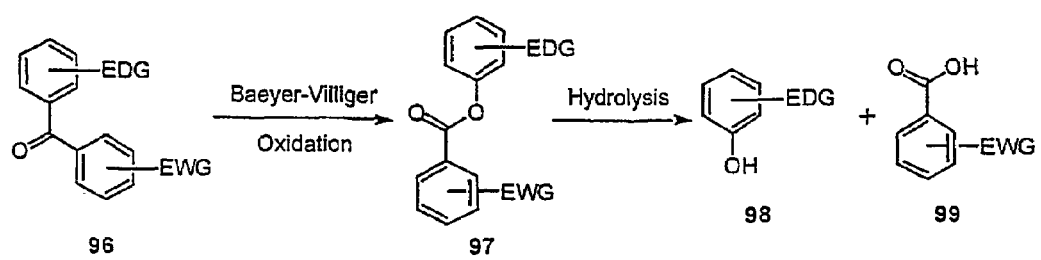
FIG. 43 depicts phenol product formed from Baeyer-Villiger Oxidation and subsequent hydrolysis.

Now referring to FIG. 43, Baeyer-Villiger oxidation of diaryl ketones 96 with peracids usually results in the formation of esters 97 and their hydrolysis products 98, 99 (see W. E. Doering; L. Speers, J. Am. Chem. Soc., 1950, 72, 5515, W. D. Emmons; A. F. Ferris, J. Am. Chem. Soc., 1953, 75, 4623, W. D. Emmons, J. Am. Chem. Soc., 1954, 76, 3468, H. Hart; C. A. Buehler, J. Org. Chem., 1964, 29, 2397, W. Adam; A. Rodriguez, J. Org. Chem., 1979, 44, 4969, S. A. Baldwin; M. T. Crimmins, J. Am. Chem. Soc., 1980, 30, 1198, R. Liotta; W. S. Hoff, J. Org. Chem., 1980, 45, 2887, E. G. Baggiolini; J. A. Iacobelli; B. M. Hennessy; A. D. Batcho, J. Org. Chem., 1986, 51, 3098, T. Honda; H. Ishizone; W. Mori; K. Naito; Y. Suzuki, J. Chem. Soc. Perkin Trans. I; 1991, 3027, L. Conte; M. Napoli; G. P. Gambaretto; A. Guerrato; F. M. Carlini, J. Fluorine Chem., 1994, 67, 41, and I. Ekaeva; L. Barre; M. C. Lasne; F. Gourand, Appl. Radiat. Isot., 1995, 46, 777, all of which are incorporated herein by reference). Thus, this reaction can transform the benzoyl functionality of a diaryl ketone 96 into the desired hydroxyl group by way of forming and then hydrolyzing the ester 97. In the cleavage of unsymmetrical ketones, the migrating group can be controlled by the location of the electron-donating and/or releasing groups on the aromatic rings.

Figure 44:
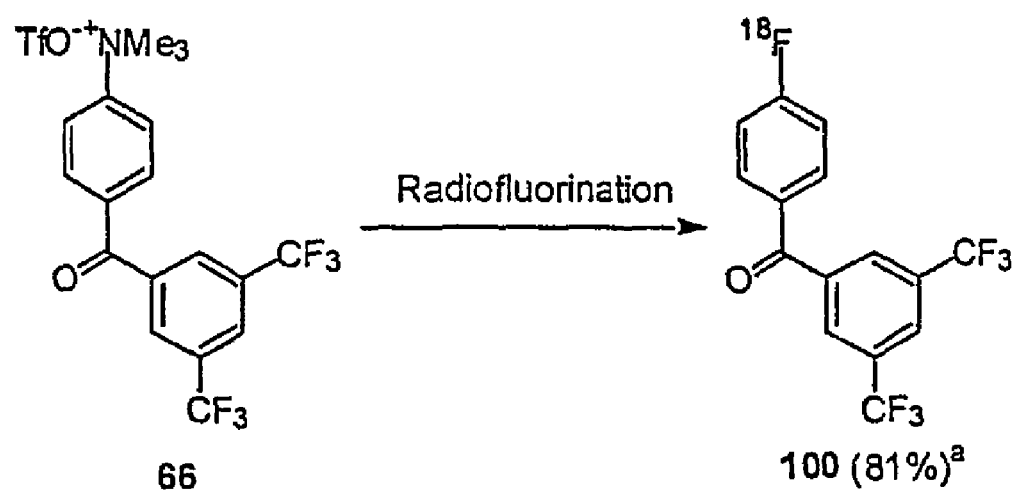
FIG. 44 illustrates radiosynthesis of compound 100 from 66.
Figure 45:
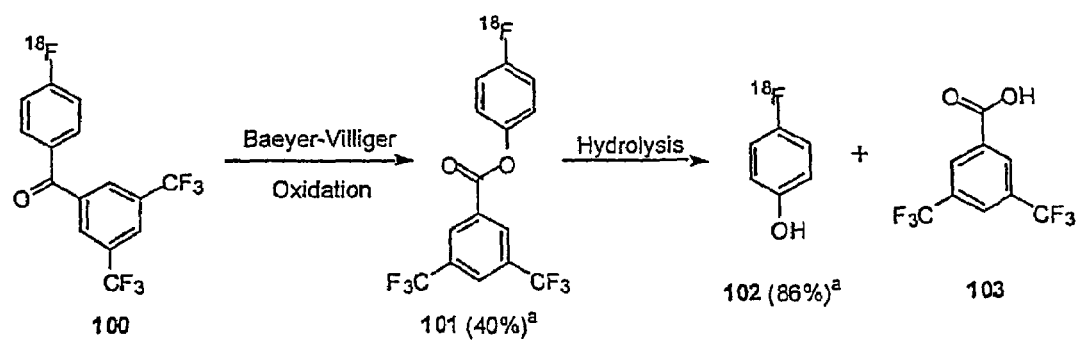
FIG. 45 illustrates radiosynthesis of compound 102 from 100.

Since radiofluorination was successful for compound 66 (see FIG. 44), initial Baeyer-Villiger studies were conducted on the "cold" fluorinated product 100 to obtain the respective ester and phenol products after hydrolysis (see FIG. 45). $^{19}$F-compounds 25 and 104 were prepared and 107 was purchased to serve as references for TLC and HPLC analysis. Once the reference compounds were available, the next step was to optimize the experimental conditions for the Baeyer-Villiger reaction.

Baeyer-Villiger reactions may be carried out using a variety of reagents and solvents (see D. Swern, Chem. Rev., 1948, 45, 1, C. H. Hassall, Org. Reactions, 1957, 9, 73, incorporated herein by reference). Hydrogen peroxide (H$_2$O$_2$), permono- and perdi-sulfuric acid (HSO$_5$H, HOSO$_5$H), peracetic acid (CH$_3$CO$_3$H), perbenzoic acid (PhCO$_3$H), and monoperphthalic acid (C$_6$H$_4$-1-CO$_3$H-2-CO$_2$H) have all been used as reagents for this type of reaction. Many common organic solvents are inert under the oxidative conditions but the choice is usually determined by the solubility of the reactants. In addition, acid catalysis and higher reaction temperatures can markedly reduce reaction times (see G. Barger, J. Chem. Soc., 1918, 113, 218, A. Ballio, Chem. Abs., 1952, 46, 2518, incorporated herein by reference). Since shorter reaction times are obviously preferred during a radiochemical synthesis, these conditions were employed when determining the final experimental conditions.

Once 100% incorporation of the $^{18}$F-radiolabel was achieved with the model precursor, the Baeyer-Villiger oxidation was selected to transform the ketone functionality to an ester that would lead to the desired phenol. Three Baeyer-Villiger conditions were tried: 1) acetic acid, 40% peracetic acid, H$_2$SO$_4$, 2) MCPBA, TFAA, TFA, and 3) 30% H$_2$O$_2$, TFA, TFAA. Initially, radio-TLC analysis suggested that all three conditions either resulted in no oxidation of the ketone or that the ester had an identical retention time as the ketone. After further analysis of the TLC results with the reference compounds, it was apparent that both the ketone and ester ran with the solvent front when 100% diethyl ether was used as the mobile phase. Thus, the TLC system was optimized for this reaction as shown in FIG. 46. A study was performed on the $^{19}$F-compounds and the third Baeyer-Villiger conditions were chosen based on convenience.

Figure 47:
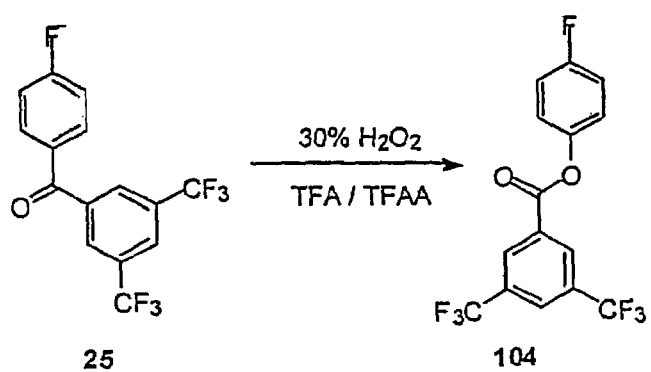
FIG. 47 depicts the optimization of Baeyer-Villiger reaction on compound 25.

After several trials, it was determined that a 10:3 hexane/CH$_2$Cl$_2$ (see FIG. 46) TLC solvent system was optimal for following the progress of the Baeyer-Villiger reaction. In addition, a more polar solvent system (4:1 hexane/EtOAc) was needed to follow the hydrolyzed product, 4-fluorophenol. Reactions were followed by qualitative estimation of the UV absorbance intensity on TLC as shown in FIG. 47. Experiment #1 required three hours at ambient temperature to go to completion, which was unacceptable for the radiosynthetic route. For experiment #2, the reaction temperature was increased to 50° C., which reduced the reaction time to 1.2 h. Although temperatures above 45° C. normally lead to excessive decomposition of peroxides, there are exceptional cases where the oxidation of aromatic aldehydes and ketones have been successfully carried out at higher reaction temperatures and shorter reaction times. Thus, experiment #3 was run at 80° C. and the reaction was completed within 30–40 minutes, which is an acceptable time for the radiochemical synthesis.

Figure 48:
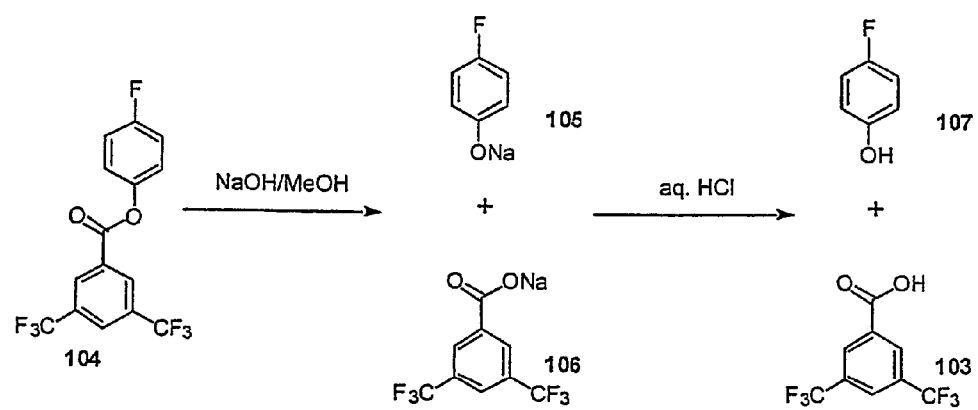
FIG. 48 depicts the hydrolysis of compound 104 to form 107.

Treatment of the ester with aqueous NaOH had no effect on the ester functionality, which was later determined to be a solubilty issue. Thus, as shown in FIG. 48, the ester was treated with a methanolic NaOH solution and hydrolysis was nearly quantitative. The sodium phenoxide derivative was then quenched with acid to give the desired product.

Figure 49:
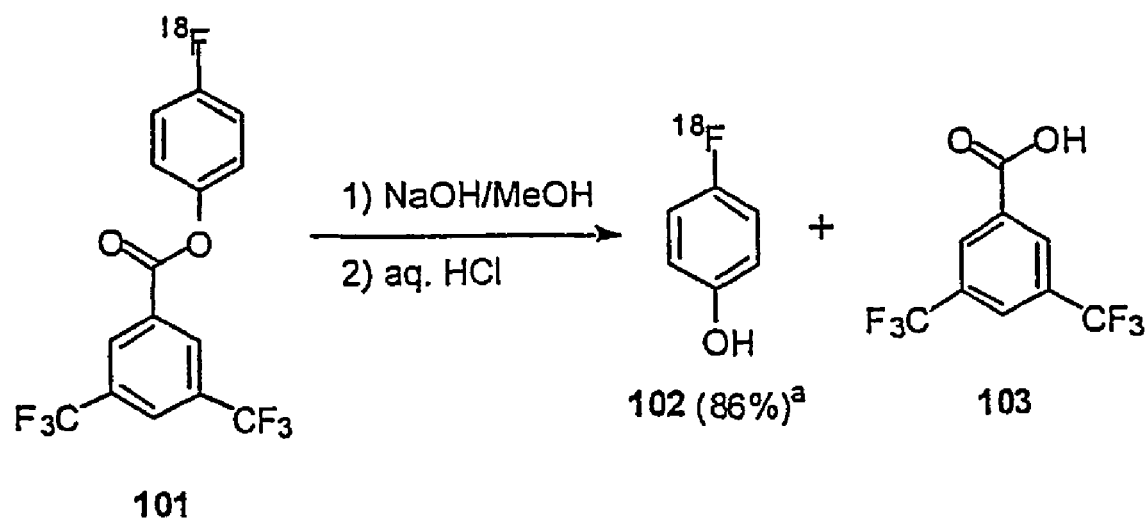
FIG. 49 depicts the hydrolysis of compound 101 to form 102.

Once the final oxidative conditions were set, the next step was to conduct the reaction with the radiolabelled product. The reaction was followed by radio-TLC and the reaction went to completion within 45 minutes. As illustrated in FIG. 49, hydrolysis of the ester was accomplished using NaOH/

Figure 50:
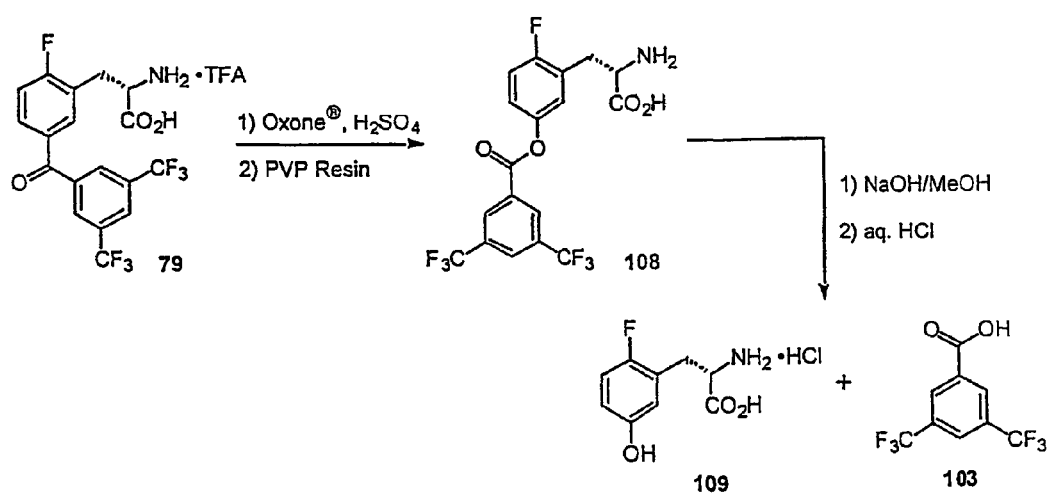
FIG. 50 illustrates the synthesis of compound 109 from 79.

MeOH and then the product was reacidified with HCl to give the desired 4-[$^{18}$F]-fluorophenol. As shown in FIG. 50, the next Baeyer-Villiger reaction was with the $^{19}$F-amino acid derivative 79. Although the reaction did work using the previous conditions, inconsistency from one reaction to the next was observed. Thus, the decision was made to try Oxone® (potassium monoperoxysulfate, 2KHSO$_5$.KHSO$_4$.K$_2$SO$_4$), a commercially available solid reagent that could be weighed, with concentrated H$_2$SO$_4$ for the Baeyer-Villiger reaction. Three temperatures (0° C., RT, and 80° C.) were tried. At 80° C., the reaction was complete within 30 minutes with signs of hydrolysis because formation of the benzoic acid was observed by HPLC.

Radiofluorination Studies

Aromatic radiofluorinations can occur by two major routes, electrophilic and nucleophilic substitutions. Since most medical cyclotrons supply only the [$^{18}$F]-fluoride ion, a nucleophilic fluorination route is a desirable approach to providing a variety of useful [$^{18}$F]-fluorophenol-containing radiotracers. Heretofore, there have been a number of efforts to develop nucleophilic routes, however these efforts have fallen short of providing a simple, practical method or producing these radiotracers routinely for clinical use. Current routes for a number of these molecules involve the use of electrophilic fluorinating reagents such as [$^{18}$F]-labeled elemental fluorine or acetyl hypofluorite (CH$_3$CO$_2$F), but these routes often result in low specific activity and mixtures of fluorinated products. For these reasons, the present invention is directed to an efficient and practical means to supply these radiotracers routinely via nucleophilic radiofluorination.

Two radiolabeling methods were investigated to carry out nucleophilic aromatic radiofluorination: 1) solid-phase synthesis and 2) solution-phase methods. Nitrobenzenes (such as 17) (see Y. S. Ding; C. Y. Shiue; J. S. Fowler; A. P. Wolf; A. Plenevaux, *J. Fluorine Chem.*, 1990, 48, 189, Y. S. Ding; J. S. Fowler; S. J. Gatley; S. L. Dewey; A. P. Wolf, *J. Med. Chem.*, 1991, 34, 767, P. K. Chakraborty; M. R. Kilbourn, *Appl Radiat. Isot.*, 1991, 42, 673, P. K. Chakraborty; M. R. Kilbourn, *Appl. Radiat Isot.*, 1991, 42, 1209, K. Hashizume; H. Tamakawa; N. Hashimoto; Y. Miyake, *Appl. Radiat Isot.*, 1991, 42, 1209, Y. S. Ding; J. S. Fowler; S. J. Gatley; S. L. Dewey; A. P. Wolf; D. J. Schlyer, *J. Med. Chem.*, 1991, 34, 861, Y. S. Ding; J. S. Fowler; A. P. Wolf, *J. Label Cmpds. Radiopharm.*, 1993, 33, 645, and H. Clark; D. Wails, *J. Fluorine Chem.*, 1995, 70, 201, all of which are incorporated herein by reference) and aryl trimethylammonium triflates (such as 110) (see M. S. Haka; M. R. Kilbourn; G. L. Watkins; S. A. Toorongian, *J. Labeled Compds. Radiopharm.*, 1989, 27, 823, and G. K. Mulholland, *Appl. Radiat Isot.*, 1991, 42, 1003, and P. Damahut; C. Lemaire; A. Plenevaux; L. Christiaens; D. Comar, *Tetrahedron*, 1997, 53, 5785, all of which are incorporated herein by reference) serve as excellent substrates for both radiofluorination methods.

For the solid-phase methodology,(see G. K. Mulholland; M. R. Kilbourn; D. M. Jewett, *J. Nucl. Med.*, 1991, 32, 1010, incorporated herein by reference) the requisite triflates were readily prepared from the corresponding nitro/amino group and the triflate ion was easily exchanged for [$^{18}$F]fluoride ion. After ion-exchange with the resin, the resulting trimethylammonium [$^{18}$F]fluoride was heated, causing an intramolecular displacement of the neutral gaseous leaving group, trimethylamine. The resulting [$^{18}$F]-substituted aromatic is free of high-boiling solvents or additives (e.g. crown or kryptand). Thus, the solid-phase reaction is an efficient method for radiofluorination.

On the other hand, solution-phase reaction, the traditional method, avoided using resins that could cause problems due to the solvent-dependent shrinking and swelling characteristics of the resin. In some instances, resin fragments become deactivated upon heating (near 100° C.) and decompose over time. Hence, herein radiofluorination attempts usually began using the solution phase method, since this allows for more robust conditions.

Figure 51:
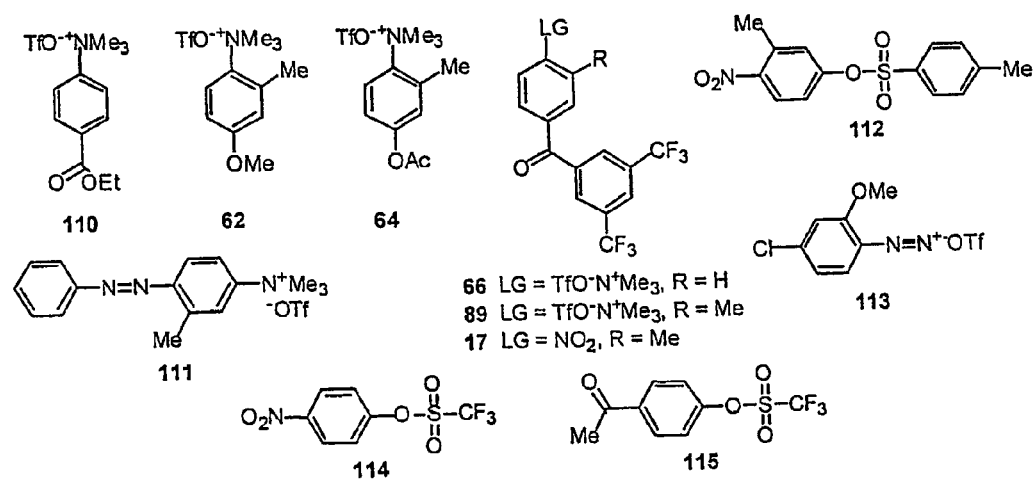
FIG. 51 depicts compounds for radiofluorination.

The present invention provides an approach to the model compound 4-[$^{18}$F]-fluorophenol. Commercially available starting materials were used either directly or converted to the desired substrates. These various substrates were then subjected to nucleophilic radiofluorination conditions. As shown in FIGS. 50 and 51, different activating and leaving groups were compared to observe their ability to facilitate [$^{18}$F]fluoride incorporation. An electron-withdrawing group situated ortho or para to the leaving group is necessary for [$^{18}$F]-nucleophilic substitution to occur. The nature of the electron-withdrawing group influences the degree of fluoride incorporation. In this case, the bis-(trifluoromethyl) benzoyl functionality is needed to sufficiently activate the aromatic system for nucleophilic fluorination.

Figure 53:
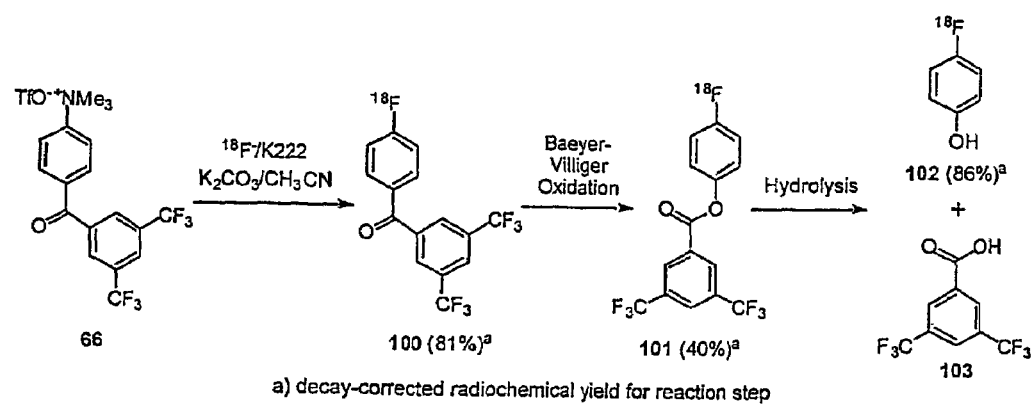
FIG. 53 depicts the synthesis of p-[$^{18}$F]-Fluorophenol.

Unlike the other precursors that contained weaker activating groups, which displayed either no or lower [$^{18}$F]-incorporation, the benzophenone derivative 66 afforded the best radiofluorination yields (81%; see FIG. 52). As illustrated in FIG. 53, after radiofluorination of the selected 4-[$^{18}$F]-fluorophenol precursor 66, the subsequent Baeyer-Villiger oxidation of the ketone and hydrolysis of the ester yielded p-[$^{18}$F]-fluorophenol 102 in 27% overall radiochemical yield.

Figure 54:
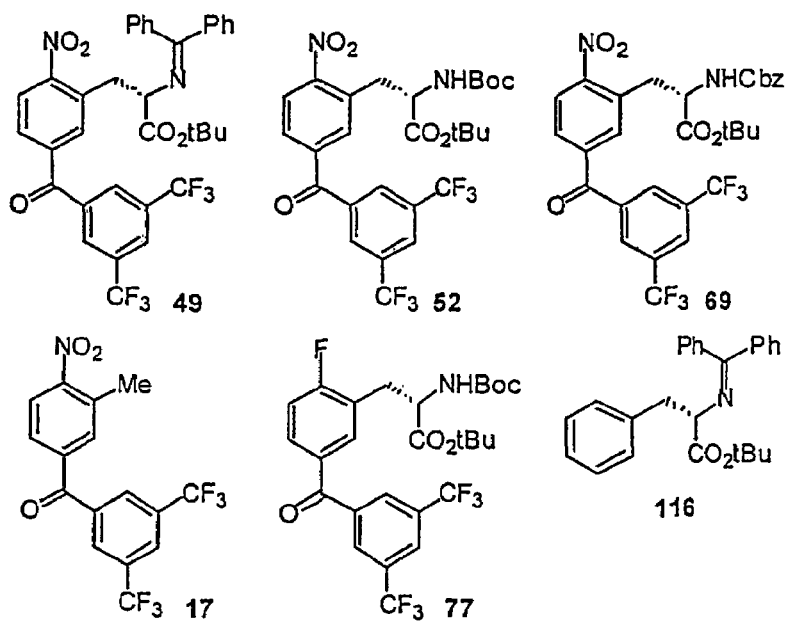
FIG. 54 depicts nucleophilic radiofluorination of various precursors to 6-[$^{18}$F]-FMT 132.

Once the radiofluorination procedure was established for the model compound to give 4-[$^{18}$F]-fluorophenol, the next step was to apply this procedure to a similar precursor containing a diprotected amino acid moiety. Now referring to FIG. 54, five compounds 49, 52, 69, 77 and 116 were prepared in order to examine the radiofluorination potential of the leaving group (nitro or $^{19}$F-fluoride) and the stability of different protecting groups, specifically a diphenyl imine, t-butyl carbamate(Boc), benzyl carbamate (Cbz), and t-butyl ester, to the reaction conditions. The reaction with 49 showed virtually no incorporation when analyzed by radio-TLC. Both 52 and 69 gave [$^{18}$F]-fluoride incorporation with 52 giving the best radiolabeling yield. In the reaction with 77, radio-TLC and stack monitor indicated that all the activity was in the form of inorganic fluoride and that no activity was lost due to volatiles. 116 was used solely as a control to see if the nucleophilic fluoride would react with either protecting group. This study suggested that the nitro group was not an effective leaving group for this class of compounds and that the protecting groups on 52 facilitate better fluoride incorporation.

Figure 55:
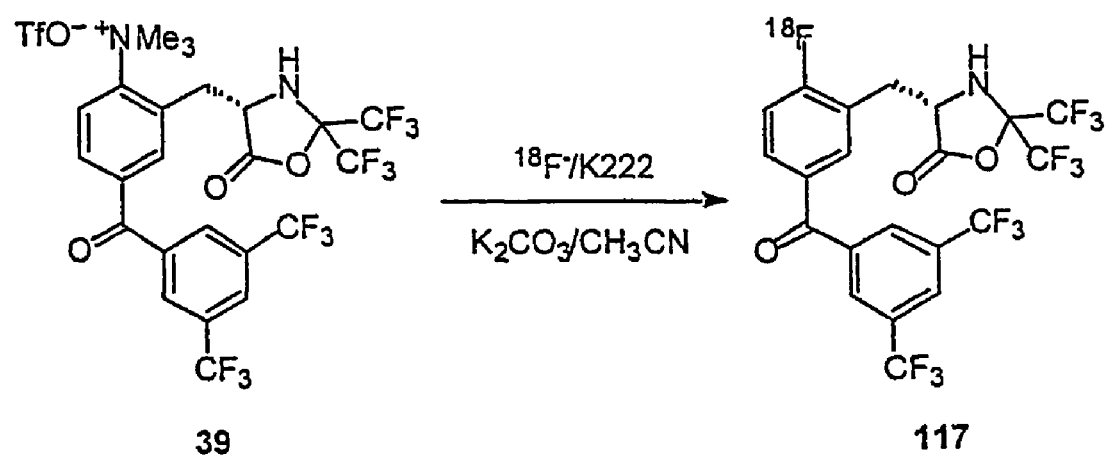
FIG. 55 depicts radiofluorination of compound 39 to 117.
Figure 56:
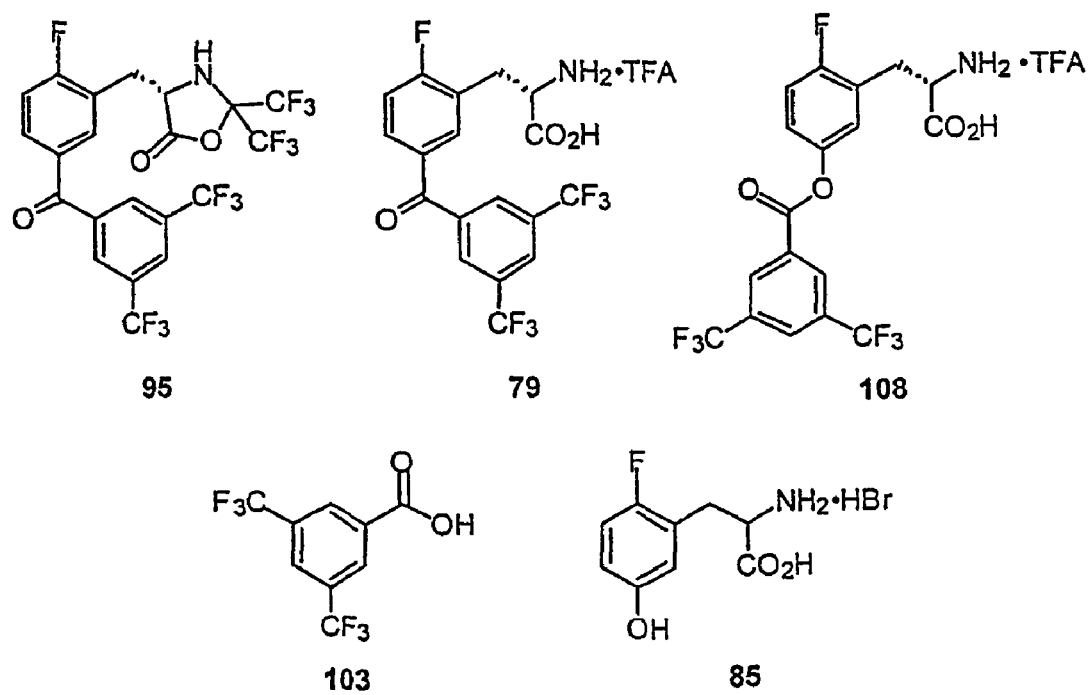
FIG. 56 illustrates reference compounds prepared for studies of the radiofluorination of compound 39.

As previously discussed, the synthesis of the next target compound 80, was not successful. However, as illustrated in FIG. 55 compound 39 was made and then subjected to the set radiofluorination conditions. The reaction was monitored by radio-TLC. After 15 minutes at 100° C., analysis indicated that inorganic fluoride was being consumed and a single peak began appearing near the solvent front (95:5 CH$_3$CN/H$_2$O mobile phase). A less polar developing solvent (1:1 hexane/EtOAc) was tried to see if the new peak was one of several products. Unfortunately, the second TLC system did not resolve the compound(s) and gave little additional information. However, HPLC analysis (2:2:1 CH$_3$CN/MeOH/20 mM NaH$_2$PO$_4$, 220 nm, 1.0 mL/min) did indicate that the apparent single peak, observed with the CH$_3$CN/H$_2$O TLC system, contained multiple compounds. None of the HPLC peaks (R$_t$=3.35, 8.03, 12.34, 15.28, 16.72, 18.54, 21.78, 23.56 min) matched the retention times of any of the authentic reference compounds 95, 79, 108, 103, or 85 that were made (see FIG. 56; also see FIG. 57 for HPLC data reference compounds).

Figure 58:
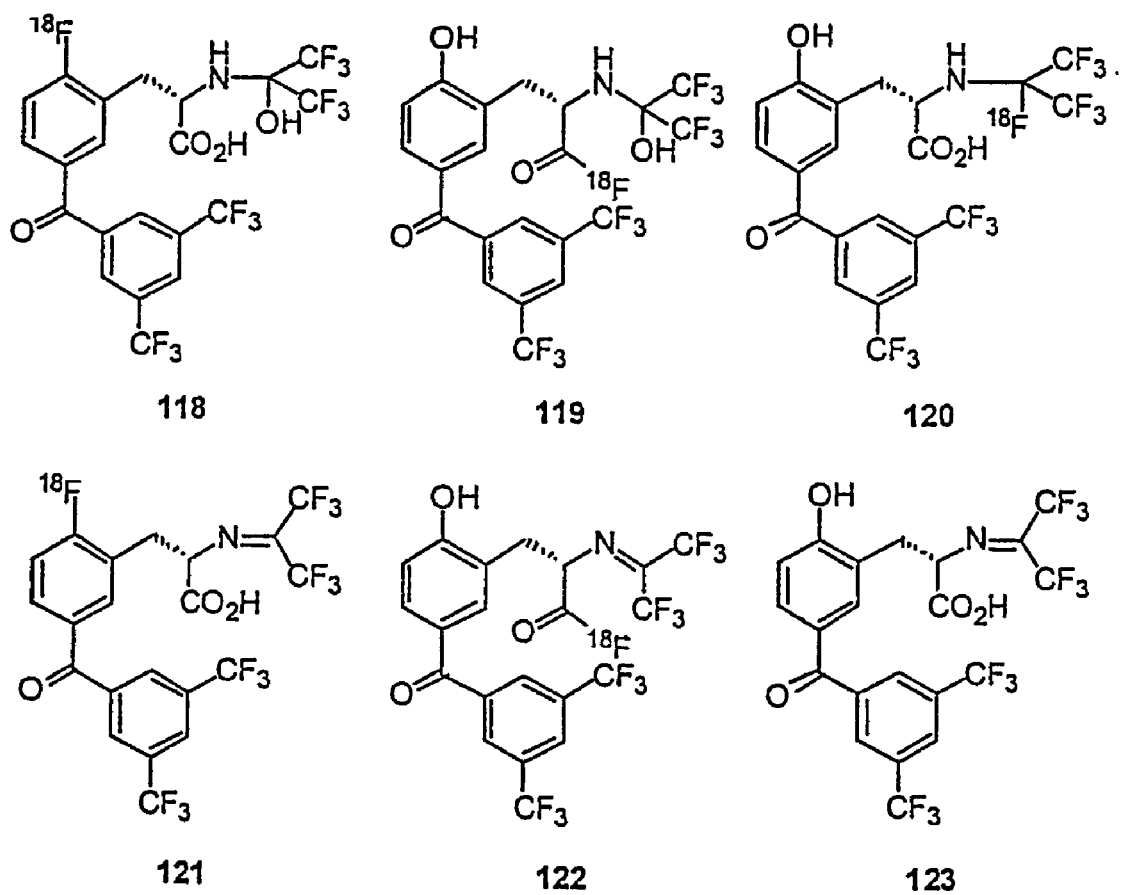
FIG. 58 shows possible radiofluorinated monomers derived from 39.

Compounds 118–123, shown in FIG. 58, are possible candidates for the unknown peaks that eluted off before 95. Ring opening caused by nucleophilic attack from either fluoride or carbonate could give rise to compound 120 and hemiaminals 118 and 119. Subsequently, these N-substituted hemiaminals could lose water and afford the respective imines. Further analysis suggests that the peaks eluted after 95 are more lipophilic and may be dimers (124–129) (see FIG. 59) or trimers of the desired product 117 that are formed by the nucleophilic phenol attacking various potential electrophilic centers on 39.

Since the radiochemistry occurs at a nano to picomolar scale, the products from the radiofluorination attempt of 39 were characterized by chromatographic properties and chemical partitioning behavior.

NaOH/MeOH was added to the crude radiofluorinated mixture to see if this would change the behavior of the radioTLC. No change was observed, indicating that the radiofluorinated molecule(s) did not contain any acyl fluoride. Third, the radiofluorinated mixture was treated with concentrated HCl which also had no effect on the radioTLC. This indicated the absence of free amines and, therefore, the molecule was nonbasic. Interestingly, heating with concentrated acid under forcing conditions to attempt to open a presumed intact HFA ring only yielded loss of radioactivity as volatility.

Figure 60:
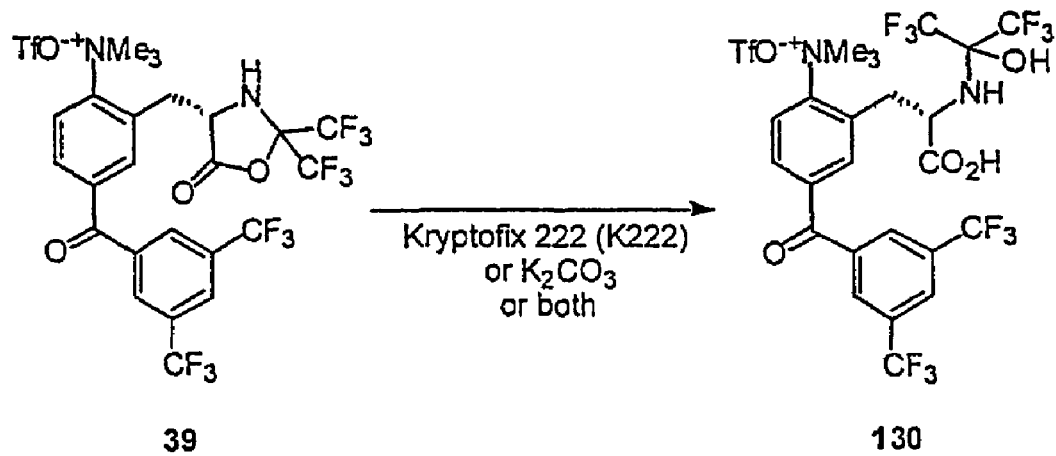
FIG. 60 depicts fluorine-NMR study of HFA-Acetonide protecting group.

Fluorine NMR studies were also completed to study the stability of the HFA-acetonide ring. As shown in FIG. 60, different combinations of Kryptofix 222 and K$_2$CO$_3$ were added to 39 and then the reaction mixtures were monitored by $^{19}$F-NMR. The NMR spectra show a disappearance of the two quartets, that are present for the bis(trifluoromethyl) groups on the HFA-acetonide, when Kryptofix 222 was added to 39. The loss of these peaks indicated a reaction of 39, most likely the opening of the acetonide ring. Both Kryptofix 222 and K$_2$CO$_3$ were required for the ring opening reaction to occur. Consequently, it was thought that decreased amounts of both Kryptofix 222 and K$_2$CO$_3$ might minimize the number of side products created by the ring opening of the HFA-acetonide during the radiofluorination of 39.

The next radiofluorination attempt used a 13:1 precursor to K$_2$CO$_3$ ratio. In addition, the heating temperature was also lowered to minimize potential dimerization and trimerization. Both modifications decreased the fluoride incorporation and increased the available inorganic fluoride. Furthermore, these modifications reduced the number of radiofluorinated products to only one, as observed by a single peak in the radioTLC. The subsequent HPLC analysis of this reaction also showed fewer peaks (tr=3.34, 5.29 min) that did not match up with any compounds listed in FIG. 56.

A second heating cycle (30 min at 100–140° C.) was carried out under forcing conditions to see if a change could be made. More inorganic fluoride was consumed with an increase in fluoride incorporation. However, the additional heating did not change the TLC patterns in either TLC system. Purification with the cation exchange/neutral alumina column provided a cleaner mixture of radiofluorinated product to inorganic fluoride. TLC development of the same mixture using 95:5 CH$_3$CN/H$_2$O moved a small peak from the origin to higher up on the plate. Several other conditions were attempted to try to overcome these problems. The radiofluorinated products were minimized but it was concluded that the HFA-acetonide protecting group would not survive the fluorination conditions and another amino acid protecting group would be needed.

Final Route

The synthetic pathway to the desired radiotracer can be divided into two stages: preparation of the radiofluorination precursor 39 and radiofluorination and subsequent deprotection to form 6-[$^{18}$F]-fluoro-meta-tyrosine (6-[$^{18}$F]-FMT, 132). It should be appreciated that this final route overcomes previous limitations in the preparation of 6-[$^{18}$F]-FMT by using the nucleophilic radiofluorination method and employing the conventional targetry found with the medical cyclotron. Furthermore, it should be appreciated that the approach of the present invention to 6-[$^{18}$F]-FMT incorporates the F-18 in the pentultimate step and gives the radiotracer in high yield and specific activity.

Figure 61:
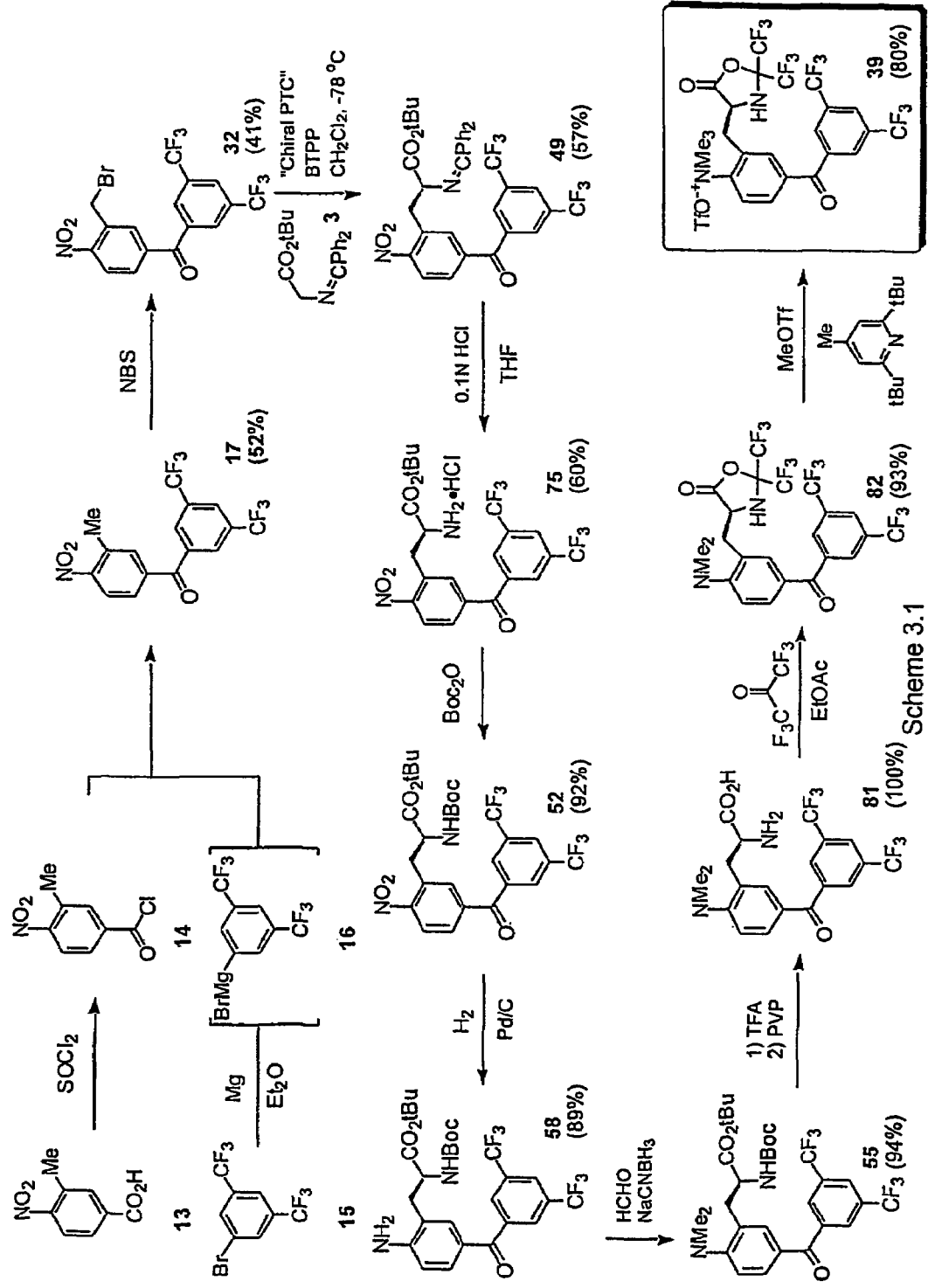
FIG. 61 illustrates the preparation of radiofluorination precursor compound 39.

As shown in FIG. 61, in the first stage, the benzylic halide 32 is prepared from two commercially available starting materials, 3-methyl-4-nitrobenzoic acid 13 and 3,5-bis(trifluoromethyl)bromobenzene 15. Carboxylic acid 13 was treated with thionyl chloride to give the resulting acid chloride 14, which was immediately reacted with the Grignard reagent derived from 15. This Grignard reaction afforded the benzophenone derivative 17, which was then subjected to a benzylic bromination using N-bromo-succinimide to give the benzylic halide 32.

Preparation of the radiofluorination precursor 39 involved four key transformations of benzylic halide 32. First, an amino acid side chain was extended from the carbon framework of 32 using a chiral-phase transfer catalysis process to give the alkylated product 49 with a new stereogenic center at the α-carbon. After hydrolysis of the imine and reprotection as the Boc derivative (49 to 52), the second set of transformations converted the aromatic nitro group of 52 to the dimethylamino group in 81. Third, the amino acid 81 was treated with hexafluoroacetone in EtOAc solvent to give the hexafluoroacetone acetonide 82. Lastly, the dimethylamino group of 82 was quaternized with methyl triflate, in the presence of the hindered base 2,6-di-tert-butyl-4-methylpyridine, to give the trimethylammonium triflate salt 39, an excellent leaving group, for nucleophilic fluoride displacement in the next step.

Figure 62:
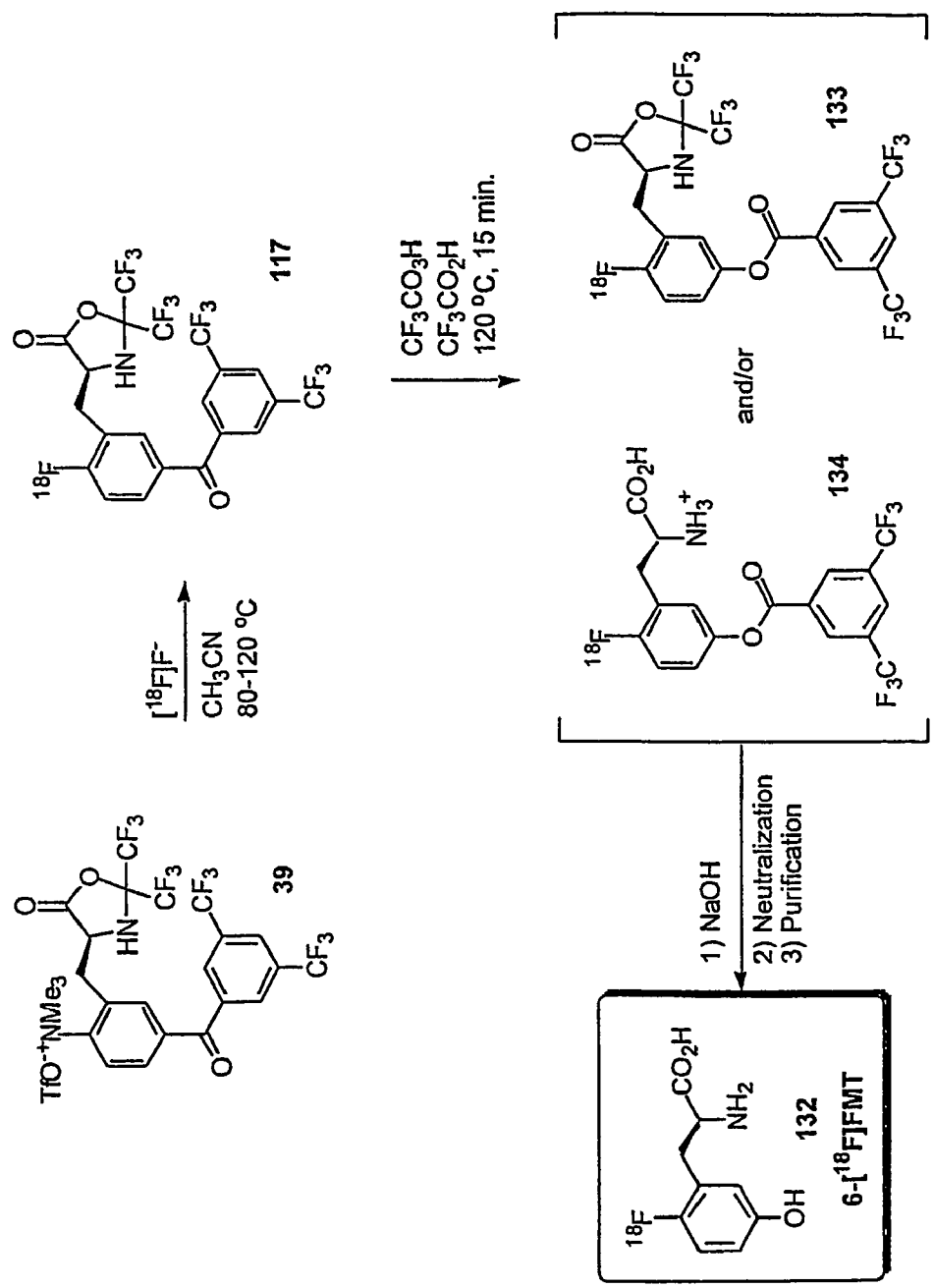
FIG. 62 illustrates the radiofluorination and deprotection of 39 to form 6[$^{18}$F]-FMT.
Figure 63:
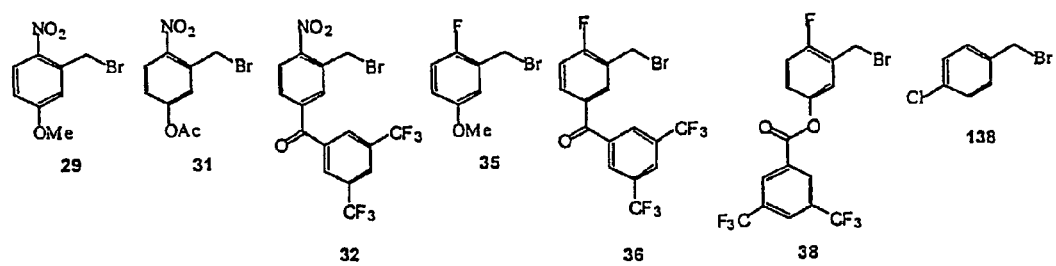
FIG. 63 illustrates benzyl bromide derivatives used for PTC reactions.

As shown in FIG. 62, the second stage involved the radiofluorination of the precursor 39. [$^{18}$F]-Radiolabel incorporation onto the functionalized benzophenone structure of 39 involves anhydrous, no-carrier added (NCA), soluble [$^{18}$F]-fluoride in acetonitrile at moderate temperatures (80–100° C.) for short times (15–30 min). The [$^{18}$F]-fluoro-intermediate 117 is purified by rapid solid-phase purification techniques and the bulk solvent was removed. The ketone functionality of 117 can be converted to an aryl benzoyl ester 133 under Baeyer-Villiger conditions, which also partially deblocked the molecule. Concentrated aqueous NaOH is used to carefully saponify the ester 133 and then the mixture is neutralized and subjected to a rapid solid-phase purification to afford the final purified radiotracer 6-[$^{18}$F]-FMT 132. The desired total radiosynthesis time from end-of-beam (EOB, the point of [$^{18}$F]-fluoride production) was about sixty minutes.

Figure 64:
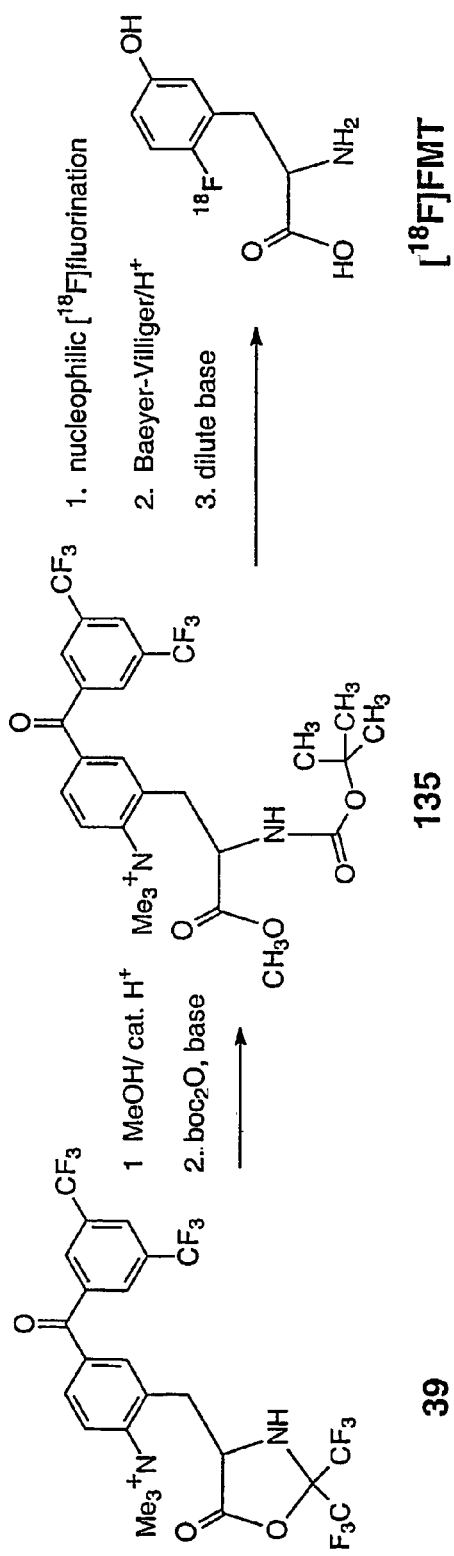
FIG. 64 illustrates the preparation of radiofluorination precursor compound 135 and [$^{18}$F]-FMT.

Another compound of the present invention which can be utilized as a stable precursor for the purpose of radiofluorination is compound 135 as shown in FIG. 64. Compound 135 is synthesized in the following manner.

Compound 39 (100 mg) was stirred at room temperature in a solution of trifluomethanesulfonic acid (100 uL) in anhydrous methanol (1 mL). The reaction was monitered by HPLC (4.6×250 mm C-18; 1.5 mL/min 3:1:1 CH3CN: MeOH: 20 mM pH 6.7 KHPO$_4^-$; UV 220 nm) for dissappearance of 39 (rt 4.95 min and the formation of the methyl ester, free amino intermediate (rt 3.5 min) which was not isolated. When the reaction was complete, the acid was removed by passing the reaction solution through a 2 cm×1 cm pad of reillex 425 polyvinylpyridine (PVP) resin at 0° C., allowing it to stand on the resin for 10 min at 0° C. for 5 min and then rinsing the PVP pad with dry, 0° C. acetonitrile (~5–10 mL). The combined organic extracts(pH 5–7 when applied to water-wetted pH paper) were concetrated quickly to ~½ original volume under reduced pressure while keeping cold, and the concntrate was reacted (0°–rt) with Boc$_2$O (3×0.15 g), until all all of the amino acid methyl ester intermediate (rt 3.5 min) had been converted to 135 (rt 4.5 min) and a small amount of dimer side product (rt 6.33). The reaction mixture was worked up by concentration at room temperature under high vacuum to yield 280 mg of a yellow oil conatining 135. This oil was partitioned between CH$_2$Cl$_2$ (10 mL) and 1 mL of saturated KOTfl. The aqueous layer was washed with CH$_2$Cl$_2$ (1×3 mL) and then the combined CH$_2$Cl$_2$ extract and washings were washed with water (1×2 mL), dried (4A molecular sieves, overnight, in refrigerator) filtered, and stripped to afford 135 as yellow semi solid, (65 mg) homogeneous by HPLC, and characterized to identity by nmr.

To an 80° C. solution of azetropically dried, solublized "no-carrier-added" [$^{18}$F]fluoride ion solution (38 mCi), composed of K$_2$CO$_3$ (0.3 mg) Kryptofix K222 aminopolyether cryptand (8 mg), and acetonitrile (1 mL), was added a solution of 135 (4 mg) in acetonitrile (400 uL). The aforementioned solution containing 135 was added to the [$^{18}$F] fluoride ion solution in a septum sealed, magnetically stirred reaction vessel, in 100 uL (~1 mg of 135 each portion) portions over a ~5 min period, during which time the temperature of the reaction vessel was being raised to 120° C. Following completion of 135 addition, the sealed reaction vessel was heated at 120° C. for a further 15 minutes, and then the reaction solvent was quickly blown off under a stream of inert gas (such as nitrogen) through the reaction vial until a gummy residue remained. The vial was then cooled to ~–10° C. (ice/salt bath), and a freshly prepared cooled (e.g. 4° C.) mixture of Oxone (10–15 mg) and H$_2$SO$_4$ (100–150 uL) was added to the vial through a teflon tube while the cooled vial contents were agitated with a stream of inert gas. Cooling was removed 2 min after addition of the Oxone/H$_2$SO$_4$ mixture was complete, and the reaction mixture was agitated with inert gas bubbling which was continued for 10–15 min at room temperature. The vial was reccooled to –10° C. and 3 mL of a 4:1 v:v alcohol (such as methanol or ethanol): water solution was added carefully to the vial to quench the Baeyer-Villiger (BV) reaction. Diluted BV reaction mixture was bubbled with SO$_2$ gas for 30 seconds and then the mixture was passed onto a 1×7 cm column of PVP resin wetted with an aqueous alcohol (such as methanol or ethanol). The mixture stood on the PVP column for 2–4 min and then was eluted therefrom (e.g. with suction or pressure) as a neutral solution. The column was then rinsed with more aqueous alcohol (3×5 mL) and the combined elutate and rinses were quickly concentrated to a volume of ~2–3 mL, and treated with 1 mL of 3 M NaOH in MeOH. The combined basic mixture reacted for 1–3 min at room temperature, and then was neutralized with addition of a slight excess of acid (e.g. HCL). Analysis of this solution by Radio-HPLC (Phenomenex Prodigy 3 C-18, 1:1:2 acetonitrile:methanol:20 mM NaH2PO4, pH 5.0) showed a single major radioactive peak chromatographically identical to authentic 6-fluoro-metatyrosine (6-FMT). The non-decay corrected radiochemical yield at this point was 14 mCi.

Thus it should be understood that compounds of the present invention, for example the above discussed compound 135, can be supplied in a kit for radiofluorination and the subsequent production of 6-[$^{18}$F]-FMT. For example, a kit of the present invention can include (i) a first container for containing one or more of the compounds of the present invention (e.g. compound 135) and (ii) a second container which containes a solvent (e.g. acetonitrile) for dissolving compounds of the present invention (e.g. compound 135) so that solutions of the present invention can be combined and made to react with nucleophilic [$^{18}$F] fluoride ion to form a radiofluorinated intermediate as described above. The aforementioned kit can also include a third container having disposed therein a peroxy acid derivative or peroxy acid precursor (such as Oxone, or H$_2$O$_2$,). In addition, the kit also includes a fourth container having disposed therein strong liquid or solid acid, or anhydride of a strong acid e.g., CF$_3$CO$_2$H, H$_2$SO$_4$, Triflic acid, and Nafion, or trifluroacetic for combining with the peroxy acid or peroxy acid precursor in the third container to form the Baeyer-Villiger (BV) reagent. The BV reagent is susequently combined with the aforementioned radiofluorinated intermediate of the present invention thereby by producing [$^{18}$F]FMT following an alkaline work up as described above.

Thus it should be appreciated that the present invention provides a quick and efficient route to give a family of imaging tracers including 6-[$^{18}$F]FMT. It should also be appreciated that, a multi-step synthesis is disclosed which provides a stable precursor for the purpose of radiofluorination. For example, preferably, one stable precursor for the purpose of radiofluorination is compound 135 as descrobed above. It was also demonstrated that $^{19}$F-amino acid 79 could be transformed to the desired 6-[$^{19}$F]FMT by a Baeyer-Villiger oxidation and subsequent deprotection steps.

General Procedures

All reactions were conducted under dry argon and stirred magnetically except when otherwise noted. Analytical TLC was performed on precoated (0.25 mm) silica gel GF Uniplate™ purchased from Analtech and developed with UV irradiation or ninhydrin treatment. Melting points were recorded using a Mel-Temp II capillary melting point apparatus and are uncorrected. Proton and carbon NMR spectra were obtained using a General Electric (Bruker) QE300 MHz Broadband NMR System and Techmag Interface Update running MacNMR 5.6 software in CDCl$_3$ and internal Me$_4$Si (TMS) reference unless otherwise indicated. Fluorine NMR spectra were obtained using a Varian Instruments 200 MHz Broadband Gemini 2000 NMR System running Solaris 2.6 and VNMR 6.1B using an external TFA reference and corrected with respect CFCl$_3$. Chiral HPLC was performed with a Varian 2010 Pump/2210 System, 2050 UV Variable Wavelength Detector, and Hewlett Packard 3390A Integrator using a Regis Pirkle-Concept Chiral (S, S)-Whelk-O-1 column (250×4.6 mm, 5 micron, 100 Å) with hexane/isopropanol (100/2 or 100/5, v/v). A Varian Star 9010/9001 Solvent Delivery System, 9050 Variable Wavelength UV-Vis Detector, Hewlett-Packard 3396 Series II Integrator and Waters Nova-Pak® C-18 column (150×3.9 mm, 4 micron, 60 Å) with 0.1% TFA+99.9& H$_2$O/0.08%

TFA+99.92% CH$_3$CN (100/0 to 20/80) were used to analyze the free amino acid derivatives. Final HPLC analyses during radiofluorination and deprotection steps were carried out on Hitachi L-6000 Pump, L-4000H UV Detector, and D-2500 Chromato-Integrator using a Phenomenex Prodigy 5 ODS-2 column (5 micron, 250×4.6 mm) with a Prodigy 5μ ODS-2 guard column (5 micron, 30×4.6 mm). This system was also equipped with a Bicron Frisk-Tech™ Radiodetector and used acetonitrile/methanol/20 mM NaH$_2$PO$_4$ (1:1:2, v/v), pH 5.0, as the mobile phase. [$^{18}$F]-Fluoride was produced using a RDS/112 Radioisotope Delivery System (11 MeV Proton Cyclotron) from Siemens Medical Systems, Inc. The radioactivity was measured using a Biodex Medical Systems PET Dose Calibrator Atomiab™ 100 or Atomiab™ 300. Radio-TLC analyses were done using a Bioscan Auto Changer 1000 and System 200 Imaging Scanner equipped with Win-Scan Version 2.2(5) Imaging Scanner Software for Windows (from Bioscan, Inc. in Washington, D.C.).

High Resolution Mass Spectra were obtained on a Kratos MS80 high-resolution magnet sector mass spectrometer with electron impact (EI), chemical ionization (CI) and fast-atom bombardment (FAB) ionization techniques, at the Mass Spectrometry Laboratory of the Department of Chemistry at Indiana University, Bloomington. Elemental analyses were performed by Midwest Microlab in Indianapolis, Ind.

Molecular modeling was performed on a Silicon Graphics Workstation using Spartan® Software, Version 1.0 (from Wavefunction, Inc. in Irvine, Calif.) and Quanta® Software, Version 4.0 (from Molecular Simulations, Inc. in Burlington, Mass.). Spartan® software was used to construct and minimize the conformation of the desired compounds using the AM1 and 321-G geometry optimization methods. The minimized conformers were exported into Quanta® software to obtain computed molecular properties, specifically the surface area for the solvent-atom interaction.

General Procedure for Cleaning Reillex-425 PVP Resin

Reillex™ 425 PVP (Poly-4-Vinylpyridine Polymer) Resin was purchased from Reilly Industries, Inc. in Indianapolis, Ind. Approximately 150–200 g commercial-grade PVP resin was transferred into a large Buchner filter funnel attached to an Erlenmeyer vacuum flask. Water, stored with the resin, was removed by filtration and discarded. The following series of washings was applied to the PVP resin in the funnel: 1.0 M sodium hydroxide (3×200 mL), distilled water (2×200 mL), methanol (2×200 mL), 2-propanol (2×200 mL), and acetonitrile (2×200 mL). Each wash consisted of filling the funnel with the specific solvent, mixing the slurry, and then removing and discarding the solvent. Qualitative analysis (QA) was completed by taking an aliquot of the cleaned resin (0.5 g) and transferring it to a test tube containing 1.0 ml acetonitrile. Another aliquot of resin was taken and transferred to a tube containing 1.0 ml of distilled water. The PVP slurry of each mixture was filtered and the supernatant was collected. HPLC (1:1:2 acetonitrile/methanol/20 mM NaH$_2$PO$_4$, pH 5.0) was used to check for any remaining contaminants by UV detection. If the two QA samples were not clear, then the cleaning process was repeated again. If the samples checked clear, then a final distilled water wash of the resin was completed and the cleaned resin was subsequently stored for later use.

Experimental Section for Compounds Leading to Compound (39)

Synthesis of 3-Methyl-4-nitro-benzoyl chloride (14).

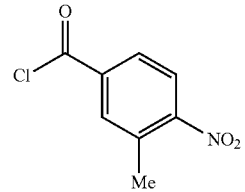

Thionyl chloride (79 mL, 128.2 g, 0.11 mol) and benzoic acid (10.0 g, 55.2 mmole) were added to a 250-mL single-necked round-bottom flask equipped with a magnetic stirring bar and a water-jacketed condenser. The mixture was refluxed for 3 hours (90° C.). Dry toluene (100 mL) was added and the solvent was evaporated to give a crude yellow solid (11.06 g, 100%), which was used directly for the subsequent Grignard reaction: m.p. 29–30° C. (Lit. m.p. 28° C.).

$^1$H-NMR (CDCl$_3$) δ 2.66 (s, 3H), 8.02 (app. d, J=8.00 Hz, 1H), 8.10 (app. d, J=8.00 Hz, 2H). $^{13}$C-NMR (CDCl$_3$) δ 19.91, 124.93, 129.65, 134.01, 135.36, 136.33, 153.15, 167.06.

Synthesis of Grignard Reagents.

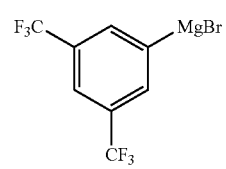

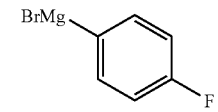

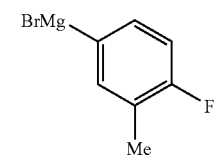

Polished magnesium chips (1.00 g, 41.1 mmol), iodine crystals (2–3), and dry THF (3 mL) were mixed in a 50-mL single-necked round-bottom flask equipped with a magnetic stirring bar and a Claisen head fitted with a calcium chloride drying tube. A solution of bromobenzene (6.35 mL, 10.8 g, 36.8 mmol) in dry THF (10 mL) was prepared. With slow stirring, 8–10 drops of the bromobenzene solution was added to the magnesium in THF. Sonication (Fisher Scientific Solid State Ultrasonic FS-9) was applied to the reaction to induce the initial formation of the Grignard reagent. Once the reaction had been initiated, the remainder of the bromobenzene solution was added dropwise over a 5 min. period. After addition was complete, the reaction mixture was warmed gently to maintain a gentle reflux for 15–30 min. The mixture was then filtered and used directly for the subsequent reaction.

General Procedure for the Preparation of Benzophenones.

A. Synthesis of (3,5-bis-Trifluoromethyl-phenyl)-(3-methyl-4-nitro-phenyl)-methanone (17).

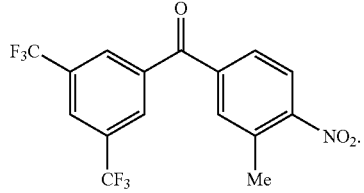

A solution of the benzoyl chloride (10 g, 55.2 mmole) in dry THF (20 mL) was stirred magnetically in an argon-purged 100-mL single-necked round-bottom flask equipped with an addition funnel. The Grignard reagent (11.7 g, 36.8 mmole) prepared previously was added dropwise over fifteen minutes to the above solution. The reaction mixture was stirred for an additional four hours at room temperature, then quenched with water (25 mL) and extracted with diethyl ether (3×25 mL). The combined organic layers were washed with water to remove any residual salts. The organic layer was dried ($Na_2SO_4$), filtered and the solvent was evaporated to give a crude yellow solid (12.8 g, 92%), which was purified by flash chromatography (hexane/EtOAc=9:1) to afford yellow crystals (6.6 g, 52%): m.p. 66–68° C.

$^1$H-NMR (CDCl$_3$) δ 2.68 (s, 3H), 7.70 (dd, J=1.48, 8.83, 1H), 7.79 (d, J=1.48, 1H), 8.08 (d, J=8.83, 1H), 8.16 (s, 1H), 8.24 (s, 2H). $^{13}$C-NMR (CDCl$_3$) δ 20.07, 122.81 ($J_{C-F}$=273.03), 124.96, 126.48 ($J_{C-F}$=3.66 Hz), 128.13, 129.82 ($J_{C-F}$=3.66 Hz), 132.65 ($J_{C-F}$=34.18 Hz), 134.04, 134.31, 138.41, 139.37, 152.11, 191.97. $^{19}$F-NMR (CDCl$_3$) δ–65.75. Anal. Calcd. for $C_{16}H_9F_6NO_3$: C, 50.94; H, 2.40; N, 3.71. Found: C, 50.77; H, 2.42; N, 3.72.

B. Synthesis of 4-Fluoro-3-methyl-benzoic acid (20).

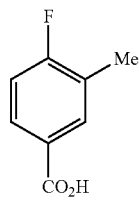

Carbon dioxide (dry ice, several grams) was bubbled into a Grignard solution of 4-fluoro-3-methylphenylmagnesium bromide with magnetic stirring until all the dry ice had evaporated. The reaction was quenched with deionized water (15 mL) and extracted with 2:1 Et$_2$O/EtOAc (2×15 mL). The aqueous layer was reacidified with concentrated HCl and the white precipitate was isolated (4.08 g, 50%): m.p. 168–169° C. (Lit. m.p. 168–169° C.).

$^1$H-NMR (CDCl$_3$) δ 2.30 (d, 3H, $J_{C-F}$=1.47 Hz), 7.04 (t, 1H, $J_{C-F}$=8.83 Hz), 7.84–7.92 (m, 2H). $^{13}$C-NMR (CDCl$_3$) δ 14.4 ($J_{C-F}$=3.7 Hz), 114.9 ($J_{C-F}$=23.2 Hz), 124.8 ($J_{C-F}$=18.3 Hz), 126.8 ($J_{C-F}$=3.7 Hz), 129.50 ($J_{C-F}$=8.5 Hz), 133.50 ($J_{C-F}$=7.32 Hz), 164.10 ($J_{C-F}$=251.5 Hz), 167.70.

C. Synthesis of (3,5-bis-Trifluoromethyl-phenyl)-(4-fluoro-phenyl)-methanone (25).

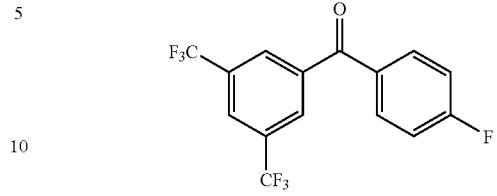

The reaction procedure was the same as that used to make 25 above to give a yellow oil (0.549 g, 82%).

$^1$H-NMR (CDCl$_3$) δ 7.241 (m, 2H), 7.845 (m, 2H), 8.108 (s, 1H), 8.208 (s, 2H). $^{13}$C-NMR (CDCl$_3$) δ 116.1245 ($J_{C-F}$=21.98 Hz), 122.9225 ($J_{C-F}$=273.44 Hz), 125.627 ($J_{C-F}$=3.66 Hz), 129.624, 132.191 ($J_{C-F}$=34.18 Hz), 132.288 ($J_{C-F}$=2.44 Hz), 132.6915 ($J_{C-F}$=9.76 Hz), 139.409, 166.0675 ($J_{C-F}$=256.35 Hz), 191.976 ($J_{C-F}$=3.66 Hz). $^{19}$F-NMR (CDCl$_3$) δ–106.52, –66.11 HRMS: Calcd. for $C_{15}H_7F_7O$: 336.0385. Found: 336.0371.

D. Synthesis of (3,5-bis-Trifluoromethyl-phenyl)-(4-fluoro-3-methyl-phenyl)-methanone (22).

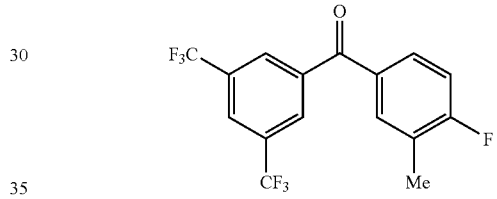

The reaction procedure was the same as that used to make 22 above to give product (3.41 g, 92%): m.p. 37–38° C.

$^1$H-NMR (CDCl$_3$) δ 2.37 (d, 3H, $J_{C-F}$=2.21 Hz), 7.16 (app. t, 1H, $J_{C-F}$=8.83 Hz), 7.60 (m, 1H), 7.72 (dd, 1H, $J_{C-F}$=1.47 Hz, 7.35 Hz), 8.10 (s, 1H), 8.20 (s, 2H). $^{13}$C-NMR (CDCl$_3$) δ 14.60 ($J_{C-F}$=2.45 Hz), 115.65 ($J_{C-F}$=23.19 Hz), 122.98 ($J_{C-F}$=273.03 Hz), 125.64 ($J_{C-F}$=3.66 Hz), 126.32 ($J_{C-F}$=17.09 Hz), 129.70 ($J_{C-F}$=3.66 Hz), 130.15 ($J_{C-F}$=9.77 Hz), 132.05 ($J_{C-F}$=7.32 Hz), 132.25 ($J_{C-F}$=33.77 Hz), 133.86 ($J_{C-F}$=7.32 Hz), 139.64, 164.79 ($J_{C-F}$=255.13 Hz), 192.41. $^{19}$F-NMR (CDCl$_3$) δ–109.98, –65.18. Anal. Calcd. for $C_{16}H_9F_7O$: C, 54.84;p H, 2.59 Found: C, 54.51; H, 2.58.

E. Synthesis of (3,5-bis-Trifluoromethyl-phenyl)-bis-(4-fluoro-3-methyl-phenyl)-methanol (135).

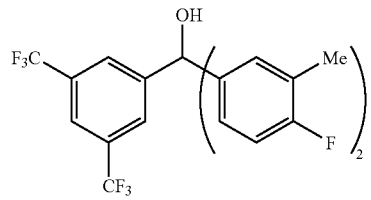

The side product was isolated from the previous reaction to give 135 in 4% yield (38.5 mg).

$^1$H-NMR (CDCl$_3$) δ 2.17 (s, 6H), 6.84 (app. d, 4H, J=6.62 Hz), 6.92 (app. t, 2H, J=9.19 Hz), 7.58 (s, 1H), 7.78 (s, 1H). $^{13}$C-NMR (CDCl$_3$) δ 14.69 ($J_{C-F}$=3.66 Hz), 91.38, 114.73

($J_{C-F}$=21.97 Hz), 121.69, 124.69 ($J_{C-F}$=255.12 Hz), 124.80 ($J_{C-F}$=17.09 Hz), 127.94 ($J_{C-F}$=8.54 Hz), 129.00, 131.11 ($J_{C-F}$=33.77 Hz), 131.87 ($J_{C-F}$=39.06 Hz), 136.19 ($J_{C-F}$=4.88 Hz), 145.05, 322.01 ($J_{C-F}$=249.02 Hz).

Procedure for the Preparation of Phenyl Benzoates.

A. Synthesis of 3,5-bis-Trifluoromethyl-benzoic acid 4-fluoro-phenyl ester (104).

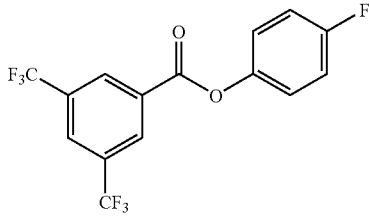

3',5'-Bis(trifluoromethyl)benzoyl chloride (1.6 mL, 8.7 mmol), 4-fluoro-phenol (0.22 g, 2.0 mmol), dichloromethane (3 mL), and diisopropylethylamine (3.0 mL, 17.4 mmol) were sequentially added to an argon-purged 25-mL round bottom flask equipped with a magnetic stir bar and argon-filled balloon. The reaction was stirred overnight and was then concentrated in vacuo. The crude mixture was purified by flash chromatography (9:1 hexanes/EtOAc) to afford a yellow solid (0.65 g, 100%): m.p. 60–61° C.

$^1$H-NMR (CDCl$_3$) δ 7.18 (m, 4H), 8.15 (s, 1H), 8.64 (s, 2H). $^{13}$C-NMR (CDCl$_3$) δ 116.65, 122.88 ($J_{C-F}$=273.44 Hz), 122.98, 127.09, 130.32, 131.73, 132.67 ($J_{C-F}$=34.18 Hz), 146.29, 160.74 ($J_{C-F}$=245.36 Hz), 162.65. $^{19}$F-NMR (CDCl$_3$) δ−118.25, −65.73. HRMS: Calcd. for C$_{15}$H$_7$F$_7$O$_2$: 352.0334. Found: 352.0345.

B. Synthesis of 3,5-bis-Trifluoromethyl-benzoic acid 4-fluoro-3-methyl-phenyl ester (37).

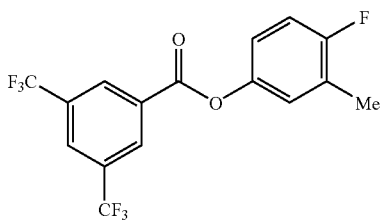

The preparation of the ester followed the same procedure as listed above. The crude mixture was purified by flash chromatography (9:1 hexanes/EtOAc) to afford a yellow oil (3.0 g, 100%).

$^1$H-NMR (CDCl$_3$) δ 2.31 (s, 3H), 7.06 (m, 3H), 8.15 (s, 1H), 8.63 (s, 2H). $^{13}$C-NMR (CDCl$_3$) δ 14.71 ($J_{C-F}$=2.44 Hz), 115.97 ($J_{C-F}$=24.42 Hz), 120.05 ($J_{C-F}$=8.55 Hz), 122.95 ($J_{C-F}$=273.44 Hz), 124.19 ($J_{C-F}$=4.88 Hz), 126.64 ($J_{C-F}$=19.53 Hz), 127.08 ($J_{C-F}$=3.67 Hz), 130.32 ($J_{C-F}$=2.45 Hz), 131.89, 132.68 ($J_{C-F}$=43.18 Hz), 145.95 ($J_{C-F}$=2.45 Hz), 159.34 ($J_{C-F}$=244.14 Hz), 162.80. $^{19}$F-NMR (CDCl$_3$) δ−122.47, −65.20. HRMS: Calcd. for C$_{16}$H$_9$F$_7$O$_2$: 366.0491. Found: 366.0488.

Procedure for the Preparation of Benzyl Bromides.

The following benzylic halides were used for PTC alkylation studies. Compound 137 was made from commercially available 4-chlorotoluene (Aldrich cat. No. 11, 192-9). Benzylic halides 29, 31, 32, 35, 36, 38, and 138 were prepared as outlined below.

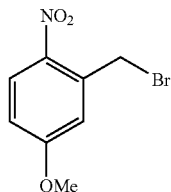

29

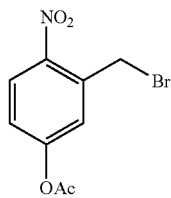

31

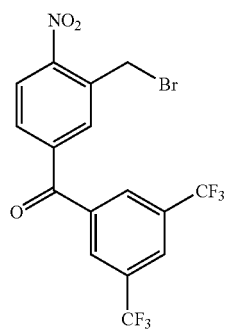

32

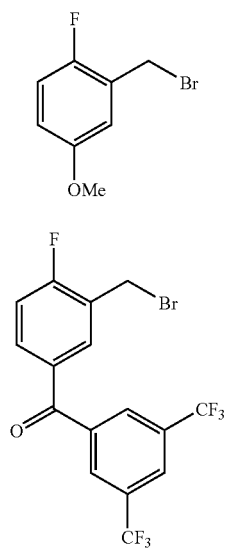

35

36

-continued

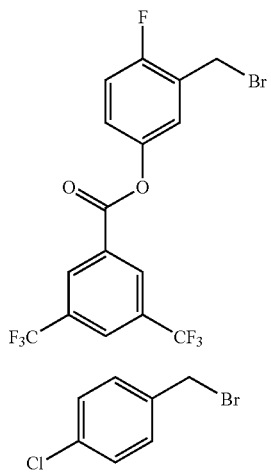

38

138

A. Synthesis of (3,5-bis-Trifluoromethyl-phenyl)-(3-bromomethyl-4-nitro-phenyl)-methanone (32).

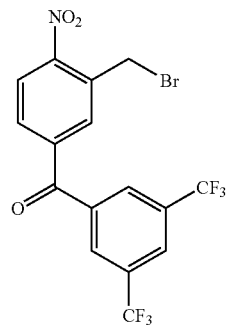

The reaction apparatus consisted of a 25-mL single-necked round-bottom flask equipped with a water-jacketed condenser, magnetic stirrer, and an argon-filled balloon. A solution of the nitrotoluene (1.00 g, 2.65 mmol), carbon tetrachloride (10 mL), a catalytic amount of benzoyl peroxide (0.01 g, 0.04 mmol), and N-bromosuccinimide (0.57 g, 3.18 mmol) were added to the reaction flask. The mixture was refluxed and irradiated under a 90-watt lamp (GE watt-miser light bulb, 130 V, 1000 hrs) for 6 h and then cooled to room temperature. The precipitated succinimide was removed by gravity filtration and the filtrate was diluted with $CCl_4$ (40 mL), extracted with sodium metabisulfite (28 M, 1×50 mL) and water (1×50 mL). The organic layer was separated and dried over magnesium sulfate, filtered and evaporated to afford a crude oil (1.264 g, 106%). A proton NMR of the crude product indicated a 59% yield of the desired product. The crude oil was chromatographed on silica gel (hexane:EtOAc=20:1) to give the product as yellow crystals (0.480 g, 40%): m.p. 78–79° C. Starting material (0.640 g, 28%) and dibrominated side-product (0.199 g, 14%) were also isolated from the chromatography.

$^1$H-NMR (CDCl$_3$) δ 4.86 (s, 2H), 7.85 (dd, 1H, J=1.84 Hz, 8.46 Hz), 8.02 (d, 1H, J=1.47 Hz), 8.18 (d, 1H, J=8.82 Hz), 8.18 (s, 1H), 8.25 (s, 2H). $^{13}$C-NMR (CDCl$_3$) δ 27.50, 122.70 ($J_{C-F}$=273.44 Hz), 125.92, 126.72 ($J_{C-F}$=3.66 Hz), 129.83 ($J_{C-F}$=3.66 Hz), 130.42, 132.73 ($J_{C-F}$=34.18 Hz), 133.81, 133.89, 137.83, 139.88, 150.52, 191.13. $^{19}$F-NMR (CDCl$_3$) 67 –65.75. Anal. Calcd. for $C_{16}H_8BrF_6NO_3$: C, 42.13; H, 1.77; N, 3.07. Found: C, 42.24; H, 1.77; N, 2.95.

B. Synthesis of (3,5-bis-Trifluoromethyl-phenyl)-(3-dibromomethyl-4-nitro-phenyl)-methanone (137).

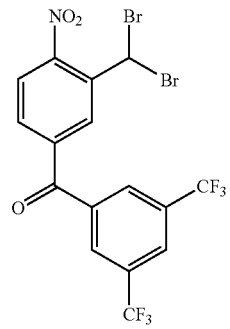

The isolated dibromide was isolated from a similar bromination reaction as listed above but 3.0 eq NBS was used to give 139 in 14% yield (0.2 g): m.p. 62–63° C.

$^1$H-NMR (CDCl$_3$) δ 7.43 (s, 1H), 7.94 (dd, 1H, $J_{C-F}$=1.47 Hz, 8.09 Hz), 8.09 (d, 1H, $J_{C-F}$=8.82 Hz), 8.20 (s, 1H), 8.30 (s, 2H), 8.56 (d, 1H, $J_{C-F}$=1.47 Hz). $^{13}$C-NMR (CDCl$_3$) δ 32.69, 122.76 ($J_{C-F}$=273.43 Hz), 125.20, 126.94 ($J_{C-F}$=3.66 Hz), 130.08 ($J_{C-F}$=3.66 Hz), 131.37, 132.84 ($J_{C-F}$=34.18 Hz), 134.26, 137.02, 137.57, 140.38, 146.38, 190.69. HRMS: Calcd. for $C_{16}H_7{}^{79}Br^{81}BrF_6NO_3$: 534.8678. Found: 534.8664.

C. Synthesis of 2-Bromomethyl-4-methoxy-1-nitro-benzene (29).

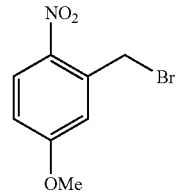

The reaction apparatus consisted of a 50-mL single-necked round-bottom flask equipped with a water-jacketed condenser, magnetic stirrer, and an argon-filled balloon. A solution of 5-methoxy-2-nitrotoluene (0.25 g, 1.50 mmol), carbon tetrachloride (25 mL), a catalytic amount of benzoyl peroxide (25 mg, 0.83 mmol), and N-bromosuccinimide (0.32 g, 1.8 mmol) were added to the reaction flask. The mixture was refluxed and irradiated under a 90-watt lamp (GE watt-miser light bulb, 130 V, 1000 hrs) for 5 h and then cooled to room temperature. The precipitated succinimide was removed by gravity filtration and the filtrate was extracted with sodium metabisulfite (28 M, 1×50 mL) and water (1×50 mL). The organic layer was separated, dried over sodium sulfate, filtered and then evaporated to afford a crude oil (382 mg, 105%). The crude product was chromatographed on silica gel (hexane/EtOAc=9:1) to give the product as yellow crystals (172 mg, 47%): m.p. 64–65° C.

$^1$H-NMR (CDCl$_3$) δ 3.92 (s, 3H), 4.87 (s, 2H), 6.92 (dd, 1H, $J_{C-F}$=2.94 Hz, 8.82 Hz), 7.03 (d, 1H, $J_{C-F}$=2.94 Hz), 8.16 (d, 1H, $J_{C-F}$=9.56 Hz). $^{13}$C-NMR (CDCl$_3$) δ 29.77, 56.01, 113.99, 117.58, 128.32, 135.63, 140.70, 163.40. HRMS: Calcd. for $C_8H_8{}^{81}BrNO_3$: 246.9668. Found: 246.9663.

D. Synthesis of 2-Dibromomethyl-4-methoxy-1-nitro-benzene (138).

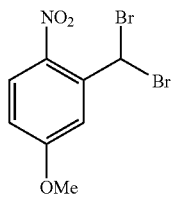

This dibromide was isolated from the previous reaction as a yellow oil (97.4 mg, 20%).

$^1$H-NMR (CDCl$_3$) δ 3.97 (s, 3H), 6.94 (dd, J=2.21, 8.82 Hz, 1H), 7.68 (m, 2H), 8.02 (d, J=8.83 Hz, 1H). $^{13}$C-NMR (CDCl$_3$) δ 34.95, 56.17, 111.83, 115.59, 117.29, 127.36, 138.99, 163.89. HRMS: Calcd. for C$_8$H$_7$$^{79}$Br$_2$NO$_3$: 322.8793. Found: 322.8798.

E. Synthesis of Acetic acid 3-bromomethyl-4-nitro-phenyl ester (31).

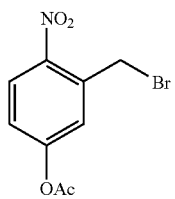

This reaction followed the same procedure as indicated above. A yellow solid wsa obtained (126 mg, 36%): m.p. 56–57° C.

$^1$H-NMR (CDCl$_3$) δ 2.35 (s, 3H, CH$_3$), 4.82 (s, 2H, CH$_3$), 7.25 (dd, 1H, J$_{C-F}$=2.20 Hz, 8.80 Hz), 7.36 (d, 1H, J$_{C-F}$=2.90 Hz), 8.12 (d, 1H, J$_{C-F}$=8.80 Hz). $^{13}$C-NMR (CDCl$_3$) δ 21.10, 28.50, 122.60, 125.40, 127.30, 134.90, 144.90, 154.10, 168.20. HRMS: Calcd. for C$_9$H$_8$$^{79}$BrNO$_4$: 272.9637. Found: 272.9646.

F. Synthesis of Acetic acid 3-dibromomethyl-4-nitro-phenyl ester (139).

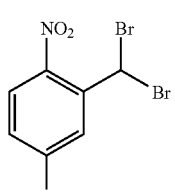

This material was isolated from the previous reaction as yellow crystals (222 mg, 49%): m.p. 77–78° C.

$^1$H-NMR (CDCl$_3$) δ 2.38 (s, 3H), 7.29 (dd, J=2.21, 8.83 Hz, 1H), 7.51 (s, 1H), 7.97 (d, J=2.21 Hz, 1H), 8.00 (d, J=8.83 Hz, 1H). $^{13}$C-NMR (CDCl$_3$) δ 21.00, 33.48, 123.70, 125.39, 126.22, 138.13, 141.09, 154.57, 167.93. HRMS: Calcd. for C$_9$H$_7$$^{79}$Br$_2$NO$_4$: 350.8742. Found: 350.8740.

G. Synthesis of 2-Bromomethyl-1-fluoro-4-methoxy-benzene (35).

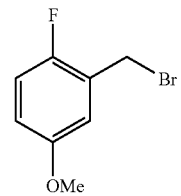

The product was prepared with the same procedure as indicated above to give a yellow oil (2.05 g, 66%). Interestingly, the yield improved to 90% (2.80 g) when dibromohydantoin (0.55 eq) was used as the brominating agent instead of NBS.

$^1$H-NMR (CDCl$_3$) δ 3.77 (s, 3H), 4.47 (s, 2H), 6.77–7.00 (m, 3H). $^{13}$C-NMR (CDCl$_3$) δ 27.47 (J$_{C-F}$=3.67 Hz), 57.44 (J$_{C-F}$=8.54 Hz), 117.27 (J$_{C-F}$=3.67 Hz), 117.34 (J$_{C-F}$=2.44 Hz), 117.95 (J$_{C-F}$=23.19 Hz), 127.21 (J$_{C-F}$=17.09 Hz), 156.57 (J$_{C-F}$=242.92 Hz), 157.37 (J$_{C-F}$=2.44 Hz). $^{19}$F-NMR (CDCl$_3$) δ–130.48.

H. Synthesis of 2-Dibromomethyl-1-fluoro-4-methoxy-benzene (140).

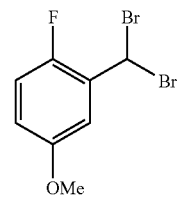

The dibromide was isolated from the previous NBS reaction as white crystals (43 mg, 1%): m.p. 57–58° C.

$^1$H-NMR (CDCl$_3$) δ 3.84 (s, 3H), 6.91 (s, 1H), 6.94 (app. t, 1H, J$_{C-F}$=8.09 Hz), 7.30 (dd, 1H, J$_{C-F}$=3.68 Hz, 5.93 Hz). $^{13}$C-NMR (CDCl$_3$) δ 32.08 (J$_{C-F}$=4.88 Hz), 55.90, 114.29, 116.24 (J$_{C-F}$=23.20 Hz), 117.49 (J$_{C-F}$=8.55 Hz), 129.52 (J$_{C-F}$=13.42 Hz), 150.91 (J$_{C-F}$=244.14 Hz), 156.11. HRMS: Calcd. for C$_8$H$_7$$^{81}$Br$_2$FO: 299.8809. Found: 299.8815.

I. Synthesis of (3,5-bis-Trifluoromethyl-phenyl)-(3-bromomethyl-4-fluoro-phenyl)-methanone (36).

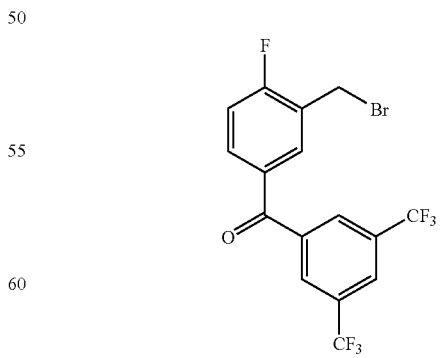

The benzyl bromide was prepared in the same manner as indicated above to give white crystals (0.826 g, 68%): m.p. 90–92° C.

¹H-NMR (CDCl₃) δ 4.55 (s, 2H), 7.52 (app. t, 1H, $J_{C-F}$=7.72 Hz), 7.76 (m, 1H), 7.92 (dd, 1H, $J_{C-F}$=2.21 Hz, 7.36 Hz), 8.12 (s, 1H), 8.21 (s, 2H). ¹³C-NMR (CDCl₃) δ 24.22 ($J_{C-F}$=4.89 Hz), 116.63 ($J_{C-F}$=21.97 Hz), 124.66 ($J_{C-F}$=272.22 Hz). 125.87 ($J_{C-F}$=3.66 Hz), 126.59 ($J_{C-F}$=14.65 Hz), 129.35 ($J_{C-F}$=67.14 Hz), 129.68 ($J_{C-F}$=2.44 Hz), 132.36 ($J_{C-F}$=34.18 Hz), 132.54, 133.68 ($J_{C-F}$=4.88 Hz), 139.04, 163.70 ($J_{C-F}$=258.79 Hz), 191.59. ¹⁹F-NMR (CDCl₃) d–121.90, –65.78. HRMS: Calcd for $C_{16}H_8BrF_7O$: 427.9646. Found: 427.9639.

J. Synthesis of 3,5-bis-Trifluoromethyl-benzoic acid 3-bromomethyl-4-fluoro-phenyl ester (38).

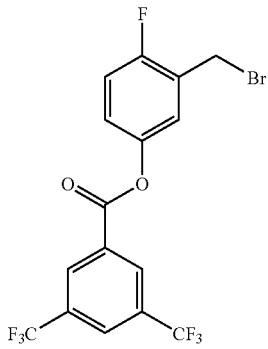

The benzyl bromide was prepared in the same manner as indicated above to give white crystals (0.708 g, 58%): m.p. 66–68° C.

¹H-NMR (CDCl₃) δ 4.52 (s, 2H), 7.19 (m, 2H), 7.32 (dd, 1H, $J_{C-F}$=2.21 Hz, 5.88 Hz), 8.16 (s, 1H), 8.63 (s, 2H). ¹³C-NMR (CDCl₃) δ 24.63 ($J_{C-F}$=3.66 Hz), 116.93 ($J_{C-F}$=23.20 Hz), 122.82 ($J_{C-F}$=273.44 Hz), 123.32 ($J_{C-F}$=8.54 Hz), 124.03 ($J_{C-F}$=3.66 Hz), 127.21 ($J_{C-F}$=3.66 Hz), 130.30 ($J_{C-F}$=3.66 Hz), 131.49, 132.70 ($J_{C-F}$=34.18 Hz), 146.16 ($J_{C-F}$=3.67 Hz), 156.76, 158.40 ($J_{C-F}$=249.02 Hz), 162.47. ¹⁹F-NMR (CDCl₃) δ–121.78, –65.71. Anal. Calcd for $C_{16}H_8BrF_7O_2$: C, 43.17; H; 1.81, N, 0.0. Found: C, 43.32; H, 1.87, N; 0.0.

Synthesis of (Benzhydrylidene-amino)-acetic acid tert-butyl ester (3).

In a 50-mL round-bottom flask equipped with a water-jacketed condenser and magnetic stirring bar, a mixture of t-butyl chloroacetate (10 g, 66.4 mmole), benzophenone imine (8.02 g, 44.3 mmole), and anhydrous potassium carbonate (9.18 g, 66.4 mmole) was stirred overnight at 110° C. Using a course Buchner funnel, the solid inorganic salts were removed from the solution by filtration and the solids were washed with ethyl acetate (2×25 mL). The combined filtrates were diluted with ethyl acetate to a total volume of 100 mL. The organic mixture was washed with water (3×100 mL), dried ($Na_2SO_4$), filtered, and the solvent was removed in vacuo. The crude residue was recrystallized with hexanes to afford white crystals (5.24 g, 40%): m.p. 114–115° C. (Lit. m.p. 111–112° C.).³ ¹H-NMR (CDCl₃) δ 1.46 (s, 9H), 4.12 (s, 2H), 7.18 (m, 2H), 7.34 (m, 3H), 7.45 (m, 3H), 7.66 (m, 2H). ¹³C-NMR (CDCl₃) δ 28.13, 56.37, 80.99, 127.74, 128.01, 128.27, 128.61, 128.73, 128.76, 130.05, 130.34, 132.39, 136.25, 139.45, 169.82, 171.48

Alkylation Reactions.

A. 2-(Benzhydrylidene-amino)-3-[5-(3,5-bis-trifluoromethyl-benzoyl)-2-nitro-phenyl]-propionic acid tert-butyl ester (49).

Method A.

The benzyl bromide derivative 32 (1.8 g, 3.95 mmol) was dissolved in distilled dichloromethane (25 mL) in a 50-mL round-bottom flask containing a magnetic stirrer under an argon atmosphere at –78° C. Schiff base 3 (1.1 g, 3.59 mmol), cinconindinum catalyst 43 (0.225 g, 0.359 mmol), and BTPP 42 (1.37 mL, 4.47 mmol) were sequentially added and the mixture was stirred overnight at –78° C. The reaction was stopped by rapid removal of the solvent by vacuum. A subsequent flash chromatographic step (5–10% EtOAc:hexanes) was carried out to remove the excess base and to purify the desired product. The pure pale yellow solid was obtained in 57% (1.25 g). (Note: since the flash chromatography was carried out quickly, other fractions were obtained containing a mixture of product and other impurities. After characterizing the product, the precautions used to isolate the pure product were not necessary for future alkylation reactions, flash chromatography was used only to remove the base. The subsequent imine deprotection sufficed for isolation of the deprotected amino ester salt in 45% yield.) Chiral HPLC was performed on compound 49 using a Varian 2010 Pump/2210 System, 2050 UV Variable Wavelength Detector, and Hewlett Packard 3390A Integrator using a Regis Pirkle-Concept Chiral (S, S)-Whelk-O-1 column (250×4.6 mm, 5 micron, 100 Å) with hexane/isopropanol (95:5 v/v). A wavelength of 254 nm and flow rate of 1.0 ml/min afforded good separation analysis of the enantiomeric mixture, 90% S:10% R (80% ee).

¹H-NMR (CDCl₃) δ 1.42 (s, 9H), 3.53 (dd, J=8.82, 13.24 Hz, 1H), 3.66 (dd, J=4.41, 13.24 Hz, 1H), 4.31 (dd, J=4.41, 8.82 Hz, 1H), 6.72 (m, 2H), 7.34 (m, 8H), 7.72 (dd, J=1.47, 8.46, 1H), 7.88 (d, J=1.47, 1H), 7.95 (d, J=8.46 Hz, 1H), 8.12 (s, 2H). ¹³C-NMR (CDCl₃) δ 28.00, 35.95, 65.72, 81.88, 122.81 ($J_{C-F}$=272.83), 124.80, 126.37 ($J_{C-F}$=3.66 Hz), 127.47, 128.00, 128.39, 128.74, 129.63 ($J_{C-F}$=2.45 Hz), 130.53, 132.52 ($J_{C-F}$=34.18), 134.41, 135.60, 135.93, 138.38, 138.67, 138.88, 152.54, 169.77, 171.48, 191.76 ¹⁹F-NMR (CDCl₃) δ–65.695. HRMS: Calcd for $C_{35}H_{28}F_6N_2O_5$: 670.1902. Found: 670.1922.

B. 2-(Benzhydrylidene-amino)-3-[5-(3,5-bis-trifluoromethyl-benzoyl)-2-fluoro-phenyl]-propionic acid tert-butyl ester (50).

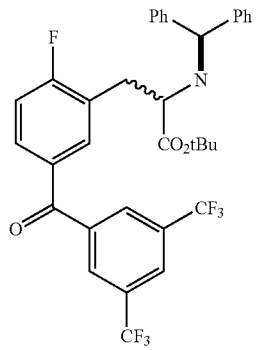

Method A.

The benzyl bromide derivative CC (0.5 g, 1.17 mmol) was dissolved in distilled dichloromethane (12.5 mL) in a 50-mL round-bottom flask containing a magnetic stirrer under an argon atmosphere at −78° C. Schiff base 3 (0.313 g, 1.06 mmol), cinconindinum catalyst 43 (0.064 g, 0.106 mmol), and BTPP 42 (0.40 mL, 1.27 mmol) were sequentially added and the mixture was stirred overnight at −78° C. The reaction was stopped by quick removal of the solvent by vacuum. A subsequent flash chromatographic step (5–10% EtOAc/hexanes) was carried out to remove the excess base and to purify the desired product. The pure pale yellow residue was obtained in (0.614 g, 90%) (Note: since the flash chromatography was carried out quickly, other fractions were obtained containing a mixture of product and other impurities. After characterizing the product, the precautions used to isolate the pure product were necessary for future alkylation reactions; flash chromatography was used only to remove the base.

Method B.

The benzyl bromide derivative 36 (0.8 g, 2.24 mmol) was dissolved in distilled THF (10 mL) in a 25-mL pear-shaped round-bottom flask containing a magnetic stirrer under an argon atmosphere at −78° C. Schiff base 3 (0.55 g, 1.86 mmol), and 1 M LiHMDS (2.24 mL, 2.24 mmol) were sequentially added at −78° C. and the mixture was stirred overnight at the same temperature. The reaction was stopped by quick removal of the solvent by vacuum. A subsequent flash chromatographic step (5–10% EtOAc/hexanes) was carried out to remove the excess base and to purify the desired product. The pure yellow residue was obtained in 49% (0.323 g).

$^1$H-NMR (CDCl$_3$) δ 1.42 (s, 9H), 3.53 (dd, 1H, J=8.83 Hz, 13.24 Hz), 3.66 (dd, 1H, J=4.41 Hz, 13.97 Hz), 4.30 (dd, 1H, J=4.42 Hz, 8.83 Hz), 6.72 (d, 2H, J=5.89 Hz), 7.23 (dd, 2H, J=5.88 Hz, 13.24 Hz), 7.35 (m, 4H), 7.47 (d, 2H, J=7.36 Hz), 7.71 (dd, 1H, J=1.84 Hz, 8.46 Hz), 7.88 (d, 1H, J=1.47 Hz), 7.95 (d, 1H, J=8.09 Hz), 8.12 (s, 3H). $^{13}$C-NMR (CDCl$_3$) δ 27.95, 35.91, 65.65, 81.87, 122.75 (J$_{C-F}$=273.43 Hz), 124.80, 126.37 (J$_{C-F}$=3.66 Hz), 127.40, 127.97, 128.35, 128.42, 128.71, 129.61 (J$_{C-F}$=2.44 Hz), 130.53, 132.46 (J$_{C-F}$=34.18 Hz), 134.36, 135.62, 135.85, 138.28, 138.61, 138.79, 152.45, 169.76, 171.50, 191.78.

C. 3,5-bis-Trifluoromethyl-benzoic acid 3-[2-(benzhydrylidene-amino)-2-tert-butoxycarbonyl-ethyl]-4-fluoro-phenyl ester (51).

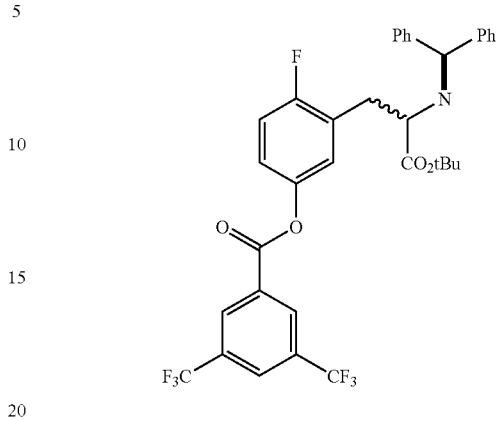

The product was prepared in the same manner as indicated above. A pure yellow oil (65.4 mg, 7%), was isolated from a silica column pretreated with 1% triethylamine in 99% 9:1 hexane/EtOAc. More product with a slight amount of Schiff base 3 was isolated as a semi-crude mixture (363 mg).

$^1$H-NMR (CDCl$_3$) 1.46 (s, 9H), 3.18 (dd, J=8.83, 13.24 Hz, 1H), 3.35 (dd, J=4.05, 13.24 Hz, 1H), 4.20 (dd, J=4.05, 8.83 Hz, 1H), 6.80 (m, 2H), 7.01 (m, 3H), 7.31 (m, 6H), 7.59 (m, 2H), 8.13 (s, 1H), 8.50 (s, 2H). $^{13}$C-NMR (CDCl$_3$) δ 27.99, 32.43, 65.89, 81.44, 115.84 (J$_{C-F}$=25.63 Hz), 120.82 (J$_{C-F}$=9.77 Hz), 122.79 (J$_{C-F}$=272.22 Hz), 125.20(J$_{C-F}$=4.89 Hz), 127.11 (J$_{C-F}$=18.31 Hz), 127.72, 127.83, 128.15, 128.40, 128.80, 130.16, 131.63, 132.43 (J$_{C-F}$=34.18 Hz), 136.16, 139.38, 145.59 (J$_{C-F}$=3.66 Hz), 159.13 (J$_{C-F}$=245.36 Hz), 162.37, 170.22, 170.99. $^{19}$F-NMR (CDCl$_3$) δ−122.51, −65.70. HRMS: Calcd for C$_{35}$H$_{29}$F$_7$NO$_4$ (Cation): 660.1984. Found: 660.1978.

Preparation of 1,1-Dimethylethyl N-(diphenylmethylene)-4-chloro-phenylalaninate (141).

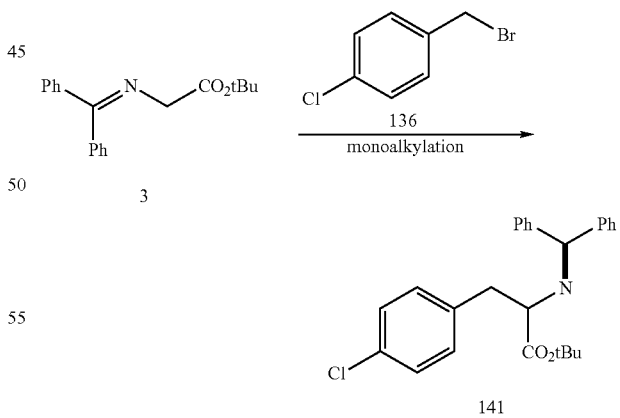

The benzophenone imine of glycine t-butyl ester 3 (1.8 mmol), tetra-n-butyl-ammonium bromide (0.2 mmol), dichloromethane (6 mL), and 4-chlorobenzyl bromide 136 (2 mmol) were added to a three-necked round-bottom flask equipped with a stirring bar. 50% aqueous NaOH (36.5 mmol) was added at once and the resulting mixture was stirred vigorously at room temperature until starting Schiff base had disappeared by TLC (4:1 hexane/EtOAc) (approximately 8 h). Water (3 mL) and dichloromethane (3 mL) were added and the mixture was transferred to a separatory funnel. The organic layer was separated and evaporated in vacuo. The residue was taken up in ether (10 mL) and water (6 mL), and the ether layer was separated and washed with water (3×3.0 mL). The organic layer was dried ($Na_2SO_4$), filtered, and evaporated in vacuo. The resulting crude product (95%) was purified by flash chromatography (dichloromethane) to afford white crystals 141 (90%): m.p. 102–103° C., which was analyzed by NMR.

$^1$H-NMR (CDCl$_3$) δ 1.44 (s, 9H), 3.17 (m, 2H), 4.09 (app. q, J=4.41, 8.82 Hz, 1H), 6.67 (app. d, J=6.62 Hz, 2H), 6.99 (app. d, J=8.09 Hz, 2H), 7.17 (app. d, J=8.82 Hz, 2H), 7.33 (m, 6H), 7.54 (app. d, J=6.62 Hz, 2H). $^{13}$C-NMR (CDCl$_3$) δ 28.05, 38.93, 67.64, 81.30, 127.64, 127.98, 128.14, 128.34, 128.73, 130.23, 131.18, 132.04, 136.27, 136.94, 139.42, 170.56.

Preparation of 2-(Benzhydrylidene-amino)-3-(2-fluoro-5-methoxy-phenyl)-propionic acid tert-butyl ester (40).

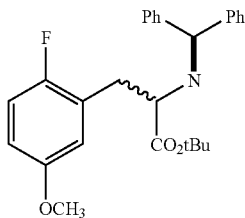

Compound 40 was made to serve as a reference compound for the [$^{18}$F]fluoro-derivative of 40. Initial PTC chemistry attempted to synthesize 40 was unsuccessful. Other routes were then investigated and described below m.p. 168–169° C.

$^1$H-NMR (CDCl$_3$) δ 1.45 (s, 9H), 3.12 (dd, 1H, J=9.56 Hz, 12.50 Hz, CH$_2$), 3.28 (dd, 1H, J$_{C-F}$=4.42 Hz, 13.24 Hz, CH$_2$), 3.61 (s, 3H), 4.18 (dd, 1H, J$_{C-F}$=4.41 Hz, 9.56 Hz), 6.62–6.70 (m, 3H), 6.82 (app. t, 1H, J$_{C-F}$=8.83 Hz), 7.27–7.36 (m, 7H), 7.58 (app. d, 2H, J$_{C-F}$=6.62 Hz). $^{13}$C-NMR (CDCl$_3$) δ 28.03, 32.86, 55.55, 66.19, 81.19, 113.67 (J$_{C-F}$=8.54 Hz), 115.46 (J$_{C-F}$=23.19 Hz), 116.39 (J$_{C-F}$=4.88 Hz), 125.84 (J$_{C-F}$=17.09 Hz), 127.69, 127.92, 128.08, 128.34, 128.74, 130.15, 137.87 (J$_{C-F}$=252.69 Hz), 155.19 (J$_{C-F}$=2.44 Hz), 157.37, 170.53. $^{19}$F-NMR (CDCl$_3$) δ-130.90. HRMS: Calcd for $C_{27}H_{29}FNO_3^+$ (Cation): 434.2132. Found: 434.2134.

Preparation of 40.

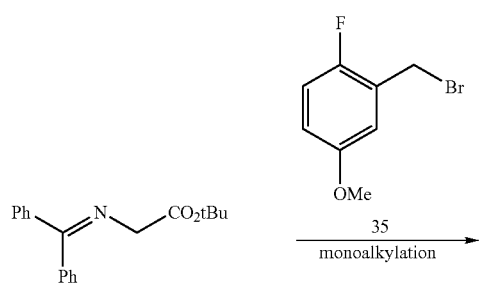

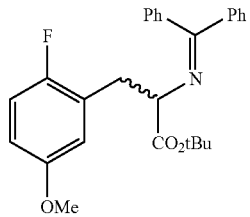

40

Five different base conditions were studied for the preparation of 40. These reaction procedures are discussed below. Of the five reactions, the best results (193 mg, 97%) were afforded by the LiHMDS/NaI/THF reaction, which also gave the cleanest crude product. The products from these reactions were analyzed by $^1$H-NMR.

A. Alkylation Using TBAH/10% NaOH/CH$_2$Cl$_2$.

Tetrabutylammonium sulfate (156.2 mg, 0.46 mmol) was added to a two-phase mixture consisting of 10% NaOH (2.5 mL), t-butylglycinate Schiff base 3 (142.7 mg, 0.48 mmol), and 2-fluoro-5-methoxybenzyl bromide 35 (100 mg, 0.46 mmol) in dichloromethane (2.0 mL). After 5 h of vigorous stirring at ambient temperature, the reaction mixture was diluted with ether (10 mL) and the layers were separated. The organic layer was washed with water (3×3.0 mL), dried over sodium sulfate, filtered, and evaporated in vacuo. A crude yellow oil of 40 was obtained in 90% yield. The pure product 40 was made as a residue in 83% (149 mg).

B. Alkylation Using LDA/DMPU/THF.

t-Butylglycinate Schiff base 3 (136 mg, 0.46 mmol) in a mixture of dry THF-DMPU 60:40 (2.5 mL) at −78° C. was treated with a 2.0 M LDA solution (0.23 mL, 0.46 mmol) and the mixture was stirred for one h at the same temperature. 2-Fluoro-5-methoxybenzyl bromide (35, 100 mg, 0.46 mmol) in dry THF (2.5 mL) was added dropwise at −78° C. and then the mixture was stirred overnight at room temperature. The reaction was quenched with saturated aqueous ammonium chloride (10 mL), and the product was extracted with diethyl ether (2×15 mL). The combined organic layers were washed with saturated aqueous ammonium chloride (4×10 mL), dried over sodium sulfate, filtered and evaporated to give 40 as a crude yellow oil (110%). When examined, the pure product 40 was made in 80% yield (175 mg).

C. Alkylation Using LiHMDS/NaI/THF.

LHMDS (92 mg, 0.55 mmol) was added to a solution of t-butylglycinate Schiff base 3 (136 mg, 0.46 mmol) in THF (1.5 mL) A mixture containing 2-fluoro-5-methoxy-benzyl bromide (35, 100 mg, 0.46 mmol) and sodium iodide (138 mg, 0.92 mmol) in THF (2.0 mL) was immediately added to the resulting enolate solution at −78° C. The combined mixture was warmed to room temperature, stirred for 2 h, diluted with 1:1 ether/pentane (25 mL), washed with brine (3×15 mL), dried (sodium sulfate) and concentrated to afford 40 as a crude yellow oil (108%). Once examined, the pure product was made in 97% yield (193 mg).

D. Alkylation Using KHMDS/THF.

KHMDS (550 μl of a 0.5 M solution in toluene, 0.55 mmol) diluted with dry THF (1.5 mL) was added to a solution of t-butylglycinate Schiff base 3 (68 mg, 0.23 mmol) in THF (1.5 mL). A mixture containing 2-fluoro-5- methoxybenzyl bromide (35, 50 mg, 0.23 mmol) in THF (1.0 mL) was immediately added to the resulting enolate solution at −78° C. The combined mixture was warmed to room temperature, stirred for 2 h, diluted with 1:1 ether/pentane (20 mL), washed with brine (3×10 mL), dried (sodium sulfate), filtered and then concentrated to afford 40 as a crude yellow oil (115%). Interestingly, a lower yield of 22% (40 mg) was obtained compared to using LiHMDS.

E. Alkylation Using $PhCH_2(CH_3)_3N^{+-}OH/KI$.

To a cold (10° C.) stirred solution of 2-fluoro-5-methoxybenzyl bromide (35, 50 mg, 0.23 mmol), t-butylglycinate Schiff base 3 (68 mg, 0.23 mmol) and potassium iodide (4.2 mg, 0.05 mmol) in dioxane (2.0 mL) was added dropwise over 30–45 min. benzyltrimethylammonium hydroxide (0.069 mL, 0.23 mmol, 40% aqueous). The reaction mixture was then brought to room temperature and stirred for an additional 3 h. After cooling to 0° C., water (2.0 mL) was added and the mixture was extracted with toluene (6×10 mL). The organic extracts were washed with water (20 mL) and dried over sodium sulfate. Evaporation of the solvent afforded a colorless oil, which was not purified (33%) and the alkylated product 40 was not obtained.

Deprotection of the Imine.

A. 2-[5-(3,5-bis-Trifluoromethyl-benzoyl)-2-nitro-phenyl]-1-tert-butoxycarbonyl-ethyl-ammonium; chloride (75).

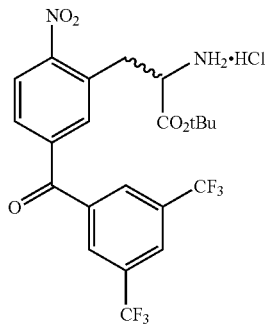

0.2 N Aqueous HCl in THF (10 mL) was added to a 25-mL single-necked pear-shaped flask containing the imine Schiff base 49 (503 mg, 0.75 mmole) and the mixture was stirred for 6 h at room temperature. The reaction mixture was concentrated and then diluted with water (50 mL) and mixed with diethyl ether (50 mL). The layers were separated and the desired product appeared as a white precipitate between the layers. First, the aqueous layer was removed. Secondly, the white solid and organic layer were separated by vacuum filtration. The solid was washed with cold ether (2×20 mL) and dried under high vacuum to give 75 (60% yield): m.p. 178–179° C.

$^1$H-NMR (CDCl$_3$/d-DMSO) δ 1.39 (s,9H), 3.68 (m, 2H), 4.30 (m, 1H), 7.74 (m, 1H), 8.15 (m, 3H), 8.32 (s, 1H), 9.03 (broad s, 2H). $^{13}$C-NMR (CD$_3$OD/CD$_3$CN) d 27.93, 34.74, 54.41, 85.70, 124.35 ($J_{C-F}$=272.22 Hz), 126.96, 127.69 ($J_{C-F}$=3.66 Hz), 131.09 ($J_{C-F}$=6.11 Hz), 131.45, 132.16, 133.30 ($J_{C-F}$=34.18 Hz), 135.55, 139.83, 141.49, 152.99, 168.44, 193.11. Anal. Calcd for C$_{22}$H$_{21}$ClF$_6$N$_2$O$_5$: C, 48.68; H, 3.90; N, 5.16. Found: C, 48.08; H, 3.85; N, 5.03.

B. 2-[5-(3,5-bis-Trifluoromethyl-benzoyl)-2-fluoro-phenyl]-1-tert-butoxycarbonyl-ethyl-ammonium; chloride (76).

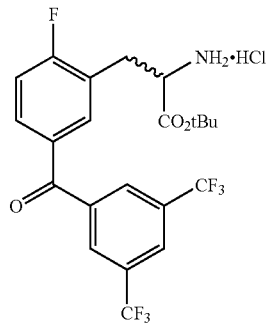

0.2 N Aqueous HCl in THF (5 mL) was added to a 15-mL single-necked pear-shaped flask containing the imine Schiff base 50 (295 mg, 0.46 mmole) and the mixture was stirred for 6 h at room temperature. The reaction mixture was concentrated and then diluted with water (10 mL) and extracted with diethyl ether (1×10 mL). The aqueous layer was neutralized with sodium bicarbonate and extracted with ethyl acetate (1×15 mL). The organic layer was separated, dried (MgSO$_4$), filtered and evaporated to give a white solid (194 mg, 88.4%): m.p. 207–208° C.

$^1$H-NMR (d-DMSO) δ 1.44 (s, 9H), 3.06 (dd, 1H, J=9.56, 13.97 Hz), 3.42 (dd, 1H, J=4.78, 13.60 Hz), 3.66 (dd, 1H, J=4.78, 9.19 Hz), 7.80 (dd, 1H, J=1.84, 8.46 Hz), 7.89 (d, 1H, J=1.47 Hz), 8.06 (d, 1H, J=8.83 Hz), 8.15 (s, 1H), 8.30 (s, 2H). $^{13}$C-NMR (d-DMSO) 27.22, 32.54, 52.56, 83.08, 117.96, 122.94 ($J_{C-F}$=272.22 Hz), 125.43, 126.53 ($J_{C-F}$=2.44 Hz), 129.90, 130.20 ($J_{C-F}$=3.66 Hz), 130.74, 130.83 ($J_{C-F}$=34.18 Hz), 134.43, 139.13 ($J_{C-F}$=98.88 Hz), 151.46, 167.37, 192.14. $^{19}$F-NMR (CD$_3$OD) δ−112.09, −66.18. HRMS: Calcd for C$_{22}$H$_{21}$F$_7$NO$_3$ (Cation): 480.1409. Found: 480.1416.

C. 2-[5-(3,5-bis-Trifluoromethyl-benzoyloxy)-2-fluoro-phenyl]-1-tert-butoxycarbonyl-ethyl-ammonium; chloride (142).

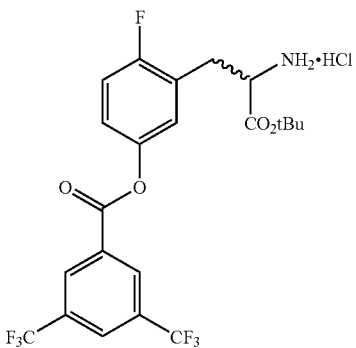

The HCl-salt was prepared in same manner as indicated above to give a 87% yield (46 mg): m.p. 220–221° C.

$^1$H-NMR (CD$_3$OD) δ 1.31 (s, 9H), 3.17 (m, 4H), 4.12 (app. t, J=7.35 Hz, 1H), 7.21 (m, 3H), 8.27 (s, 1H), 8.57 (s, 2H). $^{13}$C-NMR (CD$_3$OD) δ 27.99, 31.30, 54.23, 85.61, 117.67 ($J_{C-F}$=24.42 Hz), 124.25 ($J_{C-F}$=8.55 Hz), 124.37 ($J_{C-F}$=272.22 Hz), 124.57, 125.93 ($J_{C-F}$=4.88 Hz), 128.28 ($J_{C-F}$=3.66 Hz), 131.25 ($J_{C-F}$=3.66 Hz), 133.30, 133.63

($J_{C-F}$=34.18 Hz), 148.05, 160.59 ($J_{C-F}$=244.14 Hz), 163.90, 168.80. $^{19}$F-NMR (CD$_3$OD) δ −123.19, −66.53.

D. 1-tert-Butoxycarbonyl-2-(2-fluoro-5-methoxy-phenyl)-ethyl-ammonium: chloride (83).

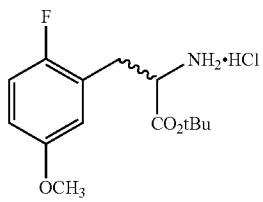

The HCl-salt was prepared in same manner as indicated above to give a 72% yield (472 mg): m.p. 162–163° C.

$^1$H-NMR (CD$_3$OD) δ 1.30 (s, 9H), 3.08 (d, J=7.36 Hz, 2H), 3.68 (s, 3H), 4.06 (t, J=7.36, 1H), 6.78 (m, 2H), 6.97 (m, 1H). $^{13}$C-NMR (CD$_3$OD) δ 27.99, 31.63 ($J_{C-F}$=2.44 Hz), 54.41, 56.32, 85.32 115.50 ($J_{C-F}$=7.33 Hz), 117.17 ($J_{C-F}$=23.19 Hz), 118.07 ($J_{C-F}$=3.67 Hz), 123.41 ($J_{C-F}$=17.09 Hz), 157.07 ($J_{C-F}$=236.81 Hz), 157.57 ($J_{C-F}$=2.44 Hz), 168.88. $^{19}$F-NMR (CDCl3) δ−131.69 HRMS: Calcd. for C$_{14}$H$_{21}$FNO$_3$ (Cation): 270.1505. Found: 270.1499.

Boc-Protection.

A. 3-[5-(3,5-bis-Trifluoromethyl-benzoyl)-2-nitro-phenyl]-2-tert-butoxycarbonylamino-propionic acid tert-butyl ester (52).

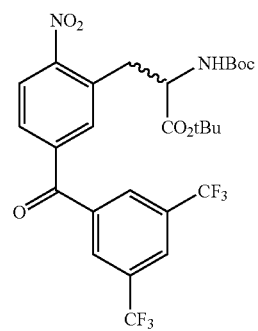

A mixture of the amino ester 75 (500 mg, 0.92 mmole), diisopropylethylamine (481 μl, 2.76 mmole), di-tert-butyl dicarbonate (241 mg, 1.11 mmole) and dry THF (5–10 mL) in a 25-mL pear-shaped flask was stirred overnight at room temperature. The solvent was removed in vacuo and the crude residue was purified by recrystallization from hexanes to give white crystals (515 mg, 92%): m.p. 176–177° C.

$^1$H-NMR (CDCl$_3$) δ 1.30 (s,9H), 1.45 (s, 9H), 3.21 (dd, J=9.19, 13.97 Hz, 1H), 3.61 (dd, J=5.15, 13.97 Hz, 1H), 4.58 (m, 1H), 5.22 (m, 1H), 7.76 (dd, J=1.47, 8.46 Hz, 1H), 7.86 (d, J=1.47 Hz, 1H), 8.08 (d, J=8.46, 1H), 8.16 (s, 1H), 8.27 (s, 2H). $^{13}$C-NMR (CDCl$_3$) δ 27.92, 28.10, 36.25, 60.39, 80.03, 82.95, 122.78 ($J_{C-F}$=273.44 Hz), 125.22, 126.47 ($J_{C-F}$=3.67 Hz), 128.92, 129.88 ($J_{C-F}$=3.66 Hz), 132.60 ($J_{C-F}$=34.18 Hz), 133.41, 134.64, 138.28, 139.01, 152.48, 154.98, 170.06, 191.73. $^{19}$F-NMR (CDCl$_3$) δ−65.70. HRMS: Calcd. for C$_{27}$H$_{29}$F$_6$N$_2$O$_7$ (Cation): 607.1878. Found: 607.1868.

B. 3-[5-(3,5-bis-Trifluoromethyl-benzoyl)-2-fluoro-phenyl]-2-tert-butoxycarbonylamino-propionic acid tert-butyl ester (77).

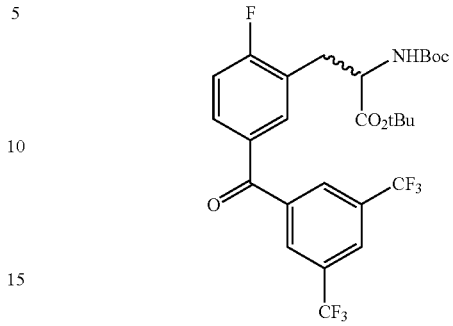

The reaction procedure was the same as that used to make 77 above. The pure product was obtained as a white solid (209 mg, 88.8%): m.p. 99–101° C.

$^1$H-NMR (CDCl$_3$) δ 1.30 (s, 9H), 1.45 (s, 9H), 3.21 (dd, 1H, J=8.83, 13.24 Hz), 3.60 (dd, 1H, J=5.15, 13.97 Hz), 4.57 (m, 1H), 5.21 (d, 1H, J=7.35 Hz), 7.75 (d, 1H, J=8.83 Hz), 7.85 (s, 1H), 8.07 (d, 1H, J=8.83 Hz), 8.16 (s, 1H), 8.27 (s, 2H). $^{13}$C-NMR (CDCl3) δ 27.95, 28.11, 82.96, 122.80 ($J_{C-F}$=273.44 Hz), 125.24, 126.48 ($J_{C-F}$=2.44 Hz), 128.94, 129.90 ($J_{C-F}$=2.44 Hz), 132.63 ($J_{C-F}$=34.18 Hz), 133.42, 134.65, 138.30, 139.04, 152.51, 154.98, 170.09, 191.75. $^{19}$F-NMR (CDCl$_3$) δ−109.87, −65.70. Anal. Calcd. for C$_{27}$H$_{28}$F$_7$NO$_5$: C, 55.96; H, 4.87; N, 2.42. Found: C, 55.65; H, 4.83; N, 2.39.

H$_2$/Pd Reduction of Aryl Nitro Compounds to Aryl Amines.

A. 3-[2-Amino-5-(3,5-bis-Trifluoromethyl-benzoyl)-phenyl]-2-tert-butoxycarbonylamino-propionic acid tert-butyl ester (58).

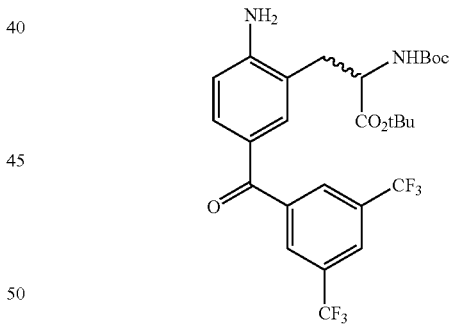

The nitrobenzophenone derivative 52 (0.7475 g, 1.23 mmol), isopropanol (40 mL), and 10% palladium on activated carbon (131 mg, 0.131 mmol) were added to a single-necked 200 mL pear-shaped round-bottom flask. The flask was sealed with a rubber septum and charge-purged three times using a hydrogen-filled balloon followed by house vacuum. The reaction vessel was equipped with two hydrogen-filled balloons and allowed to stir at room temperature for exactly 15 minutes. During this time a filter funnel was prepared with celite and packed with isopropanol. The reaction mixture was immediately vacuum filtered through the funnel into a 100 mL round-bottom flask.The solvent was removed in vacuo and the crude mixture was purified by flash chromatography (20% EtOAc: hexanes) to afford 58 as a yellow solid (0.631 g, 89%): m.p. 134–135° C.

$^1$H-NMR (CDCl$_3$) δ 1.34 (s, 9H), 1.45 (s, 9H), 2.86 (dd, J=9.56, 13.97 Hz, 1H), 3.11 (dd, J=2.21, 13.97 Hz, 1H), 4.27 (m, 1H), 5.53 (d, J=5.89 Hz, 1H), 6.65 (d, J=8.83 Hz, 1H), 7.45 (dd, J=2.20, 8.09, 1H), 7.59 (d, J=2.20 Hz, 1H), 8.03 (s, 1H), 8.13 (s, 2H). $^{13}$C-NMR (CDCl$_3$) δ 27.85, 28.37, 36.64, 52.72, 80.48, 83.01, 114.00, 120.55, 123.11 (J$_{C-F}$=272.22 Hz), 124.53 (J$_{C-F}$=3.67 Hz), 129.27 (J$_{C-F}$=30.66 Hz), 131.81 (J$_{C-F}$=34.18 Hz), 131.95, 132.04, 135.01, 141.22, 151.28, 155.87, 170.58, 191.62. $^{19}$F-NMR (CDCl$_3$) δ−65.16. HRMS: Calcd. for C$_{27}$H$_{30}$F$_6$N$_2$O$_5$: 576.2059. Found: 576.2054.

B. (4-Amino-3-methyl-phenyl)-([3,5-bis-trifluoromethyl-phenyl)-methanone (56).

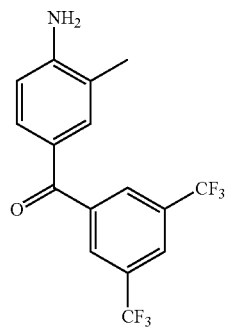

The nitrobenzophenone derivative 17 (0.13 g, 0.35 mmol), isopropanol (5 mL), and 10% palladium on activated carbon (54 mg, 0.035 mmol) were added to a single-necked 50 mL round-bottom flask. The hydrogenation and purification procedures were the same as above for compound 58. Product 56 was obtained as a yellow solid (120 mg, 100%): m.p. 170–171° C.

$^1$H-NMR (CD$_3$OD) δ 2.19 (s, 3H), 6.73 (dd, J=3.67, 8.09 Hz, 1H), 7.47 (d, J=8.82 Hz, 1H), 7.57 (broad s, 1H), 8.18 (broad s, 1H). $^{13}$C-NMR (CD$_3$OD) δ 17.40, 114.15, 122.28, 124.58 (J$_{C-F}$=272.22 Hz), 125.02, 125.38 (J$_{C-F}$=3.665 Hz), 130.33 (J$_{C-F}$=2.44 Hz), 132.32, 132.75 (J$_{C-F}$=34.18 Hz), 134.37, 143.09, 154.33, 193.44. $^{19}$F-NMR (CD$_3$OD) δ −66.25. HRMS: Calcd. for C$_{16}$H$_{11}$F$_6$NO: 347.0745. Found: 347.0741.

Reductive Methylation with NaBH$_3$CN to Form the Mono- and Dimethyl Amines (55).

A. 3-[5-(3,5-bis-Trifluoromethyl-benzoyl)-2-dimethylamino-phenyl]-2-tert-butoxycarbonylamino-propionic acid tert-butyl ester (55).

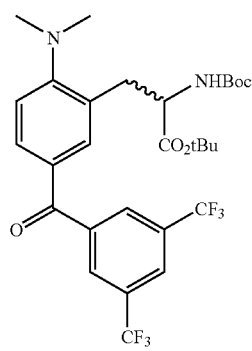

Method A

Aryl amine 58 (633 mg, 1.1 mmol) was added to a 100 mL round-bottom flask containing methanol (40 mL). Once the amine had been dissolved, 37% formaldehyde (1.03 mL, 22.0 mmol), sodium cyanoborohydride (828 mg, 13.2 μmol), and 0.1% bromocresol green (2–3 drops) were added and the mixture was stirred (argon-filled balloon). Acetic acid was slowly added to the reaction mixture by syringe until pH=4–5 was achieved (bright yellow color observed). When the pH was not carefully monitored and allowed to reach pH=5–6, only monomethylation was observed. The reaction was monitored by TLC until completion (approximately 8 h) and then the mixture was neutralized with saturated sodium bicarbonate. Methanol was removed in vacuo and diethyl ether was added (5 mL). The mixture was extracted with saturated sodium bicarbonate (3×3 mL) and with brine (1×3 mL). The ether phase was separated, dried with magnesium sulfate, filtered and the solvent was removed in vacuo to afford the crude product. If necessary, purification was accomplished by flash chromatography (10–20% EtOAc/hexanes) to give the pure product 55 as a yellow oil (0.625 g, 94%).

$^1$H-NMR (CD$_3$CN) δ 1.31 (s, 9H), 1.34 (s, 9H), 2.82 (s, 6H), 3.00 (dd, J=9.19, 14.34, 1H), 3.21 (dd, J=5.52, 14.34, 1H), 4.35 (m, 1H), 7.21 (m, 1H), 7.65 (m, 1H), 8.20 (s, 2H), 8.24 (s, 1H). $^{13}$C-NMR (CDCl$_3$) δ 27.89, 28.27, 35.85, 44.13, 54.35, 79.40, 81.72, 118.91, 123.02 (J$_{C-F}$=273.44 Hz), 125.16 (J$_{C-F}$=3.66 Hz), 129.61 (J$_{C-F}$=3.66 Hz), 129.92, 130.55, 131.34 (J$_{C-F}$=2.44 Hz), 131.99 (J$_{C-F}$=340.18 Hz), 133.94, 140.17, 155.16, 158.45, 171.24, 192.26. $^{19}$F-NMR (CDCl$_3$) δ −65.64. HRMS: Calcd. for C$_{29}$H$_{34}$F$_6$N$_2$O$_5$: 604.2372. Found: 604.2377.

B. 3-[5-(3,5-bis-Trifluoromethyl-benzoyl)-2-methylamino-phenyl]-2-tert-butoxycarbonylamino-propionic acid tert-butyl ester (143).

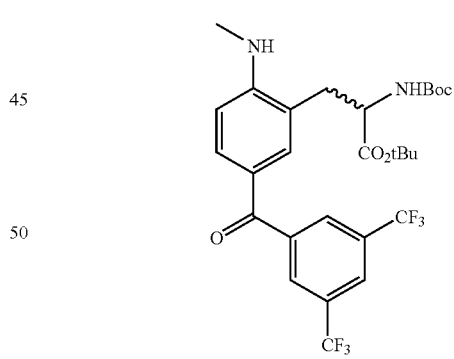

This product was isolated from a scaled-down run of the previous reaction to give compound 145 in 5% yield (19.6 mg).

$^1$H-NMR (CDCl$_3$) δ 1.34 (s, 9H), 1.47 (s, 9H), 2.85 (dd, J=10.3 Hz, 14.71 Hz, 1H), 3.00 (d, J=4.41 Hz, 3H), 3.09 (dd, J=2.21 Hz, 14.71 Hz, 1H), 4.19 (m, 1H), 5.54 (broad d, J=5.15 Hz, 1H), 6.44 (broad d, J=3.68 Hz, 1H), 6.57 (d, J=8.83 Hz, 1H), 7.54 (dd, J=2.21 Hz, 8.83 Hz, 1H), 7.61 (d, J=2.20 Hz, 1H), 8.02 (s, 1H), 8.13 (s, 2H). $^{13}$C-NMR (CDCl$_3$) δ 27.78, 28.32, 30.09, 36.63, 52.57, 80.42, 82.97, 120.78, 122.71, 123.09 (J$_{C-F}$=272.22 Hz), 124.23 (J$_{C-F}$=3.66 Hz), 126.90 (J$_{C-F}$=3.66 Hz), 129.17 (J$_{C-F}$=2.44 Hz), 131.65 (J$_{C-F}$=34.18 Hz), 132.79, 134.05, 141.51, 152.41, 155.94, 170.51, 191.40. $^{19}$F-NMR (CDCl$_3$) δ −65.63. HRMS: Calcd. for C$_{28}$H$_{32}$F$_6$N$_2$O$_5$: 590.2215. Found: 590.2219.

C. (3,5-bis-Trifluoromethyl-phenyl)-(4-dimethylamino-3-methyl-phenyl)-methanone (10).

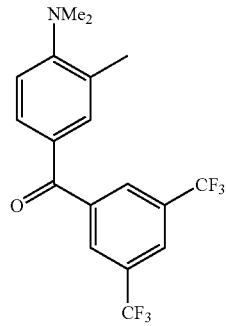

The preparation of 10 followed the same procedure indicated above for making compound 55. Purification was accomplished by flash chromatography (10–20% EtOAc/hexanes) to give the pure product 10 as a yellow oil (25.8 mg, 96%): m.p. 145–147° C.

$^1$H-NMR (CDCl$_3$) δ 2.38 (s, 3H), 2.87 (s, 6H), 6.99 (d, J=8.09 Hz, 1H), 7.55 (dd, J=2.21, 8.82 Hz, 1H), 7.67 (d, J=1.47 Hz, 1H), 8.06 (s, 1H), 8.20 (s, 2H). $^{13}$C-NMR (CDCl$_3$) δ 19.65, 43.22, 117.03, 123.09 (J$_{C-F}$=281.98 Hz), 124.86, 128.41, 129.51, 129.64, 130.48, 131.79 (J$_{C-F}$=34.18 Hz), 133.79, 140.56, 157.88, 192.45. $^{19}$F-NMR (CDCl$_3$) δ−65.48 HRMS: Calcd. for C$_{18}$H$_{16}$F$_6$N0 (cation): 376.1136. Found: 376.1134.

Method B.

A 100-ml three-necked round-bottom flask was connected to a mechanical stirrer and subsequently purged with nitrogen in an ice bath. Anhydrous AlCl$_3$ (0.96 g, 7.2 mmol) and dichloromethane (3.1 mL) were added and the mixture was stirred for 10 min at 0° C. N,N-Dimethyl toluidine (1.57 mL, 10.8 mmol) was introduced dropwise to the mixture over 15 minutes at 0° C. 3', 5'-Bis(trifluoromethyl)benzoyl chloride (0.66 mL, 3.6 mmol) in dichloromethane (3 mL) was added dropwise to the reaction over 20 minutes at 0° C. After complete addition of the reagents, the reaction was allowed to stir for 1 h at 60–65° C. The reaction was subjected to a series of extractions: deionized water and ice (1×25 mL), 30 M sodium citrate (3×30 mL), and deionized water (1×25 mL). The organic layer was dried with sodium sulfate, filtered and then evaporated to yield a crude greenish product (2.00 g, 147%). Purification was carried out with flash chromatography (hexane to 2:1 hexane/EtOAc) to give a yellow solid (0.700 g. 35%): m.p. 145–147° C.

D. N-Methyl-N-(2-methylphenyl)-3,5-bis(trifluoromethyl)benzamide (12).

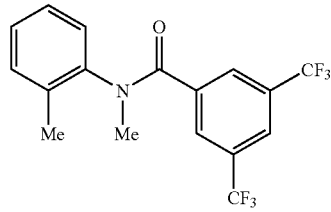

This side product was isolated from the previous reaction as a yellow solid (27.8 mg, 1%): m.p. 68–69° C.

$^1$H-NMR (CDCl$_3$) δ 2.12 (s, 3H), 3.35 (s, 3H), 7.08 (m, 4H), 7.65 (broad s, 3H). $^{13}$C-NMR (CDCl$_3$) δ 17.43, 37.54, 122.78 (J$_{C-F}$=273.44 Hz), 123.20 (J$_{C-F}$=3.66 Hz), 127.46, 128.32, 128.62, 131.02 (J$_{C-F}$=34.18 Hz), 131.69, 134.61, 137.67, 142.30, 167.34. $^{19}$F-NMR (CDCl$_3$) δ−65.99 IR (NaCl plates): 3079, 2930, 1650, 1494 cm$^{-1}$. HRMS: Calcd. for C$_{17}$H$_{13}$F$_6$N0: 361.0901. Found: 361.0919.

E. (3,5-bis-Trifluoromethyl-phenyl)-(3-methyl-4-methylamino-phenyl)-methanone (59).

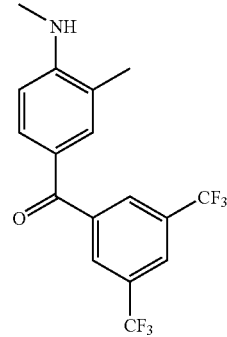

Compound 59 was isolated from a reductive methylation reaction for the preparation of 10. The residue was obtained in 37% yield (19 mg).

$^1$H-NMR (CDCl$_3$) δ 2.18 (s, 3H), 3.01 (d, J=5.15 Hz, 3H), 4.33 (m, 1H), 6.60 (d, J=8.83 Hz, 1H), 7.59 (dd, J=2.21, 8.83 Hz, 1H), 7.64 (s, 1H), 8.03 (s, 1H), 8.15 (s, 2H). $^{13}$C-NMR (CDCl$_3$) δ 17.20, 24.00, 107.72, 121.46, 123.15 (J$_{C-F}$=272.22 Hz), 124.04, 124.40, 129.36, 131.58 (J$_{C-F}$=34.18 Hz), 131.91, 132.31, 141.35, 152.07, 191.91. $^{19}$F-NMR (CDCl$_3$) δ−65.70 HRMS: Calcd. for C$_{17}$H$_{13}$F$_6$N0: 361.0901. Found: 361.0897.

F. (3,5-bis-Trifluoromethyl-phenyl)-(4-dimethylamino-phenyl)-methanone (9).

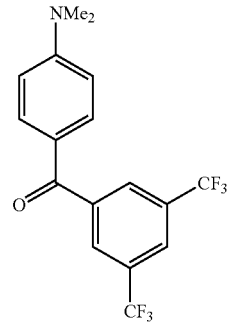

The preparation of 9 followed Method B used to make compound 10. A yellow solid was obtained in 57% yield (367 mg): m.p. 129–131° C.

$^1$H-NMR (CDCl$_3$) δ 3.11 (s, 6H), 6.71 (d, J=8.83 Hz, 2H), 7.74 (d, J=8.82 Hz, 2H), 8.02 (s, 1H), 8.16 (s, 2H). $^{13}$C-NMR (CDCl$_3$) δ 40.01, 110.88, 123.10 (J$_{C-F}$=273.44 Hz), 123.13, 124.34 (J$_{C-F}$=3.67 Hz), 129.30 (J$_{C-F}$=2.44 Hz), 131.64 (J$_{C-F}$=34.18 Hz), 132.72, 141.31, 153.91, 191.48. $^{19}$F-NMR (CDCl$_3$) δ−65.74 HRMS: Calcd. for C$_{17}$H$_{13}$F$_6$N0: 361.0901. Found: 361.0919.

G. (3,5-bis-Trifluoromethyl-phenyl)-bis-(4-dimethylamino-phenyl)-methanol (11).

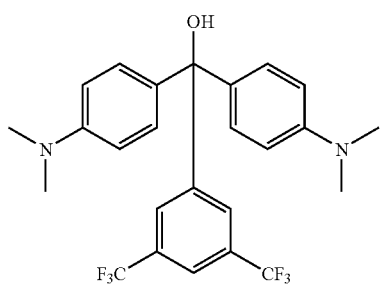

The blue residue 11 was isolated from the previous reaction in 36% yield (235 mg).

$^1$H-NMR (CDCl$_3$) δ 2.94 (s, 12H), 6.65 (d, J=8.83 Hz, 4H), 7.06 (d, J=8.83 Hz, 4H), 7.75 (s, 1H), 7.89 (s, 2H). $^{13}$C-NMR (CDCl$_3$) δ 40.36, 81.09, 111.89, 120.57 (J$_{C-F}$=3.66 Hz), 123.52 (J$_{C-F}$=273.44 Hz), 127.82 (J$_{C-F}$=2.44 Hz), 128.66, 130.77 (J$_{C-F}$=3.37 Hz), 133.81, 149.86, 150.70. $^{19}$F-NMR (CDCl$_3$) δ−65.34 HRMS: Calcd. for C$_{25}$H$_{24}$F$_6$N$_2$0: 482.1793. Found: 482.1813.

Free Amino Acid From Alkylated Compounds.

A. Trifluoro-acetate 2-[5-(3,5-bis-trifluoromethyl-benzoyl)-2-dimethylamino-phenyl]-1-methoxycarbonyl-ethyl-ammonium (81).

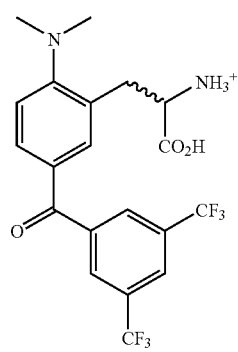

Trifluroacetic acid (3–5 mL) was added to the aryl amine 55 (184 mg, 0.304 mmol) in a 25 mL round-bottom flask equipped with a magnetic stirrer. The mixture was stirred at room temperature for 4–6 h. TFA was removed in vacuo (hood and pump) to give the di-TFA-salt of the deprotected amino acid. The salt was dissolved in methanol and eluted several times through a column prepared with Reillex-425 polyvinylpyridine (PVP) beads. Methanol was removed to give 81 as a yellow residue (136 mg, 100%).

$^1$H-NMR (d-DMSO) δ 2.77 (s, 6H), 2.97 (dd, J=8.82, 14.71 Hz, 1H), 3.41 (dd, J=4.42, 13.98 Hz, 1H), 3.95 (m, 1H), 7.21 (m, 1H), 7.65 (m, 1H), 8.25 (s, 2H), 8.40 (s, 1H). $^{13}$C-NMR (d-DMSO) δ 32.55, 42.66, 51.35, 53.80, 118.05, 121.96 (J$_{C-F}$=273.44 Hz), 124.16 (J$_{C-F}$=30.67 Hz), 128.14, 128.34, 128.5, 129.39, 129.48 (J$_{C-F}$=34.18 Hz), 132.49, 139.27, 159.82, 169.35, 190.860. HRMS: Calcd. for C$_{20}$H$_{19}$F$_6$N$_2$O$_3$ (Cation): 449.1300. Found: 449.1288.

B. Trifluoro-acetate 2-[5-(3,5-bis-trifluoromethyl-benzoyl)-2-fluoro-phenyl]-1-tert-butoxycarbonyl-ethyl-ammonium (79).

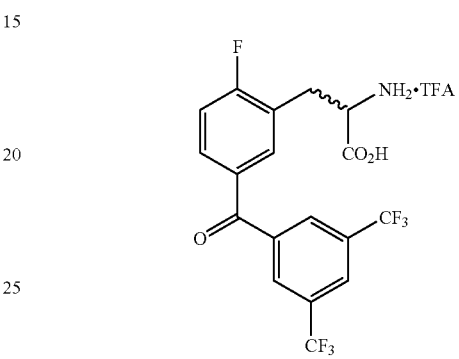

The HCl-salt was treated with concentrated TFA, as indicated above for making compound 81, to cleave the t-butyl ester protecting group to give 79 as a white solid in 99% yield (240 mg): m.p. 165–167° C.

$^1$H-NMR (d-TFA) δ 3.59 (dd, J=8.46, 15.01 Hz, 1H), 3.81 (dd, J=5.51, 15.01 Hz, 1H), 4.82 (m, 1H), 7.381 (m, 1H), 7.89 (m, 1H), 8.10 (m, 1H), 8.28 (s, 1H), 8.31 (s, 2H). $^{13}$C-NMR (d-TFA) δ 31.71, 56.02, 118.85 (J$_{C-F}$=24.42 Hz), 123.84 (J$_{C-F}$=15.87 Hz), 124.82 (J$_{C-F}$=272.21 Hz), 129.26 (J$_{C-F}$=3.665 Hz), 131.94 (J$_{C-F}$=2.44 Hz), 134.82 (J$_{C-F}$=3.67 Hz), 135.42 (J$_{C-F}$=34.18 Hz), 136.23 (J$_{C-F}$=10.99 Hz), 136.57 (J$_{C-F}$=4.88 Hz), 139.93, 167.71 (J$_{C-F}$=256.35 Hz), 174.02, 199.23. $^{19}$F-NMR (CD$_3$OD) δ−112.22, −66.43. HRMS: Calcd. for C$_{18}$H$_{13}$F$_7$NO$_3$ (Cation): 424.0783. Found: 424.0805.

C. Trifluoro-acetate 2-[5-(3,5-bis-trifluoromethyl-benzoyloxy)-2-fluoro-phenyl]-1-tert-butoxycarbonyl-ethyl-ammonium (108).

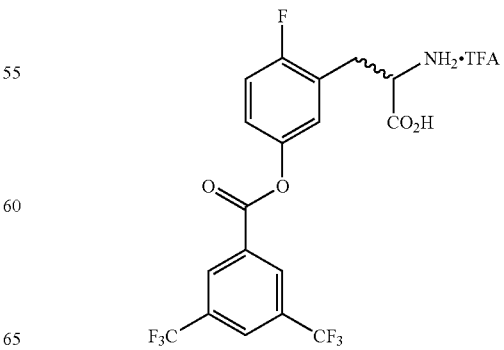

The HCl-salt was treated with concentrated TFA, as indicated above for making compound 81, to cleave the t-butyl ester protecting group to give 108 in 99% yield (47 mg).

$^1$H-NMR (d-TFA) δ 3.55 (dd, J=8.09, 15.01 Hz, 1H), 3.83 (dd, J=5.15, 14.71 Hz, 1H), 4.84 (dd, J=5.15, 9.09 Hz, 1H), 7.38 (m, 3H), 8.35 (s, 1H), 8.78 (s, 2H). $^{13}$C-NMR (d-TFA) δ 831.13, 55.79, 119.03 ($J_{C-F}$=25.64 Hz), 122.86, 123.09, 122.32 ($J_{C-F}$=272.27 Hz), 125.51 ($J_{C-F}$=9.77 Hz), 126.29 ($J_{C-F}$=3.66 Hz), 129.73 ($J_{C-F}$=3.66 Hz), 131.74, 135.13 ($J_{C-F}$=35.40 Hz), 148.26 ($J_{C-F}$=2.45 Hz), 159.95, 167.67, 173.68.

D. Trifluoro-acetate 2-[5-(3,5-bis-trifluoromethyl-benzoyl)-2-nitro-phenyl]-1-tert -butoxycarbonyl-ethyl-ammonium (78).

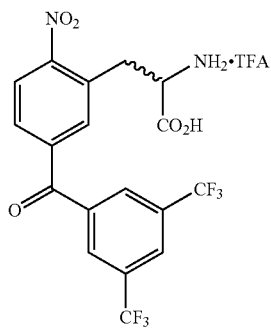

The HCl-salt was treated with concentrated TFA, as indicated above for making compound 81, to cleave the t-butyl ester protecting group to give 78 in 99% yield (272 mg). m.p. 162–163° C.

$^1$H-NMR (d-TFA) δ 3.81 (m, 1H), 4.04 (m, 1H), 4.97 (app broad s, 1H), 7.98 (m, 1H), 8.27 (m, 5H). $^{13}$C-NMR (d-TFA) δ 35.39, 56.77, 124.94 ($J_{C-F}$=272.22 Hz), 128.77, 130.13, 132.33, 133.57, 135.89 ($J_{C-F}$=34.18 Hz), 137.02, 139.24, 143.08, 154.21, 173.95, 197.98. $^{19}$F-NMR (CD$_3$OD) δ−66.43 HRMS: Calcd. for C$_{20}$H$_{13}$F$_6$N$_2$O$_5$ (Cation): 451.0728. Found: 451.0711.

E. 1-Carboxy-2-(2-fluoro-5-hydroxy-phenyl)-ethyl-ammonium: bromide (85).

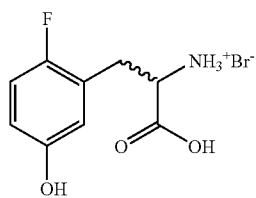

The HCl-salt was treated with 48% HBr to cleave the t-butyl ester and methyl ether protecting groups to give 85 in 93% yield (383 mg).

$^1$H-NMR (D$_2$O) δ 3.13 (dd, J=7.35, 14.71 Hz, 1H), 3.31 (dd, J=5.88, 14.71 Hz, 1H), 4.28(m, 1H), 6.77 (m, 2H), 7.01 (m, 1H).

HFA Products.

A. 4-[5-(3,5-bis-Trifluoromethyl-benzoyl)-2-dimethylamino-benzyl]-2,2-bis-trifluoromethyl-oxazolidin-5-one (82).

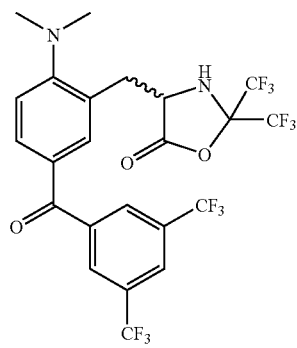

A 0.6 M solution of hexafluoroacetone (HFA) was prepared in EtOAc using an ice bath. Since HFA is a highly toxic gas, careful measures were taken to reduce chances of chemical exposure. All the teflon lines and connections were frequently checked and purged with nitrogen before and after use to prevent any problems due to the formation of hexafluorodiol from HFA and water. Since HFA remains more soluble in EtOAc at 0° C. than at ambient temperature, the HFA/solution is always maintained at 0° C. Subsequently, the cold HFA/EtOAc solution (10 mL, 0.6 M) was added to a 10-mL pear-shaped round-bottom flask containing the amino acid 11 (166 mg, 0.370 mmol) and a spin vane. The vessel was sealed with a rubber stopper and parafilm. The mixture was allowed to stir for 24 h at 0° C. to room temperature by allowing the ice bath to melt. The HFA/EtOAc solution was removed in vacuo and the crude mixture was purified by flash chromatography (20% EtOAc: hexanes) to give a yellow oil (0.205 g, 93%).

$^1$H-NMR (CDCl$_3$) δ 2.82 (s, 6H), 3.29 (m, 2H), 4.06 (m, 1H), 5.26 (d, J=5.15 Hz, 1H), 7.29 (m, 1H), 7.71 (m, 2H), 8.11 (s, 1H), 8.19 (s, 2H). $^{13}$C-NMR 14.16, 29.74, 34.80, 44.47, 57.19, 120.30, 120.35 ($J_{C-F}$=286.05 Hz), 121.02 ($J_{C-F}$=286.87 Hz), 122.94 ($J_{C-F}$=273.44 Hz), 125.67 ($J_{C-F}$=3.66 Hz), 129.65 ($J_{C-F}$=2.45 Hz), 131.39, 132.07, 132.21 ($J_{C-F}$=34.18 Hz), 133.75, 139.50, 157.69, 171.48, 192.39. $^{19}$F-NMR (CDCl$_3$) δ−83.90, −83.53, −64.10.

B. 4-[5-(3,5-bis-Trifluoromethyl-benzoyl)-2-fluoro-benzyl]-2,2-bis-trifluoromethyl-oxazolidin-5-one (95).

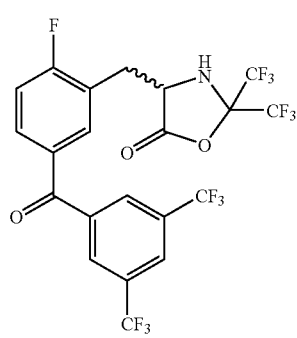

The preparation of 95 followed the same procedure indicated above for making compound 82. Purification was accomplished by flash chromatography (20% EtOAc/hexanes) to give the pure product 95 as a yellow oil (243 mg, 95%).

¹H-NMR (CDCl₃) δ 3.04 (dd, J=7.36, 13.97 Hz, 1H), 3.25 (d, J=6.62 Hz, 1H), 3.39 (dd, J=4.79, 13.97 Hz, 1H), 4.35 (m, 1H), 7.27 (m, 1H), 7.74 (m, 2H), 8.12 (s, 1H), 8.18 (s, 2H). ¹³C-NMR (CDCl₃) δ 29.69, 32.24, 54.48, 116.34 ($J_{C-F}$=23.20 Hz), 119.97 ($J_{C-F}$=284.65 Hz), 122.24 ($J_{C-F}$=273.44 Hz), 123.37 ($J_{C-F}$=15.87 Hz), 125.94 ($J_{C-F}$=3.67 Hz), 129.61, 131.93 ($J_{C-F}$=9.77 Hz), 132.34 ($J_{C-F}$=34.18 Hz), 132.69 ($J_{C-F}$=2.44 Hz), 134.02 ($J_{C-F}$=6.10 Hz), 139.02, 164.54 ($J_{C-F}$=255.13 Hz), 169.62, 191.95. ¹⁹F-NMR (CDCl₃) δ−109.957, −83.009, −82.360, −65.054 HRMS: Calcd. for $C_{21}H_{11}F_{13}NO_3$ (Cation): 572.0531. Found: 572.0512.

C. 4-[5-(3,5-bis-Trifluoromethyl-benzoyl)-2-nitro-benzyl]-2,2-bis-trifluoromethyl-oxazolidin-5-one (72).

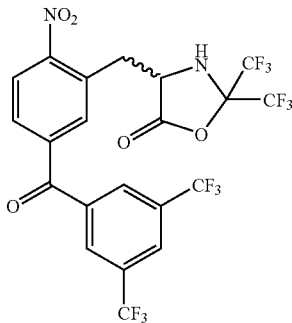

The preparation of 72 followed the same procedure indicated above for making compound 55. Purification was accomplished by flash chromatography (20% EtOAc/hexanes) to give the pure product 72 as a yellow oil (120 mg, 90%).

¹H-NMR (CDCl₃) δ 3.31 (m, 2H), 3.83 (dd, J=6.62, 13.98 Hz, 1H), 4.49 (dd, J=5.89, 12.51, 1H), 7.74 (d, J=2.21 Hz, 1H), 7.88 (dd, J=2.20, 8.82 Hz, 1H), 8.19 (m, 4H). ¹³C-NMR (CDCl₃) δ 35.35, 54.88, 119.93 ($J_{C-F}$=284.43 Hz), 121.10 ($J_{C-F}$=286.87 Hz), 122.75 ($J_{C-F}$=273.44), 126.84 ($J_{C-F}$=3.67 Hz), 129.78 ($J_{C-F}$=3.67 Hz), 132.78 ($J_{C-F}$=34.18 Hz), 134.59, 137.90, 140.06, 152.38, 169.58, 191.55. ¹⁹F-NMR (CDCl₃) δ−83.56, −82.66, −65.47. HRMS: Calcd. for $C_{21}H_{11}F_{12}N_2O_5$ (Cation): 599.0476. Found: 599.0495.

Procedure for the Preparation of Trimethylammonium Triflate Salts.

A. Trifluoro-methanesulfonate[4-(3,5-bis-trifluoromethyl-benzoyl)-2-(5-oxo-2,2-bis-trifluoromethyl-oxazolidin-4-yl-methyl)-phenyl]-trimethyl-ammonium (39).

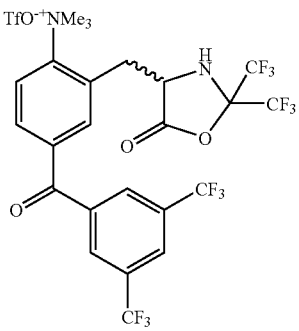

The aryl amine 82 (99 mg, 0.166 mmol) and 2,6 di-tert-butyl-4-methyl-pyridine (20 mg, 0.097 mmol) were placed into an argon-purged 15-mL pear shaped round-bottom flask equipped with a spin vane. Methyl triflate (0.300 mL, 2.65 mmol) was added at room temperature and then the mixture was heated to 65–70° C. for 1.5 h. MeOTf was removed by vacuum and the residue was rinsed with pentane (3×5 mL). The solvent was again removed by vacuum to afford a MeOTf-free residue. Dry EtOAc (10 mL) was added to precipitate the protonated base, which was subsequently filtered to give an EtOAc mixture. Activated carbon was added and the mixture was stirred overnight. The mixture was filtered through celite to give a light yellow oil. EtOAc was removed by vacuum. The oil was mixed with pentane/dichloromethane to afford a white solid (101 mg, 80%): m.p. 117–119° C.

¹H-NMR (CD₃CN) δ 3.57 (m, 2H), 3.72 (s, 9H), 4.62 (m, 1H), 7.88 (dd, J=2.21, 8.82 Hz, 1H), 7.99 (dd, J=2.21, 8.83 Hz, 2H), 8.31 (broad s, 2H), 8.33 (broad s, 1H). ¹³C-NMR (CD₃CN) δ 28.92, 37.22, 56.63, 59.39, 121.34 ($J_{C-F}$=284.42 Hz), 122.16 ($J_{C-F}$=289.31 Hz), 123.06, 124.16 ($J_{C-F}$=272.21 Hz), 127.50 ($J_{C-F}$=3.66 Hz), 130.90, 131.09 ($J_{C-F}$=3.66 Hz), 131.86, 132.67 ($J_{C-F}$=32.96 Hz), 136.93, 139.22, 139.70, 149.34, 170.71, 193.15. ¹⁹F-NMR (CD₃CN) −83.30, −82.17, −81.19, −65.24. HRMS: Calcd. for $C_{24}H_{19}F_{12}N_2O_3$ (Cation): 611.1204. Found: 611.1203.

B. Trifluoro-methanesulfonate(4-methoxy-2-methyl-phenyl)-trimethyl-ammonium (62).

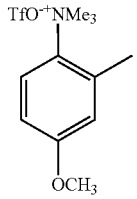

Dimethylamine (200 mg, 0.55 mmole), dissolved in dry dichloromethane (2 mL), and methyl triflate (125 μL, 1.11 mmole) were added to a 15 mL single-necked pear-shaped flask equipped with a spin vane. The mixture was stirred overnight at room temperature, filtered and the white crystals were washed with cold pentane. Recrystallization from diethyl ether and dichloromethane (1:1) gave white needles (3.6 g, 86%): m.p. 81–83° C.

¹H-NMR (CDCl₃) δ 2.71 (s, 3H), 3.73 (s, 9H), 3.81 (s, 3H), 6.85 (m, 2H), 7.69 (app. t., 1H, $J_{C-F}$=4.78 Hz). ¹³C-NMR (CDCl₃) δ 23.16, 55.72, 57.65, 112.55, 120.78 ($J_{C-F}$=319.82 Hz), 121.38, 121.91, 131.42, 138.16, 160.20. Anal. Calcd. for $C_{12}H_{18}F_3NO_4S$: C, 43.76; H, 5.51; N, 4.25. Found: C, 43.59; H, 5.48; N, 4.14.

C. Trifluoro-methanesulfonate(4-acetoxy-2-methyl-phenyl)-trimethyl-ammonium (64).

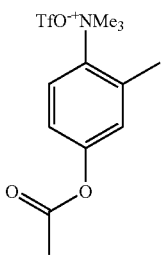

Compound 64 was prepared in the same manner as 62 to give white crystals. in 73% yield (76 mg): m.p. 135–136° C.
$^1$H-NMR (CDCl$_3$/DMSO) δ 2.35 (s, 3H, CH$_3$), 2.76 (s, 3H, OCH$_3$), 3.74 (s, 9H), 7.21 (dd, $J_{C-F}$=2.94 Hz, 9.56 Hz, 1H), 7.27 (d, $J_{C-F}$=2.94 Hz, 1H), 7.85 (d, $J_{C-F}$=8.83 Hz, 1H). $^{13}$C-NMR (CDCl$_3$/DMSO) δ 20.96, 23.12, 57.45, 121.41, 121.96, 128.84, 131.83, 142.16, 151.51, 168.61. Anal. Calcd. for C$_{13}$H$_{18}$F$_3$NO$_5$S: C, 43.70; H, 5.08; N, 3.92. Found: C, 43.79; H, 5.06; N, 3.92.

D. Trifluoro-methanesulfonate[4-(3,5-bis-trifluoromethyl-benzoyl)-phenyl]-trimethyl-ammonium (66).

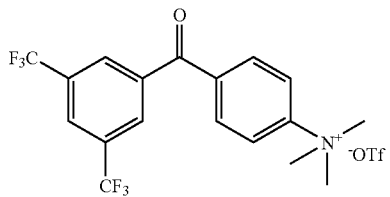

Compound 66 was prepared in the same manner as 62 to give white crystals.in 78% yield (289 mg): m.p. 168–169° C.
$^1$H-NMR (CDCl$_3$/d-DMSO) δ 3.37 (s, 9H, $^+$NMe3), 8.05 (d, 2H, $J_{C-F}$=8.80 Hz), 8.20 (d, 2H, $J_{C-F}$=9.70 Hz), 8.31 (s, 2H), 8.53 (s, 1H). $^{13}$C-NMR (CDCl$_3$/d-DMSO) δ 56.97, 121.31, 122.75 ($J_{C-F}$=272.22 Hz), 126.13 ($J_{C-F}$=3.66 Hz), 129.77 ($J_{C-F}$=3.66 Hz), 131.57, 131.87 ($J_{C-F}$=34.18 Hz), 137.33, 138.35, 150.25, 191.44. $^{19}$F-NMR (CD$_3$CN) δ–81.054, –65.314. Anal. Calcd. for C$_{19}$H$_{16}$F$_9$NO$_4$S: C, 43.44; H, 3.07; N, 2.67. Found: C, 43.64; H, 3.00; N, 2.62.

E. Trifluoro-methanesulfonate[4-(3,5-bis-trifluoromethyl-benzoyl)-2-methyl-phenyl]-trimethyl-ammonium (89).

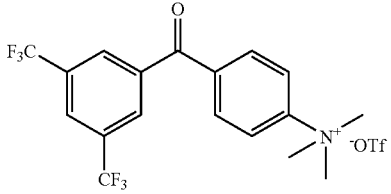

yield (139 mg, 96%)
$^1$H-NMR (CD$_3$CN) δ 2.78 (s, 3H), 3.70 (s, 9H), 7.79 (dd, J=8.83 Hz, 2H), 7.93 (d, J=8.83 Hz, 1H), 8.27 (m, 3H). $^{13}$C-NMR (CD$_3$CN) δ 23.27, 57.98, 121.55, 122.43, 124.00 ($J_{C-F}$=272.22 Hz), 127.16 ($J_{C-F}$=3.66 Hz), 129.92, 130.50, 130.89 ($J_{C-F}$=2.44 Hz), 132.42 ($J_{C-F}$=34.18 Hz), 134.52, 137.83, 139.12 ($J_{C-F}$=78.13 Hz), 148.99, 193.05. $^{19}$F-NMR (CD$_3$CN) δ–81.33, –65.36. HRMS: Calcd. for C$_{19}$H$_{18}$F$_6$NO$^+$: 390.1293. Found: 390.1288.

Miscellaneous

A. 3-Methyl-4-nitrophenyl 4-methylbenzenesulfonate (112).

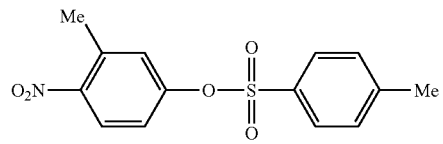

m.p. 75–76° C. yield: (14 g, 100%) $^1$H-NMR (CDCl$_3$) δ 2.47 (s, 3H), 2.55 (s, 3H), 6.94 (dd, J=2.94, 8.82 Hz, 1H), 7.06 (d, J=2.21 Hz, 1H), 7.36 (d, J=8.09 Hz, 2H), 7.74 (d, J=8.09 Hz, 2H), 7.92 (d, J=9.56 Hz, 1H). $^{13}$C-NMR (CDCl$_3$) δ 20.56, 21.73, 120.54, 126.30, 126.53, 128.45, 130.10, 131.94, 136.25, 146.16, 147.33, 152.14. HRMS: Calcd. for C$_{14}$H$_{13}$NO$_5$S: 307.0514. Found: 307.0511.

While the invention has been illustrated and described in detail in the drawings and foregoing description, such illustration and description is to be considered as exemplary and not restrictive in character, it being understood that only the preferred embodiments have been shown and described and that all changes and modifications that come within the spirit of the invention are desired to be protected.

What is claimed is:
1. A compound having the formula:

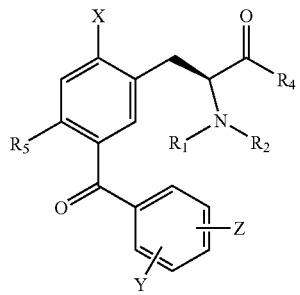

wherein R$_1$ is hydrogen, acyloxymethyl of 1–4 carbons, formyl, acyl, polyfluoroacyl of 2–3 carbons, optionally substituted alkyl and aryl sulfonyl, optionally substituted alkyl and aryl phosphoryl, or R$_1$ together with R$_4$ and —N—C$_α$—C(O)— forms a 4–7 membered ring, with bridging atoms being C, O, N, P, or S, or combinations thereof;

R$_2$ is hydrogen, C$_2$–C$_7$ normal, branched, cyclic saturated, cyclic unsaturated alkyl and alkoxyalkyl, optionally substituted tert-butyloxycarbonyl, optionally substituted benzyloxycarbonyl, formyl, acyl, polyfluoroacyl of 2–3 carbons, optionally substituted alkyl and aryl sulfonyl, or optionally substituted alkyl and aryl phosphoryl;

R$_4$ is OtBu, OCH$_3$, C$_2$–C$_7$ normal, branched, cyclic saturated, cyclic unsaturated alkoxy, and or R$_4$ together with R$_1$ and —N—C$_α$C(O)— forms a 4–7 membered ring, with bridging atoms being C, O, N, P, or S, or combinations thereof;

X is halogen, NO$_2$, N$_2^+$, N$^+$(CH$_3$)$_3$, S$^+$(CH$_3$)$_2$, or aryl iodonium;

Y is hydrogen, fluorinated alkyl, or $NO_2$;
Z is fluorinated alkyl or $NO_2$; and
$R_5$ is hydrogen, OtBu, $OCH_3$, $C_2$–$C_7$ normal, branched, cyclic saturated, or cyclic unsaturated alkoxy, acyl, halogen, azide or acylamide.

2. The compound of claim 1, wherein X is $-N^+(CH_3)_3$.

3. The compound of claim 2, wherein Y is $CF_3$ and Z is $CF_3$.

4. The compound of claim 3, wherein:
$R_1$ is hydrogen;
$R_2$ is tert-butyloxycarbonyl; and
$R_4$ is $OCH_3$.

5. The compound of claim 4, wherein $R_5$ is hydrogen.

6. The compound as defined in claim 1 which has the formula:

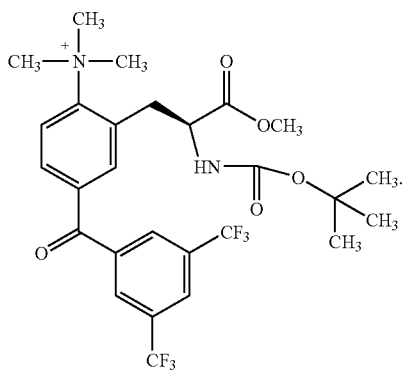

7. A compound having the formula:

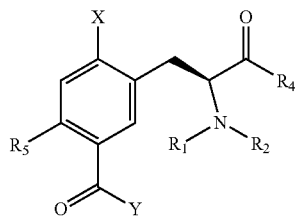

wherein X is a leaving group which allows nucleophilic radiofluorination at the position of X in the presence of soluble reactive [$^{18}$F]fluoride ion;
Y is a radical which contains one or more electron-withdrawing groups that result in an oxygen directly attached to the aromatic ring para to leaving group X when said compound is subjected to a Baeyer-Villiger Reaction;
$R_1$ is hydrogen, acyloxymethyl of 1–4 carbons, formyl, acyl, polyfluoroacyl of 2–3 carbons, optionally substituted alkyl and aryl sulfonyl, optionally substituted alkyl and aryl phosphoryl, or $R_1$ together with $R_4$ and $-N-C_\alpha-C(O)-$ forms a 4–7 membered ring, with bridging atoms being C, O, N, P, or S, or combinations thereof;
$R_2$ is hydrogen, $C_2$–$C_7$ normal, branched, cyclic saturated, cyclic unsaturated alkyl and alkoxyalkyl, optionally substituted tert-butyloxycarbonyl, optionally substituted benzyloxycarbonyl, formyl, acyl, polyfluoroacyl of 2–3 carbons, optionally substituted alkyl and aryl sulfonyl, or optionally substituted alkyl and aryl phosphoryl;

$R_4$ is OtBu, $OCH_3$, $C_2$–$C_7$ normal, branched, cyclic saturated, cyclic unsaturated alkoxy, or $R_4$ together with $R_1$ and $-N-C_\alpha-C(O)-$ forms a 4–7 membered ring, with bridging atoms being C, O, N, P, or S, or combinations thereof;
$R_5$ is hydrogen or a radical that can be converted to a phenolic OH group during or after said Baeyer-Villiger Reaction.

8. The compound of claim 7, wherein:
$R_1$ is hydrogen;
$R_2$ is tert-butyloxycarbonyl; and
$R_4$ is $OCH_3$ or OtBu.

9. The compound of claim 8, wherein Y has the formula:

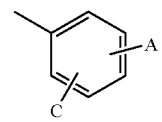

wherein A is hydrogen, fluorinated alkyl, or $NO_2$, and C is fluorinated alkyl or $NO_2$.

10. A kit for providing a radiolabeled Positron Emission Tomography imaging agent, said kit comprising:
a first container which contains a compound having the formula

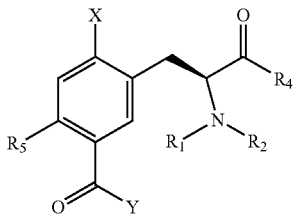

wherein X is a leaving group which allows nucleophilic radiofluorination at the position of X in the presence of soluble reactive [$^{18}$F]fluoride ion;
Y is a radical which contains one or more electron-withdrawing groups that result in an oxygen directly attached to the aromatic ring para to leaving group X when said compound is subjected to a Baeyer-Villiger Reaction;
$R_1$ is hydrogen, acyloxymethyl of 1–4 carbons, formyl, acyl, polyfluoroacyl of 2–3 carbons, optionally substituted alkyl and aryl sulfonyl, optionally substituted alkyl and aryl phosphoryl, or $R_1$ together with $R_4$ and $-N-C_\alpha-C(O)-$ forms a 4–7 membered ring, with bridging atoms being C, O, N, P, or S, or combinations thereof;
$R_2$ is hydrogen, $C_2$–$C_7$ normal, branched, cyclic saturated, cyclic unsaturated alkyl and alkoxyalkyl, optionally substituted tert-butyloxycarbonyl, optionally substituted benzyloxycarbonyl, formyl, acyl, polyfluoroacyl of 2–3 carbons, optionally substituted alkyl and aryl sulfonyl, or optionally substituted alkyl and aryl phosphoryl;
$R_4$ is OtBu, $OCH_3$, $C_2$–$C_7$ normal, branched, cyclic saturated, cyclic unsaturated alkoxy, or $R_4$ together with $R_1$ and $-N-C_\alpha-C(O)-$ forms a 4–7 membered ring, with bridging atoms being C, O, N, P, or S, or combinations thereof; and $R_5$ is hydrogen or a radical that can be converted to a phenolic OH group during or after said Baeyer-Villiger Reaction; and a second container which contains a polar aprotic solvent for dissolving said compound.

11. The kit of claim 10, wherein X is —$N^+(CH_3)_3$.

12. The kit of claim 11, wherein Y has the formula:

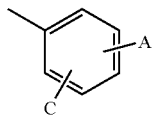

wherein A is hydrogen, fluorinated alkyl, or $NO_2$, and C is fluorinated alkyl or $NO_2$.

13. The kit of claim 12, wherein:
$R_1$ is hydrogen;
$R_2$ is tert-butyloxycarbonyl; and
$R_4$ is $OCH_3$.

14. The kit of claim 13, wherein $R_5$ is hydrogen.

15. The kit of claim 10, wherein said compound has the formula:

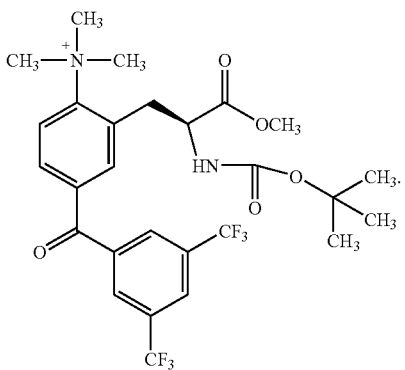

* * * * *

UNITED STATES PATENT AND TRADEMARK OFFICE
CERTIFICATE OF CORRECTION

| | |
|---|---|
| PATENT NO. | : 7,115,766 B2 |
| APPLICATION NO. | : 10/433053 |
| DATED | : October 3, 2006 |
| INVENTOR(S) | : Mulholland et al. |

It is certified that error appears in the above-identified patent and that said Letters Patent is hereby corrected as shown below:

Claim 1, Column 60, line 62, please delete the word "and."

Claim 6, Column 61, the chemical formula and accompanying period should be replaced with the following structure:

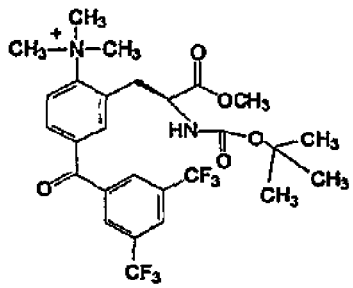

Claim 7, Column 62, line 5, please add the word --and-- after "thereof;".

Claim 15, Column 64, the chemical formula and accompanying period should be replaced with the following structure:

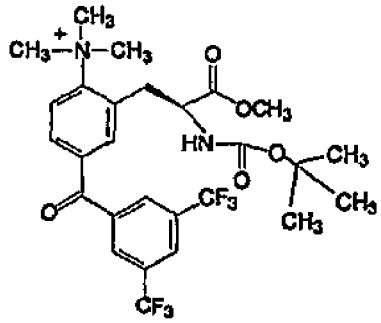

Signed and Sealed this

Nineteenth Day of December, 2006

JON W. DUDAS
*Director of the United States Patent and Trademark Office*